US012754185B2

(12) United States Patent
Geissler et al.

(10) Patent No.: US 12,754,185 B2
(45) Date of Patent: Oct. 6, 2026

(54) HBV DIAGNOSTIC, PROGNOSTIC, AND THERAPEUTIC METHODS AND PRODUCTS

(71) Applicant: Abbott Laboratories, Abbott Park, IL (US)

(72) Inventors: Rene Geissler, Abbott Park, IL (US); Megha Patel, Abbott Park, IL (US); Xiaoxing Qiu, Abbott Park, IL (US); Gavin Cloherty, Abbott Park, IL (US)

(73) Assignee: Abbott Laboratories, Abbott Park, IL (US)

( * ) Notice: Subject to any disclaimer, the term of this patent is extended or adjusted under 35 U.S.C. 154(b) by 438 days.

(21) Appl. No.: 18/474,895

(22) Filed: Sep. 26, 2023

(65) Prior Publication Data

US 2024/0118278 A1 Apr. 11, 2024

Related U.S. Application Data

(63) Continuation of application No. PCT/US2023/074164, filed on Sep. 14, 2023.

(60) Provisional application No. 63/406,830, filed on Sep. 15, 2022.

(51) Int. Cl.

| | |
|---|---|
| ***C07K 14/01*** | (2006.01) |
| ***C07K 14/02*** | (2006.01) |
| ***C12N 7/01*** | (2006.01) |
| ***C12Q 1/6804*** | (2018.01) |
| ***G01N 33/569*** | (2006.01) |
| ***G01N 33/576*** | (2006.01) |

(52) U.S. Cl.

CPC ... *G01N 33/56983* (2013.01); *G01N 2333/02* (2013.01); *G01N 2469/10* (2013.01)

(58) Field of Classification Search

CPC ........... G01N 2800/52; G01N 33/5762; G01N 2333/02; G01N 2440/14; C07K 14/02

See application file for complete search history.

(56) References Cited

PUBLICATIONS

Charre. Caroline et al: "Non-invasive biomarkers for chronic hepatitis B virus infection management", Antiviral Research, Elsevier BV, NL, vol. 169, Jul. 6, 2019 (Jul. 6, 2019), XP085774833.

Zhao Qiong et al: "Hepatitis B Virus Core Protein Dephosphorylation Occurs during Pregenomic RNA Encapsidation", Journal of Virology, vol. 92, No. 13, Jul. 1, 2018 (Jul. 1, 2018), XP093104459.

Lefeuvre Caroline et al: "A Pleiotropic Role of the Hepatitis B Virus Core Protein in Hepatocarcinogenesis", International Journal of Molecular Sciences, vol. 22, No. 24, Dec. 20, 2021 (Dec. 20, 2021), p. 13651, XP093104414.

International Searching Authority, International Search Report and Written Opinion for PCT Application No. PCT/US2023/074164 mailed Jan. 29, 2024.

*Primary Examiner* — Barry A Chestnut

(74) *Attorney, Agent, or Firm* — Lisa Mueller; Casmir Jones SC

(57) ABSTRACT

Provided herein are compositions, systems, and methods for assessing and monitoring disease stage and phases, predicting likelihood of disease progression, and predicting and monitoring responses to hepatitis B virus infection.

16 Claims, 14 Drawing Sheets

Specification includes a Sequence Listing.

| | |
|---|---|
| SEQ ID NO:1 | MDIDPYKEFGATVELLSFLPSDFFPSVRDLLDTASALYREALESPEHCSPHHTALRQAILCWGELMTLAT WVGNNLEDPASRDLVVNYVNTNMGLKIRQLLWFHISCLTFGRETVLEYLVSFGVWIRTPPAYRPPNAPI LSTLPETTVVRRRDRGRSPRRRTPSPRRRRSQSPRRRRSQSRESQC |
| SEQ ID NO:2 | RRRDRGRSPRR RTPSPRRRRS QSPRRRRSQS RESQC |
| SEQ ID NO:3 | MDIDPYKEFGATVELLSFLPSDFFPSVRDLLDTASALYREALESPEHCSPHHTALRQAILCWGELMTLAT WVGNNLEDPASRDLVVNYVNTNMGLKIRQLLWFHISCLTFGRETVLEYLVSFGVWIRTPPAYRPPNAPI LSTLPETTVV |

FIG. 3

```
         10        20        30        40        50        60        70        80
....:....|....:....|....:....|....:....|....:....|....:....|....:....|....:....|

MDIDPYKEFGAsVELLS-FLPSDFFPSiRDLLDTASALYReALESPEHCSPHHTALRQAILCWGELM-nLATWVGsNLED
l   t      ta        a  y nv       a  f ds   sd  tan   i   vv  vdvi t ss   n  q
    h                t             t                                s      g  d
                                                                           v
                                                                           a
                                                                           t

         90       100       110       120       130       140       150       160
....:....|....:....|....:....|....:....|....:....|....:....|....:....|....:....|

PaSReLVVsYVNvNMGLKiRQLLWFHISCLTFGRETVlEYLVSFGVWIRTPpAYRPPNAPILSTLPETTVVRRR---GRS
qta dai n   thv i f  i    v  i    dv i             tp   q          na i q dr c t
 i   q  g         l               q  v             q                c
 v                                                 l

        170       180       190
....:....|....:....|....:....|

PR-rRTPSPRRRRSQSPRRRRSQSRe-SQC
 r-                  tk pa p
                         g
                         d
```

FIG. 5A

```
        10        20        30        40        50        60        70        80
....:....|....:....|....:....|....:....|....:....|....:....|....:....|....:....|
                .   '                                               *
MDIDpYKEFGASVELLSF-LPSDFFPSIRDLLDTASALYREALESPEHCSPHHTALRQAIlCWGELMNLATWVGSNLEDP
    t      ta        t    nv       t  h          ta    i   vv  v   t      g  d q
    h       l        a             a              h            d   s      n  q
            m                                     y
            g

        90       100       110       120       130       140       150       160
....:....|....:....|....:....|....:....|....:....|....:....|....:....|....:....|
      .                                                      .
ASRELVVsYVNVNMGLKiRQLLWFHISCLTFGRETVLEYLVSFGVWIRTPpAYRPpNAPILSTLPETTVVRRRGRSPRRR
s  da  g   t   i l  i    l  i   kdv               tp   qx          a i q c t
       n         f                                s    a               g r
                                                  l
                                                  a

       170       180
....:....|....:....|....:
TPSPRRRRSQSPRRRRSQSRE-SQC
                tk  g p
```

FIG. 5C

```
         10        20        30        40        50        60        70        80
....:....|....:....|....:....|....:....|....:....|....:....|....:....|....:....|
 :                                                       .            .    :
MDIDPYKEFGASVELLS-FLPSDFFPSIRDLLDTASALYREALESPEHCSPHHTALRQAILCWGELMNLATWVGSNLEDP
    t       a  i     a    nv e     t  h d        ta    i   vv  v   s      g  d q
    h                              a

         90       100       110       120       130       140       150       160
....:....|....:....|....:....|....:....|....:....|....:....|....:....|....:....|
                                         .      .   :    .                     :
ASRELVVsYVNVNMGLKiRQlLWFHISCLTFGRETVLEYLVSFGVWIRTPpAYRPPNAPILSTLPETTVVRRRGRSPRRR
   dai g   i   i l  i           sav               tp   q           a i q c ts
                 f               d                l                    p
                                 q                q                    c
                                                  i

        170       180
....:....|....:....|....
         .
TPSPRRRRSQSPRRRRSQSRESQC
                tk  gp
                    d
```

FIG. 5D

HBV DIAGNOSTIC, PROGNOSTIC, AND THERAPEUTIC METHODS AND PRODUCTS

RELATED APPLICATION INFORMATION

This application is a continuation of International Application No. PCT/US23/74164, filed Sep. 14, 2023, which claims priority to U.S. Application No. 63/406,830 filed on Sep. 15, 2022, the contents of which are herein incorporated by reference.

SEQUENCE LISTING STATEMENT

The contents of the electronic sequence listing titled 40844_601-SQL-ST26.xml (Size: 57,344 bytes; and Date of Creation: Sep. 14, 2023) is herein incorporated by reference in its entirety.

FIELD

Provided herein are compositions, systems, and methods for assessing and monitoring hepatitis B virus (HBV) stage and phases, and predicting and monitoring responses to therapy by determining the amount of Hepatitis B core antigen (HBcAg) and/or phosphorylated Hepatitis B core antigen (P-HBcAg) in a sample obtained from a subject.

BACKGROUND

Hepatitis is a general term meaning 'inflammation of the liver' and has a number of causes. Viral causes are among the most common, and may be caused by hepatitis A, B, C, D or E virus. Hepatitis B virus (HBV), in particular, is a serious and common infectious disease of the liver, affecting millions of people throughout the world.

HBV is a hepatotrophic DNA virus belonging to the Hepadnaviridae. The full-length of the viral genome is about 3.2 kb, and it has four open reading frames (ORFs) including surface antigen (the "S gene"), core antigen (the "C gene"), DNA polymerase (the "P gene") and a gene of undetermined function referred to as the "X gene".

More than 2 billion people alive today have been infected with HBV at some time in their lives and of these about 248 million remain chronically infected and become carriers of the virus. HBV infection can cause acute and chronic type B hepatitis, and may eventually lead to the development of chronic hepatic insufficiency, cirrhosis, and hepatocellular carcinoma. In addition, HBV carriers can transmit the disease for many years.

HBV is transmitted by percutaneous or parenteral contact with infected bodily fluids or blood. The most common route of infection is via vertical transmission from mother to her baby, and in adults through sexual intercourse or shared intravenous needles or ear-piercing equipment. Many cases of acute HBV infection occur without a traceable route of infection.

Persons with chronic HBV infection ("carriers") have a 12-300 times higher risk of developing hepatocellular carcinoma than non-carriers and globally HBV causes 60-80% of the world's primary liver cancers. Every year about 25% of the over 4 million acute clinical cases die from chronic active hepatitis, cirrhosis or HBV-induced liver cancer. As a consequence, HBV ranks second only to tobacco as a known human carcinogen.

Although vaccines against HBV has been widely used for several decades, the HBV prevalence rate in the population still remains high. Current therapies for chronic HBV infection have only limited inhibitory effects on viral gene expression and replication in the majority of chronically infected patients. Lamivudine, for example, suppresses HBV replication in carriers, but the effect is reversible if therapy is stopped. Moreover, a major limitation of chronic Lamivudine therapy is the development of viral resistance, which typically develops after six months of treatment. Resistance is usually associated with mutations in the highly conserved catalytic region of the HBV polymerase gene. Moreover, current markers for HBV (e.g. HBsAg, anti-HBs, HBeAg, anti-HBe) have a limited ability to measure efficacy of antiviral treatments, such as a limited ability to measure a decrease in HBV DNA levels in subjects following treatment.

For these reasons, there remains a need for new treatment courses of action and methods of selecting and monitoring appropriate treatments for HBV infection.

BRIEF DESCRIPTION OF THE DRAWINGS

FIG. 3 shows various sequences related to P-HBcAg and/or HBcAg.

FIG. 5A shows a consensus sequence for HBcAg. FIG. 5C shows a consensus sequence for HBcAg Genotype B. FIG. 5D shows a consensus sequence for HBcAg Genotype C.

Figure 1:
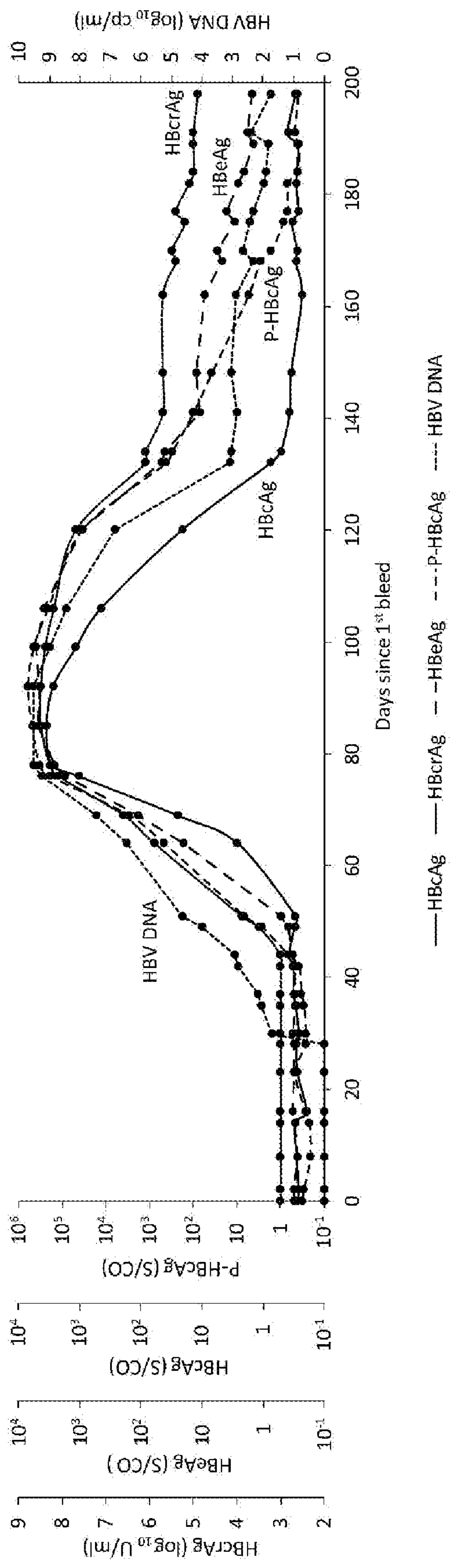
FIG. 1 shows an HBV seroconversion panel comparing levels of phosphorylated HBV core antigen (P-HBcAg), HBV core antigen (HBcAg), HBeAg and HBcrAg with levels of HBV DNA over time.

STA
NEQK
NHQK
NDEQ
QHRK
MILV
MILF
HY
FYW

A . (period) indicates conservation between groups of weakly similar properties as below—roughly equivalent to scoring=<0.5 and >0 in the Gonnet PAM 250 matrix:

CSA
ATV
SAG
STNK
STPA
SGND
SNDEQK
NDEQHK
NEQHRK
FVLIM
HFY

SUMMARY

In some aspects, provided herein are methods of assessing and monitoring stage or phase of chronic HBV infection or monitoring response to a treatment for chronic HBV in a subject. In some embodiments, the method comprises performing an assay to detect the presence or level of Hepatitis B core antigen (HBcAg) and phosphorylated Hepatitis B core antigen (P-HBcAg) in at least one sample obtained from a subject diagnosed with chronic HBV or receiving a treatment for chronic HBV. In some embodiments, the assay comprises contacting the at least one sample with an antibody that specifically binds to HBcAg and an antibody that specifically binds to P-HBcAg. In some embodiments, the method further comprises assessing and monitoring stage or phase of chronic HBV infection or monitoring response to the treatment for chronic HBV based on the presence or level of HBcAg and P-HBcAg in the at least one sample.

In some embodiments, the subject is being assessed and monitored for the stage or phase of chronic HB. In some embodiments, the method further comprises providing a treatment for chronic HBV to the subject based upon the presence or level of HBcAg and P-HBcAg in the at least one sample.

In some embodiments, the subject is receiving a treatment for chronic HBV. In some embodiments, the method further comprises altering the treatment for HBV based on the presence or level of HBcAg and P-HBcAg in the at least one sample.

In some aspects, provided herein are methods of assessing and monitoring stage or phase or chronic HBV infection. In some embodiments, the method comprises performing an assay to detect the presence or level of Hepatitis B core antigen (HBcAg) in at least one sample obtained from a subject diagnosed with chronic HBV. In some embodiments, the assay comprises contacting the at least one sample with an antibody that specifically binds to HBcAg. In some embodiments, the method comprises determining the amount of infectious HBV particles in the at least one sample based upon the presence or level of HBcAg in the at least one sample. In some embodiments, the amount of infectious HBV particles is determined regardless of whether the subject has or has not received a treatment for HBV prior to performing the assay (e.g. the assay to detect the presence or level of HBcAg in the at least one sample). In some embodiments, the method further comprises providing a treatment for chronic HBV to the subject when the amount of infectious HBV particles in the at least one sample is equal to or above a threshold value.

In some aspects, provided herein are methods of monitoring response to a treatment for chronic Hepatitis B (HBV) infection in a subject. In some embodiments, the method comprises performing an assay to detect the presence or level of Hepatitis B core antigen (HBcAg) in at least one sample obtained from a subject receiving a treatment for chronic HBV. In some embodiments, the assay comprises contacting the at least one sample with an antibody that specifically binds to HBcAg. In some embodiments, the method comprises determining the amount of infectious HBV particles in the at least one sample based upon the presence or level of HBcAg in the at least one sample. In some embodiments, the method comprises using the amount of infections HBV particles in the sample to determine whether the treatment for chronic HBV is efficacious or not efficacious in the subject. In some embodiments, the method comprises determining that the treatment is efficacious when the amount of infectious HBV particles in the at least one sample is less than a reference level. In some embodiments, the method comprises determining that the treatment is not efficacious when the amount of infectious HBV particles in the at least one sample is greater than or equal to a reference level.

In some embodiments, the method of monitoring response to treatment for chronic Hepatitis B (HBV) infection in a subject comprises performing an assay to detect the presence or level of Hepatitis B core antigen (HBcAg) and phosphorylated Hepatitis B core antigen (P-HBcAg) in at least one sample obtained from a subject receiving a treatment for chronic HBV. In some embodiments, the assay comprises contacting the at least one sample with an antibody that specifically binds to HBcAg and an antibody that specifically binds to P-HBcAg. In some embodiments, the method comprises determining the amount of infectious HBV particles in the at least one sample based upon the presence or level of HBcAg in the at least one sample. In some embodiments, the method comprises determining the amount of non-infectious HBV particles in the at least one sample based upon the presence or level of P-HBcAg in the at least one sample. In some embodiments, the method comprises determining the amount of infectious HBV particles in the at least one sample based upon the presence or level of HBcAg in the at least one sample and amount of non-infectious HBV particles in the at least one sample based upon the presence or level of P-HBcAg in the at least one sample. In some embodiments, the method comprises determining response to the treatment for chronic HBV based upon the amount of infectious and/or non-infectious HBV particles in the at least one sample. For example, in some embodiments determining response to the treatment comprises determining whether the treatment is efficacious or not efficacious in the subject. In some embodiments, the treatment is determined to be efficacious when the amount of infectious HBV particles in the at least one sample is less than a reference level. In some embodiments, the treatment is determined to be efficacious when the amount of infectious HBV particles in the at least one sample is less than a reference level and the amount of non-infectious HBV particles in the at least one sample is less than a reference level. In some embodiments, the treatment is determined to not be efficacious when the amount of infectious HBV particles in the at least one sample is greater than or equal to a reference level.

In some embodiments, the method of monitoring response to a treatment for chronic Hepatitis B (HBV) infection in a subject comprises performing an assay to detect the presence or level of Hepatitis B core antigen (HBcAg) and phosphorylated Hepatitis B core antigen (P-HBcAg) in at least two samples obtained from a subject receiving a treatment for chronic HBV. In some embodiments, the at least two samples comprise a first sample obtained from the subject at a first time point before or after receiving the treatment for chronic HBV and a second sample obtained from the subject at a second time point after the first time point. In some embodiments, the assay comprises contacting the at least two samples with an antibody that specifically binds to HBcAg and an antibody that specifically binds to P-HBcAg. In some embodiments, the method comprises determining the amount of infectious HBV particles in the at least two samples based upon the presence or level of HBcAg and/or determining the amount of non-infectious HBV particles in the at least two samples based upon the presence or level of P-HBcAg. In some embodiments, the method comprises determining response to the treatment for chronic HBV based upon the amount of infectious and/or non-infectious HBV particles in the at least two samples. For example, determining the response to the treatment may comprise determining whether the treatment is efficacious or not efficacious. In some embodiments, the treatment is determined to be efficacious when the amount of infectious HBV particles in the second sample reduced by at least an absolute amount compared to the amount of infectious HBV particles in the first sample. In some embodiments, the treatment is determined to be efficacious when the amount of infectious HBV particles in the second sample reduced by at least an absolute amount compared to the amount of infectious HBV particles in the first sample and the amount of non-infectious HBV particles in the second sample is reduced by at least an absolute amount compared to the amount of non-infectious HBV particles in the first sample. In some embodiments, the treatment is determined to not be efficacious when the amount of infectious HBV particles in the second sample is not reduced by at least an absolute amount compared to the amount of infectious HBV particles in the first sample.

In some embodiments, the first sample is obtained from the subject within 24 hours of receiving the treatment for chronic HBV. In some embodiments, the second sample is obtained from the subject 10-14 weeks after the first sample. In some embodiments, the first sample is obtained from the subject within 24 hours of receiving the treatment for chronic HBV the second sample is obtained from the subject 10-14 weeks after the first sample.

In some embodiments, methods of monitoring response to a treatment for chronic HBV described herein further comprise altering the treatment for chronic HBV when the treatment is determined to not be efficacious. In some embodiments, altering the treatment for chronic HBV comprises providing to the subject an increased dose of the treatment, increasing the frequency of dosing with the treatment, providing to the subject a second treatment, or any combination thereof.

In some embodiments, the antibody that specifically binds to HBcAg may bind to an epitope comprising at least 3 amino acids of SEQ ID NO: 2 or SEQ ID NO:25 and/or the antibody that specifically binds to P-HBcAg may bind to an epitope comprising at least 3 amino acids of SEQ ID NO: 2, provided that at least one amino acid of SEQ ID NO: 2 or SEQ ID NO:25 is phosphorylated.

In some embodiments, the treatment for chronic HBV may be an interferon, nucleos(t)ide analogue, a nucleic acid, an immunomodulator, a core protein assembly inhibitor, a capsid assembly modulator (CAM), an HBsAg release inhibitor, an entry inhibitor, interfering RNA, a DNA modifying agent, or a combination thereof. In some embodiments, the interferon is interferon alpha-2a or PEGylated interferon alpha-2a. In some embodiments, the nucleos(t)ide analogue is lamivudine, adefovir, tenofovir, telbivudine, or entecavir. In some embodiments, the nucleic acid is an siRNA, an antisense oligonucleotide, an shRNA, or a miRNA. In some embodiments, the core protein assembly inhibitor is NVR 3-1983, GLS4 or BAY 41-4109. In some embodiments, the CAM is JNJ-632, AT130, or BAY41-4109. In some embodiments, the HBsAg release inhibitor is REP 9 AC. In some embodiments, the entry inhibitor is Myrcludex-B. In some embodiments, the treatment is a combination of any of the above treatments.

In some embodiments, performing the assay to measure the level of HBcAg in the at least one sample comprises contacting the at least one sample, either simultaneously or sequentially, in any order with: a Hepatitis B core antigen (HBcAg) capture antibody which binds to an epitope on the C-terminus of HBcAg to form a capture antibody-HBcAg complex; and a detection antibody binds to an epitope on HBcAg that is not bound by the HBcAg capture antibody, such that a capture antibody-HBcAg-detection antibody complex is formed. In some embodiments, the performing the assay further comprises measuring the level of HBcAg in the sample based on a signal generated by a detectable label in the capture antibody-HBcAg-detection antibody complex.

In some embodiments, performing the assay to measure the level of P-HBcAg in the sample comprises contacting the sample, either simultaneously or sequentially, in any order with: a phosphorylated Hepatitis B core antigen (P-HBcAg) capture antibody which binds to an epitope on the C-terminus of P-HBcAg to form a capture antibody-P-HBcAg complex; and a detection antibody binds to an epitope on P-HBcAg that is not bound by the P-HBcAg capture antibody, such that a capture antibody-P-HBcAg-detection antibody complex is formed. In some embodiments, performing the assay further comprises measuring the level of P-HBcAg in the sample based on a signal generated by a detectable label in the capture antibody-P-HBcAg-detection antibody complex.

In some aspects, provided herein is a use of reagents for detection of the presence or level of Hepatitis B core antigen (HBcAg) and phosphorylated Hepatitis B core antigen (P-HBcAg) in a method of assessing a stage or phase of Hepatitis B (HBV) infection or monitoring a response to a treatment for chronic HBV in a subject.

In some aspects, provided herein is a kit or system comprising reagents for detection of the presence, level, or status of Hepatitis B core antigen (HBcAg) and phosphorylated Hepatitis B core antigen (P-HBcAg).

Section headings as used in this section and the entire disclosure herein are merely for organizational purposes and are not intended to be limiting.

1. Definitions

Unless otherwise defined, all technical and scientific terms used herein have the same meaning as commonly understood by one of ordinary skill in the art. In case of conflict, the present document, including definitions, will control. Various embodiments of the methods and materials are described below, although methods and materials similar or equivalent to those described herein can be used in practice or testing of the present disclosure. All publications, patent applications, patents and other references mentioned herein are incorporated by reference in their entirety. The materials, methods, and examples disclosed herein are illustrative only and not intended to be limiting.

As used herein, the term "algorithm" refers to a process or set of rules to be followed in calculations or other problem-solving operations (such as, for example, by one or more computers containing one or more software programs that analyze data from one or more markers and optionally, one or more biometric data (such as for example, history of intravenous drug use, chronic liver and/or kidney disease, employment history as a healthcare worker, age, gender, race, etc.), and includes the requisite code to execute the algorithm). For example, analysis of HBV marker data performed using an algorithm(s) can include analyzing: (1) single biomarkers (e.g., Hepatitis B core antigen (HBcAg), phosphorylated Hepatitis B core antigen (P-HBcAg); (2) single markers with one or more biometric data; (3) groups of two or more markers (e.g., groups comprising Hepatitis B core antigen (HBcAg) and phosphorylated Hepatitis B core antigen (P-HBcAg), optionally included one or more additional markers); or (4) groups of two or more markers with one or more biometric data. Still further approaches can employ multiple analyte algorithms (such as described in U.S. Patent Publication No. 2016/0342757, herein incorporated by reference) rather than a single marker (with or without biometric data) or a group of single markers (with or without biometric data). Such algorithms can be used as part of the methods described herein to derive one or more values that reflect disease status, stage, or phase, to predict likelihood of disease progression, and/or predict or monitor response to therapy or treatment.

As used herein, the term "antibody" refers to an immunoglobulin molecule or immunologically active portion thereof, namely, an antigen-binding portion. Examples of immunologically active portions of immunoglobulin molecules include F(ab) and F(ab')2 fragments which can be generated, e.g., by treating an antibody with an enzyme such as pepsin. Examples of antibodies that can be used in the present disclosure include, but are not limited to, polyclonal antibodies, monoclonal antibodies, chimeric antibodies, human antibodies, humanized antibodies, recombinant antibodies, single-chain Fvs ("scFv"), affinity maturated antibodies, single chain antibodies, single domain antibodies, F(ab) fragments, F(ab') fragments, disulfide-linked Fvs ("sdFv"), and antiidiotypic ("anti-Id") antibodies, among others, and functionally active epitope-binding fragments of any of the above. The antibody may be of classes IgG, IgM, IgA, IgD or IgE, or fragments or derivatives thereof. The antibody may be derivatized by the attachment of one or more chemical, peptide, or polypeptide moieties known in the art. The antibody may be conjugated with a chemical moiety.

"Antibody fragment" as used herein refers to a portion of an intact antibody comprising the antigen-binding site or variable region. The portion does not include the constant heavy chain domains (i.e., CH2, CH3, or CH4, depending on the antibody isotype) of the Fc region of the intact antibody. Examples of antibody fragments include, but are not limited to, Fab fragments, Fab' fragments, Fab'-SH fragments, $F(ab')_2$ fragments, Fd fragments, Fv fragments, diabodies, single-chain Fv (scFv) molecules, single-chain polypeptides containing only one light chain variable domain, single-chain polypeptides containing the three CDRs of the light-chain variable domain, single-chain polypeptides containing only one heavy chain variable region, and single-chain polypeptides containing the three CDRs of the heavy chain variable region.

The "area under curve" or "AUC" refers to area under a ROC curve. AUC under a ROC curve is a measure of accuracy. An AUC of 1 represents a perfect test, whereas an AUC of 0.5 represents an insignificant test. A preferred AUC may be at least approximately 0.700, at least approximately 0.750, at least approximately 0.800, at least approximately 0.850, at least approximately 0.900, at least approximately 0.910, at least approximately 0.920, at least approximately 0.930, at least approximately 0.940, at least approximately 0.950, at least approximately 0.960, at least approximately 0.970, at least approximately 0.980, at least approximately 0.990, or at least approximately 0.995.

A "receiver operating characteristic" curve or "ROC" curve refers to a graphical plot that illustrates the performance of a binary classifier system as its discrimination threshold is varied. For example, an ROC curve can be a plot of the true positive rate against the false positive rate for the different possible cutoff points of a diagnostic test. It is created by plotting the fraction of true positives out of the positives (TPR=true positive rate) vs. The fraction of false positives out of the negatives (FPR=false positive rate), at various threshold settings. TPR is also known as sensitivity, and FPR is one minus the specificity or true negative rate. The ROC curve demonstrates the tradeoff between sensitivity and specificity (any increase in sensitivity will be accompanied by a decrease in specificity); the closer the curve follows the left-hand border and then the top border of the ROC space, the more accurate the test; the closer the curve comes to the 45-degree diagonal of the ROC space, the less accurate the test; the slope of the tangent line at a cutoff point gives the likelihood ratio (LR) for that value of the test; and the area under the curve is a measure of test accuracy.

"Bead" and "particle" are used herein interchangeably and refer to a substantially spherical solid support. One example of a bead or particle is a microparticle. Microparticles that can be used herein can be any type known in the art. For example, the bead or particle can be a magnetic bead or magnetic particle. Magnetic beads/particles may be ferromagnetic, ferrimagnetic, paramagnetic, superparamagnetic or ferrofluidic. Exemplary ferromagnetic materials include Fe, Co, Ni, Gd, Dy, $CrO_2$, MnAs, MnBi, EuO, and NiO/Fe. Examples of ferrimagnetic materials include $NiFe_2O_4$, $CoFe_2O_4$, $Fe_3O_4$ (or $FeO·Fe_2O_3$). Beads can have a solid core portion that is magnetic and is surrounded by one or more non-magnetic layers. Alternately, the magnetic portion can be a layer around a non-magnetic core. The microparticles can be of any size that would work in the methods described herein, e.g., from about 0.75 to about 5 nm, or from about 1 to about 5 nm, or from about 1 to about 3 nm.

"Binding protein" is used herein to refer to a monomeric or multimeric protein that binds to and forms a complex with a binding partner, such as, for example, a polypeptide, an antigen, a chemical compound or other molecule, or a substrate of any kind. A binding protein specifically binds a binding partner. Binding proteins include antibodies, as well as antigen-binding fragments thereof and other various forms and derivatives thereof as are known in the art and described herein below, and other molecules comprising one or more antigen-binding domains that bind to an antigen molecule or a particular site (epitope) on the antigen molecule. Accordingly, a binding protein includes, but is not limited to, an antibody a tetrameric immunoglobulin, an IgG molecule, an IgG1 molecule, a monoclonal antibody, a chimeric antibody, a CDR-grafted antibody, a humanized antibody, an affinity matured antibody, and fragments of any such antibodies that retain the ability to bind to an antigen.

"Bispecific antibody" is used herein to refer to a full-length antibody that is generated by quadroma technology (also referred to as hybrid-hybridoma technology; see Milstein et al., *Nature,* 305(5934): 537-540 (1983)), by chemical conjugation of two different monoclonal antibodies (see, Staerz et al., *Nature,* 314(6012): 628-631 (1985)), or by knob-into-hole or similar approaches, which introduce mutations in the Fc region (see Holliger et al., *Proc. Natl. Acad. Sci. USA,* 90(14): 6444-6448 (1993)), resulting in multiple different immunoglobulin species of which only one is the functional bispecific antibody. A bispecific antibody binds one antigen (or epitope) on one of its two binding arms (one pair of HC/LC), and binds a different antigen (or epitope) on its second arm (a different pair of HC/LC). By this definition, a bispecific antibody has two distinct antigen-binding arms (in both specificity and CDR sequences), and is monovalent for each antigen to which it binds to.

"CDR" is used herein to refer to the "complementarity determining region" within an antibody variable sequence. There are three CDRs in each of the variable regions of the heavy chain and the light chain. Proceeding from the N-terminus of a heavy or light chain, these regions are denoted "CDR1", "CDR2", and "CDR3", for each of the variable regions. The term "CDR set" as used herein refers to a group of three CDRs that occur in a single variable region that binds the antigen. An antigen-binding site, therefore, may include six CDRs, comprising the CDR set from each of a heavy and a light chain variable region. A polypeptide comprising a single CDR, (e.g., a CDR1, CDR2, or CDR3) may be referred to as a "molecular recognition unit." Crystallographic analyses of antigen-antibody complexes have demonstrated that the amino acid residues of CDRs form extensive contact with bound antigen, wherein the most extensive antigen contact is with the heavy chain CDR3. Thus, the molecular recognition units may be primarily responsible for the specificity of an antigen-binding site. In general, the CDR residues are directly and most substantially involved in influencing antigen binding.

The exact boundaries of these CDRs have been defined differently according to different systems. The system described by Kabat (Kabat et al., *Sequences of Proteins of Immunological Interest* (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as "Kabat CDRs". Chothia and coworkers (Chothia and Lesk, *J. Mol. Biol.,* 196: 901-917 (1987); and Chothia et al., *Nature,* 342: 877-883 (1989)) found that certain sub-portions within Kabat CDRs adopt nearly identical peptide backbone conformations, despite having great diversity at the level of amino acid sequence. These sub-portions were designated as "L1", "L2", and "L3", or "H1", "H2", and "H3", where the "L" and the "H" designate the light chain and the heavy chain regions, respectively. These regions may be referred to as "Chothia CDRs", which have boundaries that overlap with Kabat CDRs. Other boundaries defining CDRs overlapping with the Kabat CDRs have been described by Padlan, *FASEB J.,* 9: 133-139 (1995), and MacCallum, *J. Mol. Biol.,* 262(5): 732-745 (1996). Still other CDR boundary definitions may not strictly follow one of the herein systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although certain embodiments use Kabat- or Chothia-defined CDRs.

"Favorable" as used herein means in certain aspects that when the level(s) of one or more biomarkers measured and/or determined according to the methods described herein is compared to one or more reference levels is less than or lower than the reference level(s). However, in other aspects, depending on the biomarker(s) being measured or determined, the term "favorable" may mean that the level(s) of the one or more biomarkers measured and/or determined according to the methods described herein is higher or greater than the one or more reference levels. Whether a "favorable" level is higher or lower compared to the reference level depends on whether there is a rise or fall of the biomarker in the context of HBV infection. In some embodiments, "favorable" levels indicate that the levels of one of more biomarkers have decreased by at least an absolute amount from a first time point to a second time point. For example, a "favorable" level may indicate that the level of HBcAg and/or the level of P-HBcAg has decreased by at least an absolute amount from a first sample to a second sample collected after the first sample. Generally, a favorable level of a biomarker is one that suggests an absence of HBV infection, improvement in a subject's health with respect to an HBV infection, or that a subject is benefitting from treatment (or continued treatment) with an HBV therapeutic (i.e. that an HBV treatment is efficacious in the subject). In some embodiments, a favorable level correlates with a clinical improvement in infection. For instance, clinical improvement of the subject can be determined by any number of a variety of parameters (e.g., patient reports, improvement in skin color (e.g., less yellow or jaundice in color), a reduction in the amount of liver inflammation, etc.).

"Unfavorable" as used herein means in certain aspects that when the level(s) of one or more biomarkers measured and/or determined according to the methods described herein is compared to one or more reference levels is higher or greater than the reference level(s). However, in other aspects, depending on the biomarker(s) being measured or determined, the term "unfavorable" may mean that the level(s) of the one or more biomarkers measured and/or determined according to the methods described herein is less than or lower than the one or more reference levels. As described above, whether an "unfavorable" level is higher or lower compared to the reference level depends on whether there is a rise or fall of the biomarker in the context of HBV infection. In some embodiments, "unfavorable" levels indicate that the levels of one of more biomarkers have not decreased by at least an absolute amount from a first time point to a second time point. For example, an "unfavorable" level may indicate that the level of HBcAg and/or the level of P-HBcAg has not decreased by at least an absolute amount from a first sample to a second sample collected after the first sample. Generally, an unfavorable level of a biomarker is one that suggests a presence of HBV infection, worsening of a subject's health with respect to an HBV infection, or that a subject is not benefiting from an HBV treatment (i.e. an HBV treatment is not efficacious in the subject). In some embodiments, an unfavorable level correlates with a clinical worsening of infection. For instance, worsening of the condition of the subject can be determined by any number of a variety of parameters (e.g., patient reports, a change or worsening of skin color (e.g., an increase in yellow or greater jaundice in color), increase in liver inflammation, etc.).

"Identical" or "identity" as used herein in the context of two or more polypeptide or polynucleotide sequences, may mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation.

"Isoform(s) of hepatitis surface antigen or HBsAg" or "hepatitis surface antigen or HBsAg isoform(s)" as used herein refers to one or more polypeptides encoded by the pre-S1, pre-S2 and/or S sections of the HBsAg gene which are referred to as large (L), middle (M) and small (S) HBs. Each of the large, middle and small HBs contain the S domain. The middle HB s protein (MHBs) has a 55-amino acid long N-terminal extension, the preS2 domain. The HBV large surface protein (LHBs) has an additional 108 or 119-amino acid N-terminal extension, the preS1 domain. The HBsAg of infectious virions and subviral particles consists predominantly of HBV small surface proteins (SHBs), with LHBs and MHBs as minor components. The isoforms contemplated herein can comprise the (i) large HBs only; (ii) the middle HBs only; (iii) the small HBs only (iv) the large HBs and middle HBs; (v) the large HBs and small HBs; (vi) the middle HBs and small HBs; or (vii) the large HBs, middle HBs and small HBs.

"Substantially identical," as used herein may mean that a first and second sequence are at least from about 50% to about 99% identical over a region of from about 8 to about 100 or more residues (including any range within from about 8 to about 100 residues).

As used herein, the term "test sample" or "sample" generally refers to a biological material being tested for and/or suspected of containing an analyte of interest, such as a marker described herein. The test sample may be derived from any biological source, such as, a physiological fluid, including, but not limited to, whole blood, serum, plasma, interstitial fluid, saliva, ocular lens fluid, cerebral spinal fluid, sweat, urine, milk, ascites fluid, mucous, nasal fluid, sputum, synovial fluid, peritoneal fluid, vaginal fluid, menses, amniotic fluid, semen and so forth. In some embodiments, the sample is a whole blood sample. In some embodiments, the sample is a plasma sample. In yet other embodiments, the sample is a serum sample. The test sample may be used directly as obtained from the biological source or following a pretreatment to modify the character of the sample. For example, such pretreatment may include preparing plasma from blood, diluting viscous fluids and so forth. Methods of pretreatment may also involve filtration, precipitation, dilution, distillation, mixing, concentration, inactivation of interfering components, the addition of reagents, lysing, etc. Moreover, it may also be beneficial to modify a solid test sample to form a liquid medium or to release the analyte.

The term "nucleic acid" refers to a nucleotide polymer, and unless otherwise limited, includes known analogs of natural nucleotides that can function in a similar manner (e.g., hybridize) to naturally occurring nucleotides.

The term nucleic acid includes any form of DNA or RNA, including, for example, genomic DNA; complementary DNA (cDNA), which is a DNA representation of mRNA, usually obtained by reverse transcription of messenger RNA (mRNA) or by amplification; DNA molecules produced synthetically or by amplification; and mRNA.

The term nucleic acid encompasses double- or triple-stranded nucleic acids, as well as single-stranded molecules. In double- or triple-stranded nucleic acids, the nucleic acid strands need not be coextensive (i.e., a double-stranded nucleic acid need not be double-stranded along the entire length of both strands).

The term nucleic acid also encompasses any chemical modification thereof, such as by methylation and/or by capping. Nucleic acid modifications can include addition of chemical groups that incorporate additional charge, polarizability, hydrogen bonding, electrostatic interaction, and functionality to the individual nucleic acid bases or to the nucleic acid as a whole. Such modifications may include base modifications such as 2'-position sugar modifications, 5-position pyrimidine modifications, 8-position purine modifications, modifications at cytosine exocyclic amines, substitutions of 5-bromo-uracil, backbone modifications, unusual base pairing combinations such as the isobases isocytidine and isoguanidine, and the like.

As used herein the term "target nucleotide sequence" refers to a molecule that includes the nucleotide sequence of a target nucleic acid (e.g., a nucleic acid to be detected in an assay), such as, for example, the amplification product obtained by amplifying a target nucleic acid or the cDNA produced upon reverse transcription of an RNA target nucleic acid.

As used herein, the term "complementary" refers to the capacity for precise pairing between two nucleotides. i.e., if a nucleotide at a given position of a nucleic acid is capable of hydrogen bonding with a nucleotide of another nucleic acid, then the two nucleic acids are considered to be complementary to one another at that position. Complementarity between two single-stranded nucleic acid molecules may be "partial," in which only some of the nucleotides bind, or it may be complete when total complementarity exists between the single-stranded molecules. The degree of complementarity between nucleic acid strands has significant effects on the efficiency and strength of hybridization between nucleic acid strands.

"Specific hybridization" refers to the binding of a nucleic acid to a target nucleotide sequence in the absence of substantial binding to other nucleotide sequences present in the hybridization mixture under defined stringency conditions. Those of skill in the art recognize that relaxing the stringency of the hybridization conditions allows sequence mismatches to be tolerated.

The term "oligonucleotide" is used to refer to a nucleic acid that is relatively short, generally shorter than 200 nucleotides, shorter than 100 nucleotides, in some cases, shorter than 50 nucleotides. Typically, oligonucleotides are single-stranded DNA molecules.

The term "primer" refers to an oligonucleotide that is capable of hybridizing (also termed "annealing") with a nucleic acid and serving as an initiation site for nucleotide (RNA or DNA) polymerization under appropriate conditions (i.e., in the presence of four different nucleoside triphosphates and an agent for polymerization, such as DNA or RNA polymerase or reverse transcriptase) in an appropriate buffer and at a suitable temperature. The appropriate length of a primer depends on the intended use of the primer, but primers are typically at least 7 nucleotides long and, more typically range from 10 to 30 nucleotides, or even more typically from 15 to 30 nucleotides, in length. Other primers can be somewhat longer, e.g., 30 to 50 nucleotides long. In this context, "primer length" refers to the portion of an oligonucleotide or nucleic acid that hybridizes to a complementary "target" sequence and primes nucleotide synthesis. Short primer molecules generally require cooler temperatures to form sufficiently stable hybrid complexes with the template. A primer need not reflect the exact sequence of the template but must be sufficiently complementary to hybridize with a template. The term "primer site" or "primer binding site" refers to the segment of the target nucleic acid to which a primer hybridizes.

A primer is said to anneal to another nucleic acid if the primer, or a portion thereof, hybridizes to a nucleotide sequence within the nucleic acid. The statement that a primer hybridizes to a particular nucleotide sequence is not intended to imply that the primer hybridizes either completely or exclusively to that nucleotide sequence.

The term "primer pair" refers to a set of primers including a 5' "upstream primer" or "forward primer" that hybridizes with the complement of the 5' end of the DNA sequence to be amplified and a 3' "downstream primer" or "reverse primer" that hybridizes with the 3' end of the sequence to be amplified. As will be recognized by those of skill in the art, the terms "upstream" and "downstream" or "forward" and "reverse" are not intended to be limiting, but rather provide illustrative orientation in particular embodiments.

A "probe" is a nucleic acid capable of binding to a target nucleic acid of complementary sequence through one or more types of chemical bonds, generally through complementary base pairing, usually through hydrogen bond formation, thus forming a duplex structure. The probe binds or hybridizes to a "probe binding site." The probe can be labeled with a detectable label to permit facile detection of the probe, and in some cases, once the probe has hybridized to its complementary target. Alternatively, however, the probe may be unlabeled, but may be detectable by specific binding with a ligand that is labeled, either directly or indirectly. Probes can vary significantly in size. Generally, probes are at least 7 to 15 nucleotides in length. Other probes are at least 20, 30, or 40 nucleotides long. Still other probes are somewhat longer, being at least 50, 60, 70, 80, or 90 nucleotides long. Yet other probes are longer still, and are at least 100, 150, 200 or more nucleotides long. Probes can also be of any length that is within any range bounded by any of the above values (e.g., 15-30 nucleotides in length).

The primer or probe can be perfectly complementary to the target nucleic acid sequence or can be less than perfectly complementary. In certain embodiments, the primer has at least 65% identity to the complement of the target nucleic acid sequence over a sequence of at least 7 nucleotides, more typically over a sequence in the range of 10-30 nucleotides, and often over a sequence of at least 14-25 nucleotides, and more often has at least 75% identity, at least 85% identity, at least 90% identity, or at least 95%, 96%, 97%. 98%, or 99% identity. It will be understood that certain bases (e.g., the 3' base of a primer) are generally desirably perfectly complementary to corresponding bases of the target nucleic acid sequence. Primer and probes typically anneal to the target sequence under stringent hybridization conditions.

"Amplification" encompasses any means by which at least a part of at least one target nucleic acid is reproduced, typically in a template-dependent manner, including without limitation, a broad range of techniques for amplifying nucleic acid sequences, either linearly or exponentially. Illustrative means for performing an amplifying step include ligase chain reaction (LCR), ligase detection reaction (LDR), ligation followed by Q-replicase amplification, PCR, primer extension, strand displacement amplification (SDA), hyperbranched strand displacement amplification, multiple displacement amplification (MDA), nucleic acid strand-based amplification (NASBA), two-step multiplexed amplifications, rolling circle amplification (RCA), and the like, including multiplex versions and combinations thereof, for example but not limited to, OLA/PCR, PCR/OLA, LDR/PCR, PCR/PCR/LDR, PCR/LDR, LCR/PCR, PCR/LCR (also known as combined chain reaction-CCR), and the like. Descriptions of such techniques can be found in, among other sources, Ausubel et al.; *PCR Primer: A Laboratory Manual*, Diffenbach, Ed., Cold Spring Harbor Press (1995); *The Electronic Protocol Book, Chang Bioscience* (2002); Msuih et al., J. Clin. Micro. 34:501-07 (1996); The Nucleic Acid Protocols Handbook, R. Rapley, ed., Humana Press, Totowa, N.J. (2002); Abramson et al., *Curr Opin Biotechnol.* 1993 February; 4(1):41-7, U.S. Pat. Nos. 6,027,998; 6,605,451, Barany et al., PCT Publication No. WO 97/31256; Wenz et al., PCT Publication No. WO Publication No. 01/92579; Day et al., Genomics, 29(1): 152-162 (1995), Ehrlich et al., *Science* 252:1643-50 (1991); Innis et al., PCR Protocols: A Guide to Methods and Applications, Academic Press (1990); Favis et al., *Nature Biotechnology* 18:561-64 (2000); and Rabenau et al., *Infection* 28:97-102 (2000); Belgrader, Barany, and Lubin, Development of a Multiplex Ligation Detection Reaction DNA Typing Assay, Sixth International Symposium on Human Identification, 1995 (available on the world wide web at: promega.com/geneticidproc/ussymp6proc/blegrad.html-); LCR Kit Instruction Manual, Cat. #200520, Rev. #050002, Stratagene, 2002; Barany, *Proc. Natl. Acad. Sci. USA* 88:188-93 (1991); Bi and Sambrook, *Nucl. Acids Res.* 25:2924-2951 (1997); Zirvi et al., Nucl. Acid Res. 27:e40i-viii (1999); Dean et al., *Proc Natl Acad Sci USA* 99:5261-66 (2002); Barany and Gelfand, Gene 109:1-11 (1991); Walker et al., *Nucl. Acid Res.* 20:1691-96 (1992); Polstra et al., BMC Inf. Dis. 2:18-(2002); Lage et al., *Genome Res.* 2003 February; 13(2):294-307, and Landegren et al., Science 241:1077-80 (1988), Demidov, V., *Expert Rev Mol Diagn.* 2002 November; 2(6):542-8., Cook et al., *J Microbiol Methods.* 2003 May; 53(2):165-74, Schweitzer et al., *Curr Opin Biotechnol.* 2001 February; 12(1):21-7, U.S. Pat. Nos. 5,830,711, 6,027,889, 5,686,243, PCT Publication Nos. WO 00/56927A3, and WO 98/03673A1.

"Reference level" as used herein refers to an assay or cutoff value that is used to assess diagnostic ("diagnostic" cutoff), prognostic, or therapeutic efficacy and that has been linked or is associated herein with various clinical parameters (e.g., presence of disease such as, for example, to rule a subject as having a disease ("rule in") or rule a subject as not having a disease ("rule out")), stage of disease, severity of disease, progression, non-progression, or improvement of disease, etc.) This disclosure provides exemplary reference levels. However, it is well-known that reference levels may vary depending on the nature of the immunoassay (e.g., such as, in an immunoassay, the antibodies employed, reaction conditions, sample purity, etc.) and that assays can be compared and standardized. It further is well within the ordinary skill of one in the art to adapt the disclosure herein for other assays to obtain assay-specific reference levels for those other immunoassays based on the description provided by this disclosure. Whereas the precise value of the reference level may vary between assays, the findings as described herein should be generally applicable and capable of being extrapolated to other assays.

As used herein the term "single molecule detection" refers to the detection and/or measurement of a single molecule of an analyte in a test sample at very low levels of concentration (such as pg/mL or femtogram/mL levels). A number of different single molecule analyzers or devices are known in the art and include nanopore and nanowell devices. Examples of nanopore devices are described in International Patent Publication No. WO 2016/161402, which is hereby incorporated by reference in its entirety. Examples of nanowell device are described in International Patent Publication No. WO 2016/161400, which is hereby incorporated by reference in its entirety.

A "reagent" refers broadly to any agent used in a reaction, other than the analyte (e.g., nucleic acid or polypeptide being analyzed). Illustrative reagents for a nucleic acid amplification reaction include, but are not limited to, buffer, metal ions, polymerase, reverse transcriptase, primers, template nucleic acid, nucleotides, labels, dyes, nucleases, and the like. Reagents for enzyme reactions include, for example, substrates, cofactors, buffer, metal ions, inhibitors, and activators. Reagents for immunoassay include, for example, antibodies specific for a target marker, detection (e.g., labeled) antibodies, controls, buffers, and the like.

The term "label," as used herein, refers to any atom or molecule that can be used to provide a detectable and/or quantifiable signal. In some cases, the label can be attached, directly or indirectly, to a nucleic acid or protein. Suitable labels that can be attached to probes include, but are not limited to, radioisotopes, fluorophores, chromophores, mass labels, electron dense particles, magnetic particles, spin labels, molecules that emit chemiluminescence, electrochemically active molecules, enzymes, cofactors, and enzyme substrates.

The term "dye," as used herein, generally refers to any organic or inorganic molecule that absorbs electromagnetic radiation at a wavelength greater than or equal 340 nm.

The term "fluorescent dye," as used herein, generally refers to any dye that emits electromagnetic radiation of longer wavelength by a fluorescent mechanism upon irradiation by a source of electromagnetic radiation, such as a lamp, a photodiode, or a laser.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

An "absolute amount" as used herein refers to the absolute value of a change or difference between at least two assay results taken or sampled at different time points and, which similar to a reference level, has been linked or is associated herein with various clinical parameters (e.g., presence of disease, stage of disease, severity of disease, progression, non-progression, or improvement of disease, etc.). "Absolute value" as used herein refers to the magnitude of a real number (such as, for example, the difference between two compared levels (such as levels taken at a first time point and levels taken at a second time point)) without regard to its sign, i.e., regardless of whether it is positive or negative.

This disclosure provides exemplary reference levels and absolute amounts (e.g., calculated by comparing reference levels at different time points). However, it is well-known that reference levels and absolute amounts may vary depending on the nature of the immunoassay (e.g., antibodies employed, reaction conditions, sample purity, etc.) and that assays can be compared and standardized. It further is well within the ordinary skill of one in the art to adapt the disclosure herein for other immunoassays to obtain immunoassay-specific reference levels and absolute amounts for those other immunoassays based on the description provided by this disclosure. Whereas the precise value of the reference level and absolute amount may vary between assays, the findings as described herein should be generally applicable and capable of being extrapolated to other assays.

"Component," "components," or "at least one component," refer generally to a capture antibody, a detection or conjugate a calibrator, a control, a sensitivity panel, a container, a buffer, a diluent, a salt, an enzyme, a co-factor for an enzyme, a detection reagent, a pretreatment reagent/solution, a substrate (e.g., as a solution), a stop solution, and the like that can be included in a kit for assay of a test sample, such as a patient urine, whole blood, serum or plasma sample, in accordance with the methods described herein and other methods known in the art. Some components can be in solution or lyophilized for reconstitution for use in an assay.

"Controls" as used herein generally refers to a reagent whose purpose is to evaluate the performance of a measurement system in order to assure that it continues to produce results within permissible boundaries (e.g., boundaries ranging from measures appropriate for a research use assay on one end to analytic boundaries established by quality specifications for a commercial assay on the other end). To accomplish this, a control should be indicative of patient results and optionally should somehow assess the impact of error on the measurement (e.g., error due to reagent stability, calibrator variability, instrument variability, and the like).

"Correlated to" as used herein refers to compared to.

"Derivative" of an antibody as used herein may refer to an antibody having one or more modifications to its amino acid sequence when compared to a genuine or parent antibody and exhibit a modified domain structure. The derivative may still be able to adopt the typical domain configuration found in native antibodies, as well as an amino acid sequence, which is able to bind to targets (antigens) with specificity. Typical examples of antibody derivatives are antibodies coupled to other polypeptides, rearranged antibody domains, or fragments of antibodies. The derivative may also comprise at least one further compound, e.g., a protein domain, said protein domain being linked by covalent or non-covalent bonds. The linkage can be based on genetic fusion according to the methods known in the art. The additional domain present in the fusion protein comprising the antibody may be linked by a flexible linker, advantageously a peptide linker, wherein said peptide linker comprises plural, hydrophilic, peptide-bonded amino acids of a length sufficient to span the distance between the C-terminal end of the further protein domain and the N-terminal end of the antibody or vice versa. The antibody may be linked to an effector molecule having a conformation suitable for biological activity or selective binding to a solid support, a biologically active substance (e.g., a cytokine or growth hormone), a chemical agent, a peptide, a protein, or a drug, for example.

"Hepatitis B core-related antigen (HBcrAg)" as used herein refers to the antigenic reactivity resulting from denatured hepatitis B e antigen (HBeAg), HBV core antigen (HBcAg) and an artificial core-related protein (p22cr).

"Phosphorylated hepatitis B core antigen", "phosphorylated HBcAg" or P-HBcAg, all used interchangeably herein, all refer to hepatitis B core antigen (HBcAg) that has been phosphorylated at one or more amino acids. For example, a phosphorylated hepatitis B core antigen can have the sequence of SEQ ID NO: 1, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, or SEQ ID NO: 12 provided that the sequence is phosphorylated at one or more amino acids.

"Subject" and "patient" as used herein interchangeably refers to any vertebrate, including, but not limited to, a mammal and a human. In some embodiments, the subject may be a human or a non-human. The subject or patient may be undergoing forms of treatment. "Mammal" as used herein refers to any member of the class Mammalia, including, without limitation, humans and nonhuman primates such as chimpanzees and other apes and monkey species; farm animals such as cattle, sheep, pigs, goats, llamas, camels, and horses; domestic mammals such as dogs and cats; laboratory animals including rodents such as mice, rats, rabbits, guinea pigs, and the like. The term does not denote a particular age or sex. Thus, adult and newborn subjects, as well as fetuses, whether male or female, are intended to be included within the scope of this term.

"Treat," "treating" or "treatment" are each used interchangeably herein to describe reversing, alleviating, or inhibiting the progress of a disease and/or injury, or one or more symptoms of such disease, to which such term applies. Depending on the condition of the subject, the term also refers to preventing a disease, and includes preventing the onset of a disease, or preventing the symptoms associated with a disease. A treatment may be either performed in an acute or chronic way. The acute phase of an HBV infection generally persists from about 4 weeks to about 6 months after infection, while the chronic phase of an HBV infection generally includes the period of time after the acute phase has ended. In some cases, treating or monitoring a chronic HBV infection includes performing an assay on a sample that was obtained from about 24 weeks after the subject was infected. The term also refers to reducing the severity of a disease or symptoms associated with such disease prior to affliction with the disease. Such prevention or reduction of the severity of a disease prior to affliction refers to administration of a pharmaceutical composition to a subject that is not at the time of administration afflicted with the disease. "Preventing" also refers to preventing the recurrence of a disease or of one or more symptoms associated with such disease. "Treatment" and "therapeutically," refer to the act of treating, as "treating" is defined above.

"Variant" is used herein to describe a peptide or polypeptide that differs in amino acid sequence by the insertion, deletion, or conservative substitution of amino acids, but retain at least one biological activity. "SNP" refers to a variant that is a single nucleotide polymorphism. Representative examples of "biological activity" include the ability to be bound by a specific antibody or to promote an immune response. Variant is also used herein to describe a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree, and distribution of charged regions) is recognized in the art as typically involving a minor change. These minor changes can be identified, in part, by considering the hydropathic index of amino acids, as understood in the art. Kyte et al., *J. Mol. Biol.* 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions may be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, including the side chains of those amino acids, as revealed by the hydrophobicity, hydrophilicity, charge, size, and other properties.

"Vector" is used herein to describe a nucleic acid molecule that can transport another nucleic acid to which it has been linked. One type of vector is a "plasmid", which refers to a circular double-stranded DNA loop into which additional DNA segments may be ligated. Another type of vector is a viral vector, wherein additional DNA segments may be ligated into the viral genome. Certain vectors can replicate autonomously in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. "Plasmid" and "vector" may be used interchangeably as the plasmid is the most commonly used form of vector. However, other forms of expression vectors, such as viral vectors (e.g., replication defective retroviruses, adenoviruses and adeno-associated viruses), which serve equivalent functions, can be used. In this regard, RNA versions of vectors (including RNA viral vectors) may also find use in the context of the present disclosure.

Unless otherwise defined herein, scientific and technical terms used in connection with the present disclosure shall have the meanings that are commonly understood by those of ordinary skill in the art. For example, any nomenclatures used in connection with, and techniques of, cell and tissue culture, molecular biology, immunology, microbiology, genetics and protein and nucleic acid chemistry and hybridization described herein are those that are well known and commonly used in the art. The meaning and scope of the terms should be clear; in the event, however of any latent ambiguity, definitions provided herein take precedent over any dictionary or extrinsic definition. Further, unless otherwise required by context, singular terms shall include pluralities and plural terms shall include the singular.

2. Detection of HBcAg and P-HBcAg

In some aspects, the present disclosure relates to assays for determining the presence, level, or status of Hepatitis B core antigen (HBcAg) and/or phosphorylated Hepatitis B core antigen (P-HBcAg) in a sample obtained from a subject. HBcAg and/or P-HBcAg are also referred to herein as "markers" or "protein markers". In some embodiments, the disclosure provide assays for determining the presence or level of HBcAg in a sample obtained from a subject. In some embodiments, the disclosure provides assays for determining the presence or level of P-HBcAg in a sample obtained from a subject. In some embodiments, the disclosure provides assays for determining the presence or level of HBcAg and P-HBcAg in at least one sample obtained from a subject.

In some embodiments, HBcAg and/or P-HBcAg are detected in at least one sample obtained from the subject and one or more additional markers are detected. HBcAg and P-HBcAg are considered to be protein markers. In some embodiments, additional biomarkers described herein that may be detected in addition to HBcAg and/or P-HBcAg are also considered protein markers. For example, additional protein markers include Hepatitis B e-antigen (HBeAg), Hepatitis B surface antigen (HBsAg), an isoform of HBsAg, Hepatitis B core-related antigen (HBcrAg), anti-Hepatitis B surface antigen antibody (anti-HBs), anti-Hepatitis B e-antigen antibody (anti-HBe), anti-Hepatitis surface antigen antibody (anti-HBs), and complexes formed between HBsAg and anti-HBs (also referred to herein as "HBsAg immune complexes"). In some embodiments, the additional markers are enzymatic markers. In some embodiments, the enzymatic markers are selected from AST and ALT. AST and/or ALT are generally detected using enzymatic assays in which the AST or ALT acts on a substrate to generate a detectable product (e.g., colorimetric product). In some embodiments, commercially available products are utilized (e.g., available from Abcam, Cambridge, MA or other sources). In some embodiments, Architect clinical chemistry analysis systems (Abbott, Abbott Park, Ill.) are utilized.

In some embodiments, assays for detection of a protein marker (e.g. HBcAg and/or P-HBcAg) are quantitative or qualitative (e.g., detection of the marker or a specific variant of the marker).

Assays for detection of a protein marker contemplated include immunoassays (such as sandwich and competitive immunoassays), clinical chemistry assays and enzymatic assays. Assays for determining protein markers (e.g. HBcAg and/or P-HBcAg) in a test sample obtained from a subject can comprise the steps of: (a) providing a test sample obtained from a subject; and (b) determining the concentration, presence, or status of one or more markers in the test sample. A specific type of assay that can be performed for determining is an immunoassay. Immunoassays can be conducted using any format known in the art, such as, but not limited to, a sandwich format, a competitive inhibition format (including both forward or reverse competitive inhibition assays) or in a fluorescence polarization format. As mentioned above, the immunoassay is in a sandwich format. Specifically, in one aspect of the present disclosure, at least two antibodies are employed to separate and quantify each of the markers in a test sample. More specifically, the at least two antibodies bind to certain epitopes of the markers forming an immune complex which is referred to as a "sandwich." Generally, in the immunoassays one or more antibodies can be used to capture the marker in the test sample (these antibodies are frequently referred to as a "capture" antibody or "capture" antibodies) and one or more antibodies can be used to bind a detectable (namely, quantifiable) label to the sandwich (these antibodies are frequently referred to as the "detection antibody", "detection antibodies", a "conjugate" or "conjugates"). In a sandwich assay, for example, both antibodies binding to the marker are not diminished by the binding of any other antibody in the assay to its respective binding site. In other words, antibodies should be selected so that the one or more first antibodies brought into contact with a test sample or test sample extract suspected of containing the marker do not bind to all or part of the binding site recognized by the second or subsequent antibodies, thereby interfering with the ability of the one or more second detection antibodies to bind to the marker.

In some embodiments, commercially available antibodies, which are well known in the art, are utilized.

The sample being tested for (for example, suspected of containing) the marker can be contacted with at least one capture antibody (or antibodies) and at least one detection antibody (which is either a second detection antibody or a third detection antibody) either simultaneously or sequentially and in any order. For example, the test sample can be first contacted with at least one capture antibody and then (sequentially) with at least one detection antibody. Alternatively, the test sample can be first contacted with at least one detection antibody and then (sequentially) with at least one capture antibody. In yet another alternative, the test sample can be contacted simultaneously with a capture antibody and a detection antibody.

In the sandwich assay format, a test sample suspected of containing the marker is first brought into contact with an at least one first capture antibody under conditions which allow the formation of a first antibody-marker complex. If more than one capture antibody is used, a first multiple capture antibody-marker complex is formed. In a sandwich assay, the antibodies, such as the at least one capture antibody, are used in molar excess amounts of the maximum amount of marker expected in the test sample.

Optionally, prior to contacting the test sample with the at least one capture antibody (for example, the first capture antibody), the at least one capture antibody can be bound to a solid support or solid phase which facilitates the separation the first antibody-marker from the test sample. Any solid support known in the art can be used, including but not limited to, solid supports made out of polymeric materials in the forms of wells of a reaction tray, test tubes or beads (for example, polystyrene beads, magnetic beads), nitrocellulose strips, membranes, microparticles (for example, latex particles, sheep and DURACYTES® (Abbott Laboratories, Abbott Park, Ill.; DURACYTES® are red blood cells that have been "fixed" by pyruvic aldehyde and formaldehyde)).

The solid phase also can comprise any suitable porous material with sufficient porosity to allow access by detection antibodies and a suitable surface affinity to bind antigens. Microporous structures are generally used, but materials with gel structure in the hydrated state may be used as well. Such useful solid supports include, but are not limited to, nitrocellulose and nylon. Such porous solid supports are in the form of sheets of thickness from about 0.01 to 0.5 mm, including about 0.1 mm. The pore size may vary within wide limits, and can be from about 0.025 to about 15 microns, especially from about 0.15 to about 15 microns. The surface of such supports may be activated by chemical processes which cause covalent linkage of the antigen or antibody to the support. The irreversible binding of the antigen or antibody is obtained, however, in general, by adsorption on the porous material by poorly understood hydrophobic forces.

The antibody (or antibodies) can be bound to the solid support or solid phase by adsorption, by covalent bonding using a chemical coupling agent or by other means known in the art, provided that such binding does not interfere with the ability of the antibody to bind to the marker. Alternatively, the antibody (or antibodies) can be bound with microparticles that have previously coated with streptavidin or biotin (for example, using Power-Bind™-SA-MP streptavidin coated microparticles, available from Seradyn, Indianapolis, Indiana, with antibodies that have been biotinylated using means known in the art). Alternatively, the antibody (or antibodies) can be bound using microparticles that have been previously coated with anti-species specific monoclonal antibodies. Moreover, if necessary, the solid support can be derivatized to allow reactivity with various functional groups on the antibody. Such derivatization requires the use of certain coupling agents such as, but not limited to, maleic anhydride, N-hydroxysuccinimide and 1-ethyl-3-(3-dimethylaminopropyl)carbodiimide.

After the test sample being tested for and/or suspected of containing the marker is brought into contact with the at least one capture antibody (for example, the first capture antibody), the mixture is incubated in order to allow for the formation of a first antibody (or multiple antibody)-marker complex. The incubation can be carried out at a pH of from about 4.5 to about 10.0, at a temperature of from about 2° C. to about 45° C., and for a period from at least about one (1) minute to about eighteen (18) hours, including from about 1 to 20 minutes, also including from about 2-6 minutes. The immunoassay described herein can be conducted in one step (meaning the test sample, at least one capture antibody and at least one detection antibody are all added sequentially or simultaneously to a reaction vessel) or in more than one step, such as two steps, three steps, etc.

After formation of the (first or multiple) capture antibody-marker complex, the complex is then contacted with at least one detection antibody (under conditions which allow for the formation of a (first or multiple) capture antibody-marker-(second or multiple) antibody detection complex). The at least one detection antibody can be the second, third, fourth, etc. antibodies used in the immunoassay. If the capture antibody-complex is contacted with more than one detection antibody, then a (first or multiple) capture antibody-marker detection antibody complex is formed. As with the capture antibody (e.g., the first capture antibody), when the at least second (and subsequent) detection antibody is brought into contact with the capture antibody-marker complex, a period of incubation under conditions similar to those described above is required for the formation of the (first or multiple) capture antibody-marker (second or multiple different markers) detection antibody complex. In some embodiments, at least one detection antibody contains a detectable label. The detectable label can be bound to the at least one detection antibody (e.g., the second detection antibody) prior to, simultaneously with or after the formation of the (first or multiple) capture antibody-marker (second or multiple) detection antibody complex. Any detectable label known in the art can be used. For example, the detectable label can be a radioactive label, such as, $^{3}H$, $^{125}I$, $^{35}S$, $^{14}C$, $^{32}P$, $^{33}P$, an enzymatic label, such as horseradish peroxidase, alkaline phosphatase, glucose 6-phosphate dehydrogenase, etc., a chemiluminescent label, such as, acridinium (e.g., acridium esters, acridinium SPSP (N10-(3-sulfopropyl)-N-(3-sulfopropyl, etc.), luminol, isoluminol, thioesters, sulfonamides, phenanthridinium esters, etc. a fluorescence label, such as, fluorescein (5-fluorescein, 6-carboxyfluorescein, 3'6-carboxyfluorescein, 5(6)-carboxyfluorescein, 6-hexachloro-fluorescein, 6-tetrachlorofluorescein, fluorescein isothiocyanate, etc.), rhodamine, phycobiliproteins, R-phycoerythrin, quantum dots (zinc sulfide-capped cadmium selenide), a thermometric label or an immuno-polymerase chain reaction label. An introduction to labels, labeling procedures and detection of labels is found in Polak and Van Noorden, *Introduction to Immunocytochemistry,* 2$^{nd}$ ed., Springer Verlag, N.Y. (1997) and in Haugland, *Handbook of Fluorescent Probes and Research Chemicals* (1996), which is a combined handbook and catalogue published by Molecular Probes, Inc., Eugene, Oregon.

The detectable label can be bound to the antibodies either directly or through a coupling agent. An example of a coupling agent that can be used is EDAC (1-ethyl-3-(3-dimethylaminopropyl) carbodiimide, hydrochloride) that is commercially available from Sigma-Aldrich, St. Louis, MO. Other coupling agents that can be used are known in the art. Methods for binding a detectable label to an antibody are known in the art. Additionally, many detectable labels can be purchased or synthesized that already contain end groups that facilitate the coupling of the detectable label to the antibody, such as, N10-(3-sulfopropyl)-N-(3-carboxypropyl)-acridinium-9-carboxamide, otherwise known as CPSP-Acridinium Ester or N10-(3-sulfopropyl)-N-(3-sulfopropyl)-acridinium-9-carboxamide, otherwise known as SPSP-Acridinium Ester.

The (first or multiple) capture antibody-marker-(second or multiple) detection antibody complex can be, but does not have to be, separated from the remainder of the test sample prior to quantification of the label. For example, if the at least one capture antibody (e.g., the first capture antibody) is bound to a solid support or solid phase, such as, but not limited to, a well of a reaction tray, a bead or a microparticle, separation can be accomplished by removing the fluid (of the test sample) from contact with the solid support. Alternatively, if the at least first capture antibody is bound to a solid support it can be simultaneously contacted with the marker-containing sample and the at least one second detection antibody to form a first (multiple) antibody-marker antibody complex, followed by removal of the fluid (test sample) from contact with the solid support. If the at least one first capture antibody is not bound to a solid support, then the (first or multiple) capture antibody-marker (second or multiple) detection antibody complex does not have to be removed from the test sample for quantification of the amount of the label.

After formation of the labeled capture antibody-marker complex (e.g., the first capture antibody-marker complex), the amount of label in the complex is quantified using techniques known in the art. For example, if an enzymatic label is used, the labeled complex is reacted with a substrate for the label that gives a quantifiable reaction such as the development of color. If the label is a radioactive label, the label is quantified using a scintillation counter. If the label is a fluorescent label, the label is quantified by stimulating the label with a light of one color (which is known as the "excitation wavelength") and detecting another color (which is known as the "emission wavelength") that is emitted by the label in response to the stimulation. If the label is a chemiluminescent label, the label is quantified detecting the light emitted either visually or by using luminometers, x-ray film, high speed photographic film, a CCD camera, etc. Once the amount of the label in the complex has been quantified, the concentration of marker in the test sample is determined by use of a standard curve that has been generated using serial dilutions of the marker of known concentration. Other than using serial dilutions of the marker, the standard curve can be generated gravimetrically, by mass spectroscopy and by other techniques known in the art.

The methods and kits as described herein encompass other reagents and methods for carrying out the immunoassay. For instance, encompassed are various buffers such as are known in the art and/or which can be readily prepared or optimized to be employed, e.g., for washing, as a conjugate diluent, and/or as a calibrator diluent. An exemplary conjugate diluent is an ARCHITECT® diluent (Abbott Laboratories, Abbott Park, Ill.) containing 2-(N-morpholino)ethanesulfonic acid (MES), another salt, protein blockers, an antimicrobial and detergent. An exemplary calibrator diluent is ARCHITECT® calibrator diluent (Abbott Laboratories, Abbott Park, Ill.), which comprises a buffer containing MES, another salt, a protein blocker and an antimicrobial.

Furthermore, as previously mentioned, the methods and kits optionally are adapted for use on an automated or semi-automated system. Some of the differences between an automated or semi-automated system as compared to a non-automated system (e.g., ELISA) include the substrate to which the capture antibody is attached (which can impact sandwich formation and analyte reactivity), and the length and timing of the capture, detection and/or any optional wash steps. Whereas a non-automated format such as an ELISA may include a relatively longer incubation time with sample and capture reagent (e.g., about 2 hours) an automated or semi-automated format (e.g., ARCHITECT®) may have a relatively shorter incubation time (e.g., approximately 18 minutes for ARCHITECT®). Similarly, whereas a non-automated format such as an ELISA may incubate a detection antibody such as the conjugate reagent (Pb264) for a relatively longer incubation time (e.g., about 2 hours), an automated or semi-automated format (e.g., ARCHITECT®) may have a relatively shorter incubation time (e.g., approximately 4 minutes for the ARCHITECT®).

The markers of the present disclosure (e.g. HBcAg and P-HBcAg) can be used in diagnostic tests to assess, determine, and/or qualify (used interchangeably herein) HBV status in a patient. For example, HBcAg and/or P-HBcAg can be used in diagnostic tests to assess, determine, and/or qualify HBV status in a patient. The phrase "HBV status" includes any distinguishable manifestation of the condition, including not having HBV. For example, HBV status includes, without limitation, the presence or absence of an HBV infection in a patient, the stage or severity of an HBV infection, the progress of an HBV infection (e.g., progress of an HBV infection over time), the effectiveness or response to treatment of an HBV infection (e.g., clinical follow up and surveillance of infection after treatment), and type of HBV infection. Based on this status, further procedures may be indicated, including additional diagnostic tests or therapeutic procedures or regimens.

The power of a diagnostic test to correctly predict status is commonly measured as the sensitivity of the assay, the specificity of the assay or the area under a receiver operated characteristic ("ROC") curve. Sensitivity is the percentage of true positives that are predicted by a test to be positive, while specificity is the percentage of true negatives that are predicted by a test to be negative. A ROC curve provides the sensitivity of a test as a function of 1-specificity. The greater the area under the ROC curve, the more powerful the predictive value of the test. Other useful measures of the utility of a test are positive predictive value and negative predictive value. Positive predictive value is the percentage of people who test positive that are actually positive. Negative predictive value is the percentage of people who test negative that are actually negative.

Analysis of the data described in the present disclosure, as well as clinical data from a cohort of HBV and control patients, resulted in the identification of HBV biomarkers that can be used individually, or in various combinations with each other and with other biomarkers in the form of a panel, to diagnose and/or evaluate an HBV infection in a subject. HBV biomarker panels may include any one of the HBV biomarkers disclosed herein. In some embodiments, an HBV biomarker panel includes HBcAg. In some embodiments, an HBV biomarker panel includes P-HBcAg. In some embodiments, an HBV biomarker panel includes HBcAg and P-HBcAg. HBV biomarker panels can also include non-HBV biomarkers (e.g., assay control biomarkers), and biomarkers previously identified to be associated with HBV. In some embodiments, the biomarker panels of the present disclosure may show a statistical difference in different HBV statuses. Diagnostic tests that use these biomarkers may show an ROC of at least 0.6, at least about 0.7, at least about 0.8, or at least about 0.9.

HBV biomarkers can be differentially present/expressed depending on the type or subclass of HBV (e.g., an HBV signature) and, therefore, panels of more than one HBV biomarker can be useful in aiding in the determination of HBV status. In some embodiments, biomarkers are measured in a patient sample using the methods described herein and compared, for example, to predefined biomarker levels and correlated to HBV status. In some embodiments, the measurement(s) may then be compared with a relevant diagnostic amount(s), cut-off(s), reference levels, or multivariate model scores that distinguish a positive HBV status (e.g., seroconversion) from a negative HBV status (e.g., seroclearance). The diagnostic amount(s) represents a measured amount of a biomarker(s) above which or below which a patient is classified as having a particular HBV status. For example, if the biomarker(s) is/are unfavorable (e.g., increased) as compared to a control subject (e.g., a subject that has not sustained an HBV infection), then a measured amount(s) or levels above the diagnostic cutoff(s) or reference level can provide a diagnosis of HBV. Additionally, if the biomarker(s) is/are present during an HBV infection and not detectable in controls, then any detectably measured amount(s) can provide a diagnosis of an HBV infection. Alternatively, if the biomarker(s) is/are favorable (e.g., decreased) during HBV infection, then a measured amount(s) at or below the diagnostic cutoff(s) or reference level can provide a diagnosis of non-HBV infection. Additionally, if the biomarker(s) is/are not present during an HBV infection and are detectable in controls, then any detectably measured amount(s) can provide a diagnosis of non-HBV infection. As is well understood in the art, by adjusting the particular diagnostic cut-off(s) or reference level(s) used in an assay, one can increase sensitivity or specificity of the diagnostic assay depending on the preference of the diagnostician. In some embodiments, a particular diagnostic cut-off or reference levels can be determined, for example, by measuring the amount of biomarkers in a statistically significant number of samples from patients with the different HBV infection statuses, and drawing the cut-off to suit the desired levels of specificity and sensitivity.

Furthermore, in certain embodiments, the values measured for markers of a biomarker panel are mathematically combined and the combined value is correlated to the underlying diagnostic question. Biomarker values may be combined by any appropriate state of the art mathematical method. Well-known mathematical methods for correlating a marker combination to a disease status employ methods like discriminant analysis (DA) (e.g., linear-, quadratic-, regularized-DA), Discriminant Functional Analysis (DFA), Kernel Methods (e.g., SVM), Multidimensional Scaling (MDS), Nonparametric Methods (e.g., k-Nearest-Neighbor Classifiers), PLS (Partial Least Squares), Tree-Based Methods (e.g., Logic Regression, CART, Random Forest Methods, Boosting/Bagging Methods), Generalized Linear Models (e.g., Logistic Regression), Principal Components based Methods (e.g., SIMCA), Generalized Additive Models, Fuzzy Logic based Methods, Neural Networks and Genetic Algorithms based Methods. The skilled artisan will have no problem in selecting an appropriate method to evaluate a biomarker combination of the present disclosure. In one embodiment of the present disclosure, the method used in a correlating a biomarker combination (e.g. to diagnose HBV status) is selected from DA (e.g., Linear-, Quadratic-, Regularized Discriminant Analysis), DFA, Kernel Methods (e.g., SVM), MDS, Nonparametric Methods (e.g., k-Nearest-Neighbor Classifiers), PLS (Partial Least Squares), Tree-Based Methods (e.g., Logic Regression, CART, Random Forest Methods, Boosting Methods), or Generalized Linear Models (e.g., Logistic Regression), and Principal Components Analysis. Details relating to these statistical methods are found in the following references: Ruczinski et al., 12 *J. OF COMPUTATIONAL AND GRAPHICAL STATISTICS* 475-511 (2003); Friedman, J. H., 84 J. OF *THE AMERICAN STATISTICAL ASSOCIATION* 165-75 (1989); Hastie, Trevor, Tibshirani, Robert, Friedman, Jerome, *The Elements of Statistical Learning*, Springer Series in Statistics (2001); Breiman, L., Friedman, J. H., Olshen, R. A., Stone, C. J. Classification and regression trees, California: Wadsworth (1984); Breiman, L., 45 *MACHINE LEARNING* 5-32 (2001); Pepe, M. S., *The Statistical Evaluation of Medical Tests for Classification and Prediction*, Oxford Statistical Science Series, 28 (2003); and Duda, R. O., Hart, P. E., Stork, D. G., Pattern Classification, Wiley Interscience, 2nd Edition (2001).

3. Monitoring and Treating Chronic HBV Infection

In some embodiments, the presence or level of HBcAg and/or P-HBcAg is used to assess or monitor a stage or phase of chronic HBV infection in a subject. For example, in some embodiments the presence or level of HBcAg and/or P-HBcAg in a sample obtained from a subject diagnosed with HBV is used to assess the stage or phase of chronic HBV infection in the subject. The subject may be diagnosed with and/or receiving treatment for any HBV genotype, including but not limited to HBV genotype A, HBV genotype B, HBV genotype C, HBV genotype D, HBV genotype E, HBV genotype F, HBV genotype G, HBV genotype H, HBV genotype I, or HBV genotype J. In some embodiments, the level of HBcAg and/or P-HBcAg in the sample is determined to be favorable or unfavorable. In some embodiments, an unfavorable level or amount of HBcAg and/or P-HBcAg in the sample indicates that the HBV infection is active in the subject. In some embodiments, an unfavorable level indicates that a treatment for HBV should be provided to the subject. In contrast, a favorable level of amount of HBcAg and/or P-HBcAg in the sample indicates that the HBV infection is improving or inactive in the subject.

In some embodiments, an unfavorable level indicates that the level of HBcAg and/or P-HBcAg is greater than or equal to a threshold level. For example, in some embodiments the stage or phase of HBV infection is determined based upon whether a level or amount of HBcAg in the sample obtained from the subject is greater than or equal to a reference level for HBcAg (e.g. a level in a control sample obtained from a subject not afflicted with HBV). As another example, in some embodiments the stage or phase of HBV infection is determined based upon whether a level or amount of P-HBcAg in the sample obtained from the subject is greater than or equal to a reference level for P-HBcAg (e.g. a level in a control sample obtained from a subject not afflicted with HBV).

In some embodiments, an unfavorable level indicates that the level of HBcAg and/or P-HBcAg has not decreased by at least an absolute amount from a first sample to a second sample obtained at separate time points from the subject. For example, in some embodiments the methods described herein comprise obtaining a first sample from the subject at a first time point before or after receiving a treatment for chronic HBV and obtaining a second sample from the subject at a second time point after the first sample is obtained. An unfavorable level may indicate that the level of HBcAg and/or P-HBcAg in the sample has not decreased by at least an absolute amount from the first time point to the second time point.

In some embodiments a "favorable level" indicates that the level of HBcAg and/or P-HBcAg is less than a threshold level. In some embodiments, a "favorable level" indicates that the level of HBcAg and/or P-HBcAg has decreased by at least an absolute amount from a first sample to a second sample obtained from the subject.

In some embodiments the stage or phase of HBV infection is determined based upon whether a level or amount of HBcAg and/or P-HBcAg in the sample obtained from the subject is greater than or equal to a control level for HBcAg and/or a control level for P-HBcAg (e.g. a level in a control sample obtained from a subject not afflicted with HBV). In some embodiments, the method comprises providing an HBV treatment to the subject.

In some embodiments, one or more additional markers are measured to assess or monitor the stage of phase of HBV infection, including additional protein markers or enzymatic markers as described above.

In some aspects, the methods for assessing and monitoring a stage or phase of chronic HBV infection comprise performing an assay to detect the presence or level of HBcAg and/or P-HBcAg in at least one sample obtained from a subject diagnosed with chronic HBV or receiving a treatment for chronic HBV. In some aspects, the methods further comprise determining the amount of infectious and/or non-infectious HBV particles in the sample. As used herein, the term "infectious HBV particle" refers to an HBV particle containing HBV DNA. In contrast, the terms "non-infectious HBV particle" or "empty HBV particle" are used interchangeably herein to refer to an HBV particle that does not contain HBV DNA. A non-infectious or empty HBV particle may still contain HBV RNA (e.g. pgRNA). In some embodiments, the amount of infectious and/or non-infectious HBV particles in the sample is used to assess the stage of phase of chronic HBV infection in the subject.

As demonstrated in the accompanying drawings and examples, the level of HBcAg is shown herein to correlate with the level of HBV DNA in a given sample. As such, in some embodiments the methods for assessing and monitoring a stage or phase of HBV infection comprise performing an assay to detect the presence or level of HBcAg in at least one sample obtained from a subject, and determining the level or amount of infectious HBV particles in the at least one sample based upon the presence or level of HBcAg. Accordingly, provided herein is a method for assessing and monitoring a stage or phase of HBV infection in a subject that does not require performing a nucleic acid test to measure HBV DNA in a subject. Moreover, this method can be performed regardless of whether the subject has or has not received a treatment for chronic HBV, as the amount of HBcAg is shown herein to correlate with the amount of HBV DNA in a given sample regardless of the treatment status (i.e. regardless of whether a subject has or has not received a treatment for chronic HBV). The methods for assessing and monitoring a stage or phase of HBV infection described herein are thus advantageous in that the method can be performed efficiently and accurately by using a single assay to evaluate the number of infectious HBV particles in a sample, rather than performing one assay for HBcAg and another assay for HBV nucleic acid (e.g. HBV DNA).

As demonstrated in the accompanying drawings and examples, the level of P-HBcAg is shown herein to correlate with the level of HBV DNA or the level of HBV RNA (e.g. HBV pgRNA) in a given sample depending on the subject's treatment status. In particular, the level of P-HBcAg is shown herein to correlate with the level of HBV DNA in a sample obtained from a subject that has not received a treatment for HBV. Accordingly, in some embodiments, the methods for assessing and monitoring a stage or phase of HBV infection comprise performing an assay to detect the presence or level of P-HBcAg in at least one sample obtained from a subject that has not received a treatment for HBV, and determining the amount of infectious HBV particles in the at least one sample based upon the presence or level of P-HBcAg. Accordingly, in some embodiments provided herein is a method for assessing and monitoring a stage or phase of HBV infection in a subject that does not require performing a nucleic acid test to measure HBV DNA in a subject, and thus the method can be performed efficiently and accurately using only a single test rather than separate tests for P-HBcAg and HBV DNA.

In some embodiments, the methods described herein further comprise selecting an appropriate treatment for chronic HBV for the subject. In some embodiments, the methods for assessing and monitoring a stage or phase of chronic HBV infection comprise providing a treatment for chronic HBV to the subject. For example, in some embodiments the methods described herein comprise providing a treatment for chronic HBV to the subject when the level of HBcAg and/or the level of P-HBcAg is determined to be unfavorable. In some embodiments, the methods comprise providing a treatment for chronic HBV to the subject when the amount of infectious HBV particles in the sample is equal to or above a threshold value. In some embodiments, the methods comprise providing a treatment for chronic HBV to the subject when the amount of infectious HBV particles in the same does not decrease by at least an absolute amount from a first sample to a second sample obtained from the subject. Suitable treatments for chronic HBV infection are described herein and include, but are not limited to, nucleos(t)ide analogues (e.g., lamivudine, adefovir, tenofovir, telbivudine, or entecavir), nucleic acids (e.g., an siRNA, an antisense oligonucleotide, an shRNA, or a miRNA), immunomodulators (e.g., interferon alpha-2a or PEGylated interferon alpha-2a), core protein assembly inhibitors (e.g., NVR 3-1983, GLS4, or BAY 41-4109), capsid assembly modulators (CAMs) (e.g. JNJ-632, AT130, or BAY41-4109), HBsAg release inhibitors (e.g., REP 9 AC), entry inhibitors (e.g., Myrcludex-B), DNA modifying agents (e.g. CRISPR-based DNA editing agents, TALENs, ZNFs, and the like) or combinations thereof.

In some embodiments, the presence, level, or status of a marker is used to optimize HBV treatment. For example, if a subject is found to have markers indicative of more virulent or aggressive or drug resistant infection, more aggressive treatment or a different drug may be administered. Conversely, if a subject is found to have markers indicative of a less virulent or aggressive infection, less aggressive treatment or monitoring (e.g., monitoring infections with no specific pharmaceutical treatment) may be chosen.

In some embodiments, the subject is monitored at multiple time points in order to evaluate HBV status. In some embodiments, multiple samples are obtained from the subject at various time points in order to monitor chronic HBV infection in the subject. For example, in some embodiments a first sample is obtained from the subject at a first time point and additional samples are collected every day, every two days every 3 days, every 4 days, every 5 days, every 6 days, every 7 days, ever 2 weeks, every 3 weeks, every 4 weeks, every 5 weeks, every 6 weeks, every 7 weeks, every 8 weeks, every 9 weeks, every 10 weeks, every 11 weeks, every 12 weeks, every 13 weeks, every 14 weeks, every 15 weeks, every 16 weeks, every 5 months, every 6 months, every year, or less frequently in order to continuously monitor a stage or phase of chronic HBV infection in the subject.

In some embodiments, the monitoring is continued and/or repeated until the subject (1) has obtained favorable levels of HBcAg for a sufficient period of time. In some embodiments, the monitoring or determining a treatment method (e.g., detection of markers) is continued and/or repeated until the subject (2) has obtained favorable levels of P-HBcAg for a sufficient period of time. In some embodiments, the monitoring or determining a treatment method (e.g., detection of markers) is continued and/or repeated until the subject (3) has less than a reference amount of infectious HBV particles for a sufficient period of time. In some embodiments, the monitoring or determining a treatment method (e.g., detection of markers) is continued and/or repeated until the subject until two or more of (1)-(3) is accomplished for a sufficient period of time. In some embodiments, the sufficient period of time is a period of about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, about 52 weeks, about 1.5 years, about 2 years, about 2.5 years, about 3.0 years, about 3.5 years, about 4.0 years, about 4.5 years, about 5.0 years, about 5.5. years, about 6.0 years, about 6.5 years, about 7.0 years, about 7.5 years, about 8.0 years, about 8.5 years, about 9.0 years, about 9.5 years, about 10.0 years, about 11.0 years, about 12.0 years, about 13.0 years, about 14.0 years, about 15.0 years, about 16.0 years, about 17.0 years, about 18.0 years, about 19.0 years, or about 20.0 years.

4. Monitoring Response to HBV Treatment

In some embodiments, the assays of the present disclosure can be used to monitor the response of a subject receiving a treatment for HBV. A "treatment for chronic HBV" may also be referred to herein as an "anti-HBV agent", an "HBV therapeutic", an "HBV treatment", "treatment for HBV", "HBV therapy", and the like. By way of example, the assays of the present disclosure can be used to monitor for drug resistance of a subject receiving a treatment for HBV. For example, it is known that the emergence of resistant strains with amino acid substitutions in the tyrosine-methionine-aspartate-aspartate (YMDD) motif of reverse transcriptase can be a serious problem for subjects receiving lamivudine therapy (see, e.g., Hatakeyama, T., et al., *Hepatology,* 45(5): 1179-1186 (2007). The assays of the present disclosure can be used to monitor and/or predict the early emergence of mutants and/or drug resistance during HBV therapy.

In some embodiments, the presence or level of HBcAg and/or P-HBcAg is used to or monitor a response to treatment for chronic HBV infection in the subject. For example, in some embodiments the presence or level of HBcAg and/or P-HBcAg in a sample obtained from a subject diagnosed with chronic HBV is used to monitor responsiveness to a treatment for chronic HBV in the subject.

In some embodiments, the level of HBcAg and/or P-HBcAg in the sample is determined to be favorable or unfavorable. In some embodiments, an unfavorable level or amount of HBcAg and/or P-HBcAg in the sample indicates that a treatment for chronic HBV in the subject is not efficacious. In contrast, a favorable level of amount of HBcAg and/or P-HBcAg in the sample indicates that the treatment for chronic HBV in the subject is efficacious (e.g. the HBV infection is improving).

In some embodiments, an unfavorable level indicates that the level of HBcAg and/or P-HBcAg is greater than or equal to a threshold level. For example, in some embodiments the responsiveness to an HBV treatment is determined based upon whether a level or amount of HBcAg in the sample obtained from the subject is greater than or equal to a reference level for HBcAg (e.g. a level in a control sample obtained from a subject not afflicted with HBV). As another example, in some embodiments the responsiveness to an HBV treatment is determined based upon whether a level or amount of P-HBcAg in the sample obtained from the subject is greater than or equal to a reference level for P-HBcAg (e.g. a level in a control sample obtained from a subject not afflicted with HBV).

In some embodiments, an unfavorable level indicates that the level of HBcAg and/or P-HBcAg has not decreased by at least an absolute amount from a first sample to a second sample obtained at separate time points from the subject. For example, in some embodiments the methods described herein comprise obtaining a first sample from the subject at a first time point before or after receiving a treatment for chronic HBV and obtaining a second sample from the subject at a second time point after the first sample is obtained. The second sample is obtained after the subject has received at least one dose of a treatment for chronic HBV. An unfavorable level may indicate that the level of HBcAg and/or P-HBcAg in the sample has not decreased by at least an absolute amount from the first time point to the second time point In some embodiments a "favorable level" indicates that the level of HBcAg and/or P-HBcAg is less than a threshold level. In some embodiments, a "favorable level" indicates that the level of HBcAg and/or P-HBcAg has decreased by at least an absolute amount from a first sample to a second sample obtained from the subject.

In some embodiments, the second time point is about 1 day to about 1 year after the first time point. In some embodiments, the second time point is more than 1 year after the first time points. In some embodiments, the second time point is about 1 week to about 40 weeks after the first time point. In some embodiments, the second time point is about 10 weeks, about 11 weeks, about 12 weeks, about 13 weeks, or about 14 weeks after the first time point. In some embodiments, the first time point is within 24 hours of receiving a treatment for chronic HBV, and the second time point is about 1 week to about 40 weeks after the first time point. For example, in some embodiments the first time point is within 24 hours of receiving a treatment for chronic HBV, and the second time point is about 10 weeks, about 11 weeks, about 12 weeks, about 13 weeks, or about 14 weeks after the first time point. In some embodiments, the first time point is within 24 hours of receiving a treatment for chronic HBV and the second time point is about 12 weeks (about 3 months) after the first time point.

In some embodiments, one or more additional markers are measured to monitor responsiveness to a treatment for chronic HBV infection in the subject, including additional protein markers or enzymatic markers as described above.

Various HBV treatments differentially effect secretion of HBV-derived particles. HBV particles containing HBV DNA encapsulated within the HBcAg are secreted from infected cells when cccDNA is transcribed to HBV RNA (e.g. pgRNA) and HBV RNA (e.g. pgRNA) is reverse transcribed to HBV DNA (e.g. rcDNA). The use of certain HBV treatments, such as nucleos(t)ide analogues, suppress reverse transcription of HBV RNA into HBV DNA and thereby reduce the amount of HBV particles containing HBV DNA encapsulated within the HBcAg (also referred to herein as "infectious" HBV particles). Accordingly, in some embodiments the methods described herein comprise detecting the presence or amount of HBcAg in a sample obtained from a subject to determine whether a treatment aimed at disrupting the reverse transcription of pgRNA into rcDNA is effective in the subject. For example, in some embodiments the presence or amount of HBcAg in a sample obtained from the subject can be evaluated to determine whether treatment with a nucleos(t)ide analogue is effective. In some embodiments, the presence or amount of P-HBcAg is unaffected by such a treatment, as pgRNA is still translated, and P-HBcAg released from the cell as an "empty" particle (i.e. a particle not containing HBV DNA). These "empty" particles can be detected by measuring phosphorylated HBcAg (P-HBcAg). Additionally, decreasing the level of HBV RNA in a cell can also decrease the level of HBV DNA being produced, as less template RNA is available for reverse transcription. Accordingly, in some embodiments treatments that disrupt the production of HBV RNA (e.g. CAMs) decrease both the amount of P-HBcAg and HBcAg being produced. Therefore, levels of P-HBcAg or levels of P-HBcAg and HBcAg can be obtained in a sample obtained from a subject to evaluate or predict whether such a treatment (e.g. a CAM) is efficacious in the subject.

In some embodiments the methods described herein can be used to evaluate efficacy of a CAM therapeutic in a subject. For example, in some embodiments the methods described herein comprise detecting the presence or amount of P-HBcAg in a sample obtained from a subject receiving treatment with a CAM to determine whether the treatment is efficacious. In some embodiments, the method comprises determining that the treatment is efficacious when the level of P-HBcAg in the sample is less than a reference level of P-HBcAg. In some embodiments, the method comprises determining that the treatment is efficacious when the level of P-HBcAg in the sample is less than a reference level for P-HBcAg and the level of HBcAg in the sample is less than reference level for HBcAg. In some embodiments, the method comprises determining that the treatment is not efficacious when the level of P-HBcAg in the sample is greater than or equal to a reference level of P-HBcAg.

As demonstrated in the accompanying drawings and examples, the amount of HBcAg is shown herein to correlate with the amount of HBV DNA in a given sample after a subject has received a treatment for chronic HBV. As such, in some embodiments the methods for monitoring a response to a treatment for chronic HBV in a subject comprise performing an assay to detect the presence or level of HBcAg in at least one sample obtained from the subject after receiving the treatment, and determining the amount of infectious HBV particles in the at least one sample based upon the presence or level of HBcAg. Accordingly, in some embodiments provided herein is a method for monitoring a response to treatment for chronic HBV infection in a subject that does not require performing a nucleic acid test to measure HBV DNA in order to accurately monitor response to the treatment. The methods for monitoring response to a treatment for chronic HBV infection described herein are thus advantageous in that the method can be performed efficiently and accurately by using a single assay to evaluate the number of infectious HBV particles in a sample, rather than performing one assay for HBcAg and another assay for HBV nucleic acid (e.g. HBV DNA).

As described above, the amount of P-HBcAg is shown herein to correlate with the amount of HBV DNA or the amount of HBV RNA (e.g. HBV pgRNA) in a given sample depending on the subject's treatment status. In some embodiments, the amount of P-HBcAg is shown herein to correlate with the amount of HBV RNA (e.g. pgRNA) in a sample when the subject has received a treatment for HBV. In some embodiments, the treatment disrupts transcription of cccDNA to HBV RNA (e.g. pgRNA). HBV RNA (e.g. pgRNA) is released from the cell in an "empty" particle, otherwise referred to as a "non-infectious" HBV particle. Such particles can be evaluated by determining a level of P-HBcAg in a sample. Therefore, in some embodiments the methods for monitoring a response to a treatment for HBV comprise performing an assay to detect the presence or level of P-HBcAg in at least one sample obtained from a subject that has received a treatment for HBV, and determining the amount of non-infectious HBV particles in the at least one sample based upon the presence or level of P-HBcAg. In some embodiments, the treatment is an agent that disrupts reverse transcription of pgRNA. Suitable treatments include, for example, capsid assembly modulators/inhibitors (CAMs). CAMs inhibit reverse transcription indirectly by preventing the formation of capsids. The reverse transcription of pgRNA takes place inside of capsids. Accordingly, CAMs thus indirectly inhibit reverse transcription. The methods for monitoring a response to a treatment for chronic HBV are thus advantageous in that the method can be performed efficiently and accurately by using a single assay to evaluate the number of non-infectious HBV particles in a sample, rather than performing one assay for P-HBcAg and another assay for HBV nucleic acid (e.g. HBV RNA). In some embodiments, a reduced amount of non-infectious HBV particles indicates that the treatment for HBV (e.g. the CAM) is efficacious in the subject.

In some embodiments, the methods described herein comprise determining an amount of infectious and non-infectious particles in the sample. In some embodiments, the subject has received a treatment that impacts reverse transcription of HBV RNA (e.g. pgRNA) to HBV DNA. For example, some HBV treatments such as nucleoside inhibitors inhibit pgRNA reverse transcription, and therefore reduce the amount of HBV DNA (e.g. infectious particles) released from the cell. However, such HBV treatments do not interfere with the process of transcribing cccDNA to pgRNA, and accordingly these treatments do not reduce the amount of HBV RNA (e.g. pgRNA) secreted from the cell in "empty" or "non-infectious" particles. Therefore, the level of HBcAg (and therefore the amount of infectious particles) should be reduced, whereas the level of P-HBcAg (and therefore the amount of non-infectious particles) should be unaffected by such a treatment.

In some embodiments, the methods for monitoring response to an HBV treatment further comprise determining whether the HBV treatment is efficacious or not efficacious in the subject. In some embodiments, the treatment is determined to be not efficacious when the level of HBcAg and/or P-HBcAg is unfavorable. For example, in some embodiments the treatment is determined to not be efficacious when the level of HBcAg and/or P-HBcAg does not decrease by at least an absolute amount from a first sample to a second sample obtained from the subject.

In some embodiments, the treatment is determined to be not efficacious when the amount of infectious HBV particles is greater than or equal to a threshold value. In some embodiments, the treatment is determined to be not efficacious when the amount of infectious HBV particles does not decrease by at least an absolute amount from a first sample to a second sample collected from the subject. For example, in some embodiments a first sample is collected from the subject at a first time point within 24 hours of receiving a treatment for HBV and a second sample is collected from the subject at a second time point after the first time point. In some embodiments, the second time point is about 10 weeks to about 14 weeks (e.g. about 10 weeks, about 11 weeks, about 12 weeks, about 13 weeks, about 14 weeks) after the first time point. In some embodiments, the treatment is determined to not be efficacious when the amount of infectious HBV particles does not decrease by at least an absolute amount from the first sample to the second sample.

In some embodiments, the treatment is determined to be efficacious when the level of HBcAg and/or P-HBcAg is favorable. In some embodiments, the treatment is determined to be efficacious when the amount of infectious HBV particles decreases by at least an absolute amount from a first sample to a second sample collected from the subject. For example, in some embodiments a first sample is collected from the subject at a first time point within 24 hours of receiving a treatment for HBV and a second sample is collected from the subject at a second time point after the first time point. In some embodiments, the second time point is about 10 weeks to about 14 weeks (e.g. about 10 weeks, about 11 weeks, about 12 weeks, about 13 weeks, about 14 weeks) after the first time point. In some embodiments, the treatment is determined to be efficacious when the amount of infectious HBV particles decreases by at least an absolute amount from the first sample to the second sample.

In some embodiments, the methods for monitoring response to a treatment for chronic HBV in the subject further comprise altering the treatment for chronic HBV when the treatment is determined to not be efficacious. In some embodiments, altering the treatment for chronic HBV comprises providing to the subject an increased dose of the treatment, increasing the frequency of dosing with the treatment, providing to the subject a second treatment, or any combination thereof. For example, in some embodiments altering the HBV treatment comprises providing to the subject an increased dose of the HBV treatment. In some embodiments, altering the treatment comprises increasing the frequency of dosing with the HBV treatment. In some embodiments, altering the treatment comprises increasing the dose and the dosing frequency of the HBV treatment. In some embodiments, altering the treatment comprises providing to the subject a second HBV treatment. The second HBV treatment may comprise any suitable HBV treatment (e.g. HBV therapeutic) described herein. The second HBV treatment may be provided to the subject as an alternative treatment or as an additional treatment. For example, in some embodiments the HBV treatment that the subject was already receiving (e.g. the treatment determined to not be efficacious) is ceased, and a second HBV treatment is given to the subject instead. As another example, in some embodiments the second HBV treatment is given in addition to the HBV treatment that the subject was already receiving. In some embodiments, the second HBV treatment is given in addition to increasing the dose and/or dosing frequency of the HBV treatment that the subject was already receiving.

5. Methods of Measuring HBcAg and/or P-HBcAg

In the methods described above, levels of an HBV biomarker (e.g. HBcAg, P-HBcAg) can be measured by any means, such as antibody dependent methods, such as immunoassays, protein immunoprecipitation, immunoelectrophoresis, chemical analysis, SDS-PAGE and Western blot analysis, protein immunostaining, electrophoresis analysis, a protein assay, a competitive binding assay, a functional protein assay, or chromatography or spectrometry methods, such as high-performance liquid chromatography (HPLC), mass spectrometry, or liquid chromatography-mass spectrometry (LC/MS) or capillary electrophoresis (CE)-MS, or direct infusion, or any separating front end coupled with MS. Also, the assay can be employed in clinical chemistry format such as would be known by one skilled in the art.

a. Immunoassays

In some embodiments, measuring the level of an HBV biomarker includes contacting the sample with a first specific binding member and second specific binding member. In some embodiments the first specific binding member is a capture antibody and the second specific binding member is a detection antibody. In some embodiments, measuring the level of an HBV biomarker includes contacting the sample, either simultaneously or sequentially, in any order: (1) a capture antibody (e.g., an HBV biomarker-capture antibody), which binds to an epitope on an HBV biomarker or an HBV biomarker fragment to form a capture antibody-HBV biomarker antigen complex (e.g., HBV biomarker-capture antibody-HBV biomarker antigen complex), and (2) a detection antibody (e.g., HBV biomarker-detection antibody), which includes a detectable label and binds to an epitope on an HBV biomarker that is not bound by the capture antibody, to form an HBV biomarker antigen-detection antibody complex (e.g., HBV biomarker antigen-HBV biomarker-detection antibody complex), such that a capture antibody-HBV biomarker antigen-detection antibody complex (e.g., HBV biomarker-capture antibody-HBV biomarker antigen-HBV biomarker-detection antibody complex) is formed, and measuring the amount or concentration of an HBV biomarker in the sample based on the signal generated by the detectable label in the capture antibody-HBV biomarker antigen-detection antibody complex.

In some embodiments, the HBV biomarker is HBcAg. In some embodiments, the methods described herein comprise performing an assay to detect the presence, level, or status of HBcAg in at least one sample obtained from a subject. In some embodiments, the biomarker is P-HBcAg. In some embodiments, the methods described herein comprise performing an assay to detect the presence, level, or status of P-HBcAg in at least one sample obtained from a subject. In some embodiments, the presence, level, or status of HBcAg and P-HBcAg are measured in the sample. In some embodiments, the presence, level, or status of HBcAg and P-HBcAg are measured in different samples obtained from the subject. The samples may be obtained at the same time point or at different time points.

In some embodiments, detecting the presence, level, or status of HBcAg in the sample comprises contacting the sample with an antibody that specifically binds to human HBcAg (e.g., an HBcAg capture antibody) to form a capture antibody-HBcAg complex. In some embodiments, the HBcAg capture antibody binds to an epitope on the C-terminus of HBcAg. HBV has been classified phylogenetically into 10 genotypes, A-J. The sequence of human HBcAg genotype A comprises the following amino acids: MDIDPYKEFG ATVELLSFLP SDFFPSVRDL LDTASALYRE ALESPEHCSP HHTALRQAIL CWGELMTLAT WVGNNLEDPA SRDLVVNYVN TNMGLKIRQL LWFHISCLTF GRETVLEYLV SFGVWIRTPP AYRPPNAPIL STLPETTVVR RRDRGRSPRR RTPSPRRRRS QSPRRRRSQS RESQC (SEQ ID NO: 1; FIG. 3). The sequences of HBcAg for HBV genotypes A-J are provided below. Amino acids in bold indicate the C-terminus for each respective sequence.

Genotype A:

(SEQ ID NO: 1)

MDIDPYKEFGATVELLSFLPSDFFPSVRDLLDTASALYREALESPEH

CSPHHTALRQAILCWGELMTLATWVGNNLEDPASRDLVVNYVNTNMG

LKIRQLLWFHISCLTFGRETVLEYLVSFGVWIRTPPAYRPPNAPILS

TLPETTVVRRRDRGRSPRRRTPSPRRRRSQSPRRRRSQSRESQC

Genotype A C-terminus:

(SEQ ID NO: 2)

RRRDRGRSPRRRTPSPRRRRSQSPRRRRSQSRESQC

Genotype A (Amino acids 1-149 of SEQ ID NO: 1):

(SEQ ID NO: 3)

MDIDPYKEFGATVELLSFLPSDFFPSVRDLLDTASALYREALESPEH

CSPHHTALRQAILCWGELMTLATWVGNNLEDPASRDLVVNYVNTNMG

LKIRQLLWFHISCLTFGRETVLEYLVSFGVWIRTPPAYRPPNAPILS

TLPETTVV

Genotype B:

(SEQ ID NO: 4)

MDIDPYKEFGASVELLSFLPSDFFPSIRDLLDTASALYREALESPEH

CSPHHTALRQAILCWGELMNLATWVGSNLEDPASRELVVSYVNVNMG

LKIRQLLWFHISCLTFGRETVLEYLVSFGVWIRTPPAYRPPNAPILS

TLPETTVVRRRGRSPRRRTPSPRRRRSQSPRRRRSQSRESQC

-continued

Genotype B C-terminus:

(SEQ ID NO: 13)

RRRGRSPRRRTPSPRRRRSQSPRRRRSQSRESQC

Genotype C:

(SEQ ID NO: 5)

MDIDPYKEFGASVELLSFLPSDFFPSIRDLLDTASALYREALESPEH

CSPHHTALRQAILCWGELMNLATWVGSNLEDPASRELVVSYVNVNMG

LKIRQLLWFHISCLTFGRETVLEYLVSFGVWIRTPPAYRPPNAPILS

TLPETTVVRRRGRSPRRRTPSPRRRRSQSPRRRRSQSRESQC

Genotype C C-terminus:

(SEQ ID NO: 14)

RRRGRSPRRRTPSPRRRRSQSPRRRRSQSRESQC

Genotype D:

(SEQ ID NO: 6)

MDIDPYKEFGATVELLSFLPSDFFPSVRDLLDTASALYREALESPEH

CSPHHTALRQAILCWGELMTLATWVGGNLEDPASRDLVVSYVNTNMG

LKFRQLLWFHISCLTFGRETVIEYLVSFGVWIRTPPAYRPPNAPILS

TLPETTVVRRRGRSPRRRTPSPRRRRSQSPRRRRSQSRESQC

Genotype D C-terminus:

(SEQ ID NO: 15)

RRRGRSPRRRTPSPRRRRSQSPRRRRSQSRESQC

Genotype E:

(SEQ ID NO: 7)

MDIDPYKEFGATVELLSFLPSDFFPSVRDLLDTASALYRDALESPEH

CSPHHTALRQAILCWGELMTLATWVGVNLEDPASRDLVVSYVNTNMG

LKFRQLLWFHISCLTFGRETVIEYLVSFGVWIRTPPAYRPPNAPILS

TLPENTVVRRRGRSPRRRTPSPRRRRSQSPRRRRSQSPASQC

Genotype E C-terminus:

(SEQ ID NO: 16)

RRRGRSPRRRTPSPRRRRSQSPRRRRSQSPASQC

Genotype F:

(SEQ ID NO: 8)

MDIDPYKEFGASVELLSFLPSDFFPSVRDLLDTASALYRDALESPEH

CTPNHTALRQAILCWGELMTLASWVGNNLEDPAARDLVVNYVNTNMG

LKIRQLLWFHISCLTFGRETVLEYLVSFGVWIRTPPAYRPPNAPILS

TLPETTVVRRRGRSPRRRTPSPRRRRSQSPRRRRSQSPASQC

Genotype F C-terminus:

(SEQ ID NO: 17)

RRRGRSPRRRTPSPRRRRSQSPRRRRSQSPASQC

Genotype G:

(SEQ ID NO: 9)

MDRTTLPYGLFGLDIDPYKEFGATVELLSFLPSDFFPSVRDLLDTAS

ALYRESLESSDHCSPHHTALRQAILCWGELMTLATWVGNNLEDPASR

DLVVNYVNTNMGLKIRQLLWFHISCLTFGRETVLEYLVSFGVWIRTP

PAYRPPNAPILSTLPETTVVRRRGRSPRRRTPSPRRRRSQSPRRRRS

ASPASQC

Genotype G C-terminus:

(SEQ ID NO: 18)

RRRGRSPRRRTPSPRRRRSQSPRRRRSASPASQC

-continued

Genotype H:

(SEQ ID NO: 10)

MDIDPYKEFGASVELLSFLPSDFFPSVRDLLDTASALYRDALESPEH

CTPNHTALRQAILCWGELMTLASWVGNNLEDPAARDLVVNYVNTNMG

LKIRQLLWFHISCLTFGRETVLEYLVSFGVWIRTPPAYRPPNAPILS

TLPETTVVRQRGRAPRRRTPSPRRRRSQSPRRRRSQSPASQC

Genotype H C-terminus:

(SEQ ID NO: 19)

RQRGRAPRRRTPSPRRRRSQSPRRRRSQSPASQC

Genotype I:

(SEQ ID NO: 11)

MDIDPYKEFGASVELLSFLPSDFFPSIRDLLDTASALYREALESPEH

CSPHHTALRQAIVCWGELMNLATWVGSNLEDPASRELVVSYVNVNMG

LKIRQLLWFHISCLTFGRETVLEYLVSFGVWIRTPPAYRPPNAPILS

TLPETTVVRRRGRSPRRRTPSPRRRRSQSPRRRRSQSRESQC

Genotype I C-terminus:

(SEQ ID NO: 20)

RRRGRSPRRRTPSPRRRRSQSPRRRRSQSRESQC

Genotype J:

(SEQ ID NO: 12)

MDIDPYKEFGASVELLSFLPSDFFPSIRDLLDTASALYREALESPEH

CSPHHTALRQAVLCWGELMNLATWVGSNLEDPASRELVVSYVNINMG

LKIRQLLWFHISCLTFGRETVLEYLVSFGVWIRTPPAYRPPNAPILS

TLPETTVVRRRGRSPRRRTPSPRRRRSQSPRRRRSQSPSSQC

Genotype J C-terminus:

(SEQ ID NO: 21)

RRRGRSPRRRTPSPRRRRSQSPRRRRSQSPSSQC

The below table contains consensus sequences for the above HBcAg, including genotypes A-J.

| Sequence | Consensus sequence |
|---|---|
| HbcAg | MDIDPYKEFGAsVELLS-FLPSDFFPSiRDLLDTAS<br>ALYReALESPEHCSPHHTALRQAILCWGELM-nLAT<br>WVGsNLEDPaSReLVVsYVNvNMGLKiRQLLWFHIS<br>CLTFGRETVlEYLVSFGVWIRTPpAYRPPNAPILST<br>LPETTVVRRR---GRSPR-rRTPSPRRRRSQSPRRR<br>RSQSRe-SQC (SEQ ID NO: 22) |
| HbcAg-<br>C-terminus | RRR---GRSPR-rRTPSPRRRRSQSPRRRRSQSRe-<br>SQC (SEQ ID NO: 23) |
| Genotype<br>A | MDIDPYKEFGATVELLSFLPSDFFPSVRDLLDTASA<br>LYREALESPEHCSPHHTALRQAILCWGELM-TLATW<br>VGNNLeDPASRDLVVNYVNTNMGLKIRQLLWFHISC<br>LTFGRETVLEYLVSFGVWIRTPPAYRPPNAPILSTL<br>PETTVVRRRDR-GRSPRRRTPSPRRRRSQSPRRRRS<br>QSRESQCgp- (SEQ ID NO: 24) |
| Genotype<br>A-<br>C-terminus | RRRDR-GRSPRRRTPSPRRRRSQSPRRRRSQSRESQ<br>Cgp- (SEQ ID NO: 25) |
| Genotype<br>B | MDIDpYKEFGASVELLSF-LPSDFFPSIRDLLDTAS<br>ALYREALESPEHCSPHHTALRQAIlCWGELMNLATW<br>VGSNLEDPASRELVVsYVNVNMGLKiRQLLWFHISC<br>LTFGRETVLEYLVSFGVWIRTPpAYRPpNAPILSTL<br>PETTVVRRRGRSPRRRTPSPRRRRSQSPRRRRSQSR<br>E-SQC (SEQ ID NO: 26)_ |
| Genotype<br>B-<br>C-terminus | RRRGRSPRRRTPSPRRRRSQSPRRRRSQSRE-SQC<br>(SEQ ID NO: 27) |

-continued

| Sequence | Consensus sequence |
|---|---|
| Genotype C | MDIDPYKEFGASVELLS-FLPSDFFPSIRDLLDTAS ALYREALESPEHCSPHHTALRQAILCWGELMNLATW VGSNLEDPASRELVVsYVNVNMGLKiRQlLWFHISC LTFGRETVLEYLVSFGVWIRTPpAYRPPNAPILSTL PETTVVRRRGRSPRRRTPSPRRRRSQSPRRRRSQSR ESQC (SEQ ID NO: 28) |
| Genotype C-C-terminus | RRRGRSPRRRTPSPRRRRSQSPRRRRSQSRESQC (SEQ ID NO: 29) |
| Genotype D | MDIDPYKEFGAtVELLSFLPsDFFPSVRDLLDTASA LYReALESPEHCsPHHTALRQAILCWGeLMtLATWV GgNLEDPaSRDLVVSYVNTNmGLKFRQLLWFHISCL TFGReTViEYLVSFGVWIRTPpAYRPPNAPILSTLP ETTVvRRRG--RSPRR-RTPSPRRRRSQSPRRRRSQ SREs-QC (SEQ ID NO: 30) |
| Genotype D-C-terminus | RRRG--RSPRR-RTPSPRRRRSQSPRRRRSQSREs-QC (SEQ ID NO: 31) |
| Genotype E | MDIDPYKEFGAtVELLSFLPSDFFPSVRDLLDTASA LYRDALESPEHCSPHHTALRQAILCWGeLMtLATWV GvNLEDPASRDLVVSYVNTNMGLKFRQLLWFHISCL TFGRETViEYLVSFGVWIRTPPAYRPPNAPILSTLP EnTVVRRR--GRSPRRRTPSPRRRRSQSPRRRRSQ S-pasQC (SEQ ID NO: 32) |
| Genotype E-C-terminus | RRR--GRSPRRRTPSPRRRRSQSPRRRRSQS-pasQ C (SEQ ID NO: 33) |
| Genotype F | MDIDPYKEFGASVELLSFLPSDFFPSVRDLLDTASA LYRDALESPEHCTPnHTALRQAILCWGELMTLASWV GNNLEDPAARDLVVNYVNTnMGLKIRQLLWFHISCL TFGRETVLEYLVSFGVWIRTPPAYRPPNAPILSTLP ETTVVRRRGRSPRRRTPSPRRRRSQSPRRRRSQSPA SQC (SEQ ID NO: 34) |
| Genotype F-C-terminus | RRRGRSPRRRTPSPRRRRSQSPRRRRSQSPASQC (SEQ ID NO: 35) |
| Genotype G | LDIDPYKEFGATVELLSFLPSDFFPSVRDLLDTASA LYRESLESSDHCSPHHTALRQAILCWGELMTLATWV GNNLEDPASRDLVVNYVNTNMGLKIRQLLWFHISCL TFGRETVLEYLVSFGVWIRTPPAYRPPNAPILSTLP ETTVVRRRGRSPRRRTPSPRRRRSQSPRRRRSASPA SQC (SEQ ID NO: 36) |
| Genotype G-C-terminus | RRRGRSPRRRTPSPRRRRSQSPRRRRSASPASQC (SEQ ID NO: 37) |
| Genotype H | MDIDPYKEFGASVELLSFLPSDFFPSVRDLLDTASA LYRDALESPEHCTPnHTALRQAILCWGELMTLASWV GNNLEDPAARDLVVNYVNTNMGLKIRQLLWFHISCL TFGRETVLEYLVSFGVWIRTPPAYRPPNAPILSTLP ETTVvRQRGRAPRRRTPSPRRRRSQSPRRRRSQSPA SQC (SEQ ID NO: 38) |
| Genotype H-C-terminus | RQRGRAPRRRTPSPRRRRSQSPRRRRSQSPASQC (SEQ ID NO: 39) |
| Genotype I | MDIDPYKEFGASVELLSFLPSDFFPSIRDLLDTASA LYREALESPEHCSPHHTALRQAIVCWGELMNLATWV GSNLEDPASRELVVSYVNVNMGLKIRQLLWFHISCL TFGRETVLEYLVSFGVWIRTPPAYRPPNAPILSTLP ETTVVRRRGRSPRRRTPSPRRRRSQSPRRRRSQSRE SQC (SEQ ID NO: 40) |

The methods described herein can be used to detect HBcAg or phosphorylated HbcAg for any one of the above-described HBV genotypes (e.g. HBV genotype A, HBV genotype B, HBV genotype C, HBV genotype D, HBV genotype E, HBV genotype F, HBV genotype G, HBV genotype H, HBV genotype I, or HBV genotype J).

In some embodiments, the methods described herein comprise contacting a sample with an HbcAg capture antibody that binds to an epitope on SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38 or SEQ ID NO:40. In some embodiments, the methods comprise contacting a sample with an HbcAg capture antibody that binds to an epitope on the C-terminus of SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, or SEQ ID NO: 40. In rare cases, some patients afflicted with one of the above-described genotypes express an HbcAg having one or more mutations compared to the sequences described above. Accordingly, in some embodiments the methods comprise contacting a sample with a capture antibody and/or a detection antibody that binds to an epitope having at least 95% sequence identity with an amino acid sequence provided herein. In some embodiments, the methods comprise contacting a sample with an HbcAg capture antibody that binds to an epitope on the C-terminus of an amino acid sequence having at least 95% sequence identity to SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, or SEQ ID NO: 40. In some embodiments the methods comprise contacting a sample with an HBcAg capture antibody that binds to an epitope on SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37 or SEQ ID NO: 39. In some embodiments, the HbcAg capture antibody binds to an epitope of about 3 to about 36 amino acids (e.g., contiguous amino acids) in length. In some embodiments, the HbcAg capture antibody binds to an epitope of about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, or about 36 contiguous amino acids in length.

In yet further embodiments, the methods described herein comprise contacting a sample with an HbcAg capture antibody that binds to an epitope on SEQ ID NO: 1, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, or SEQ ID NO: 12. In some embodiments, the methods comprise contacting a sample with an HbcAg capture antibody that binds to an epitope on the C-terminus of SEQ ID NO: 1, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, or SEQ ID NO: 12. In rare cases, some patients afflicted with one of the above-described genotypes express an HbcAg having one or more mutations compared to the sequences described above. Accordingly, in some embodiments the methods comprise contacting a sample with a capture antibody and/or a detection antibody that binds to an epitope having at least 95% sequence identity with an amino acid sequence provided herein. In some embodiments, the methods comprise contacting a sample with an HbcAg capture antibody that binds to an epitope on the C-terminus of an amino acid sequence having at least 95% sequence identity to SEQ ID NO: 1, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, or SEQ ID NO: 12. In some embodiments the methods comprise contacting a sample with an HbcAg capture antibody that binds to an epitope on SEQ ID NO: 2, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, or SEQ ID NO: 21. In some embodiments, the HbcAg capture antibody binds to an epitope of about 3 to about 36 amino acids (e.g., contiguous amino acids) in length. In some embodiments, the HbcAg capture antibody binds to an epitope of about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, or about 36 contiguous amino acids in length.

In some embodiments, the HbcAg capture antibody binds to an epitope of about 3 to about 36 contiguous amino acids in length on SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37 or SEQ ID NO: 39. In some embodiments, the HbcAg capture antibody binds to an epitope of about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, or about 36 contiguous amino acids on SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37 or SEQ ID NO: 39. In some embodiments, the HbcAg capture antibody binds to non-contiguous epitopes on the C-terminus of HbcAg. For example, in some embodiments, the HbcAg capture antibody binds to multiple binding sites on SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37 or SEQ ID NO: 39, wherein each binding site comprises at least three contiguous amino acids (e.g. at least 3, at least 4, at least 5, at least 6, at least 7 contiguous amino acids) and wherein each binding site is separated by at least one (e.g. at least one, at least two, at least three) amino acid.

In yet still further embodiments, the HbcAg capture antibody binds to an epitope of about 3 to about 36 contiguous amino acids in length on SEQ ID NO: 2, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, or SEQ ID NO: 21. In some embodiments, the HbcAg capture antibody binds to an epitope of about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, or about 36 contiguous amino acids on SEQ ID NO: 2, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, or SEQ ID NO: 21. In some embodiments, the HbcAg capture antibody binds to non-contiguous epitopes on the C-terminus of HbcAg. For example, in some embodiments, the HbcAg capture antibody binds to multiple binding sites on SEQ ID NO: 2, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, or SEQ ID NO: 21, wherein each binding site comprises at least three contiguous amino acids (e.g. at least 3, at least 4, at least 5, at least 6, at least 7 contiguous amino acids) and wherein each binding site is separated by at least one (e.g. at least one, at least two, at least three) amino acid.

The C-terminus of human HbcAg genotype A is represented by amino acids 150-185 of SEQ ID NO: 1. Amino acids 150-185 of SEQ ID NO: 1 are represented by SEQ ID NO: 2. In some embodiments, the HbcAg capture antibody binds to an epitope of about 3 to about 36 amino acids (e.g., contiguous amino acids) in length on SEQ ID NO: 2 or the consensus sequence represented by SEQ ID NO:25. In some embodiments, the HbcAg capture antibody binds to an epitope of about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, or about 36 contiguous amino acids on SEQ ID NO: 2 or SEQ ID NO:25. In some embodiments, the HbcAg capture antibody binds to multiple binding sites on SEQ ID NO: 2 or SEQ ID NO:25, wherein each binding site comprises at least three contiguous amino acids (e.g. at least 3, at least 4, at least 5, at least 6, at least 7 contiguous amino acids) and wherein each binding site is separated by at least one (e.g. at least one, at least two, at least three) amino acid.

In some embodiments, detecting the presence, level, or status of HbcAg in the sample further comprises contacting the sample with a detection antibody that binds to an epitope on HbcAg that is not bound by the HbcAg capture antibody, thus forming a capture antibody-HbcAg-detection antibody complex. In some embodiments, the HbcAg detection antibody binds to an epitope contained within SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, or SEQ ID NO: 40. In some embodiments, the HbcAg detection antibody binds to an epitope contained within an amino acid sequence having at least 95% sequence identity with SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, or SEQ ID NO: 40. In some embodiments, the HbcAg detection antibody binds to an epitope of about 3 to about 50 contiguous amino acids (about 3 to about 40 contiguous amino acids, about 3 to about 35 contiguous amino acids, about 3 to about 30 contiguous amino acids, about 3 to about 25 contiguous amino acids, about 3 to about 20 contiguous amino acids, or about 3 to about 15 contiguous amino acids).

In yet still further embodiments, detecting the presence, level, or status of HbcAg in the sample further comprises contacting the sample with a detection antibody that binds to an epitope on HbcAg that is not bound by the HbcAg capture antibody, thus forming a capture antibody-HbcAg-detection antibody complex. In some embodiments, the HbcAg detection antibody binds to an epitope contained within amino acids 1-149 of SEQ ID NO: 1, SEQ ID NO: 4, SEQ ID NO: 5, SEQ ID NO: 6, SEQ ID NO: 7, SEQ ID NO: 8, SEQ ID NO: 10, SEQ ID NO: 11, or SEQ ID NO: 12. In some embodiments, the HbcAg detection antibody binds to an epitope contained within amino acids 1-149 of an amino acid sequence having at least 95% sequence identity with SEQ ID NO: 1, SEQ ID NO: 4, SEQ ID NO: 5, SEQ ID NO: 6, SEQ ID NO: 7, SEQ ID NO: 8, SEQ ID NO: 10, SEQ ID NO: 11, or SEQ ID NO: 12. In some embodiments, the HbcAg detection antibody binds to an epitope contained within amino acids 1-161 of SEQ ID NO: 9. In some embodiments, the HbcAg detection antibody binds to an epitope contained within amino acids 1-161 of an amino acid sequence having at last 95% sequence identity with SEQ ID NO: 9. In some embodiments, the HbcAg detection antibody binds to an epitope of about 3 to about 50 contiguous amino acids (about 3 to about 40 contiguous amino acids, about 3 to about 35 contiguous amino acids, about 3 to about 30 contiguous amino acids, about 3 to about 25 contiguous amino acids, about 3 to about 20 contiguous amino acids, or about 3 to about 15 contiguous amino acids).

In some embodiments, the HbcAg detection antibody binds to an epitope of about 3 to about 50 contiguous amino acids (about 3 to about 40 contiguous amino acids, about 3 to about 35 contiguous amino acids, about 3 to about 30 contiguous amino acids, about 3 to about 25 contiguous amino acids, about 3 to about 20 contiguous amino acids, or about 3 to about 15 contiguous amino acids) within SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, or SEQ ID NO: 40. In some embodiments, the HbcAg detection antibody binds to non-contiguous epitopes. In some embodiments, the HbcAg detection antibody binds to non-contiguous epitopes on SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, or SEQ ID NO: 40. In some embodiments the HbcAg detection antibody binds to more multiple binding sites, and each binding site is separated by at least 2 amino acids. For example, in some embodiments the HbcAg detection antibody binds to multiple binding sites, wherein each binding site comprises at least 2 contiguous amino acids and wherein each binding site is separated by at least 2 amino acids. In some embodiments, each binding site comprises at least 2 contiguous amino acids (e.g. at least 2, at least 3, at least 4, at least 5, at least 6, at least 7, at least 8, at least 9, or at least 10 amino acids) and each binding site is separated by at least 10 amino acids. In some embodiments, each binding site is separated by at least 20 amino acids (e.g. at least 20, at least 25, at least 30, at least 35, at least 40, at least 45, at least 50 amino acids).

In yet further embodiments, the HbcAg detection antibody binds to an epitope of about 3 to about 50 contiguous amino acids (about 3 to about 40 contiguous amino acids, about 3 to about 35 contiguous amino acids, about 3 to about 30 contiguous amino acids, about 3 to about 25 contiguous amino acids, about 3 to about 20 contiguous amino acids, or about 3 to about 15 contiguous amino acids) within amino acids 1-149 of SEQ ID NO: 1, SEQ ID NO: 4, SEQ ID NO: 5, SEQ ID NO: 6, SEQ ID NO: 7, SEQ ID NO: 8, SEQ ID NO: 10, SEQ ID NO: 11, or SEQ ID NO: 12, or within amino acids 1-161 of SEQ ID NO: 9. In some embodiments, the HbcAg detection antibody binds to non-contiguous epitopes. In some embodiments, the HbcAg detection antibody binds to non-contiguous epitopes on SEQ ID NO: 1, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, or SEQ ID NO: 12. In some embodiments the HbcAg detection antibody binds to more multiple binding sites, and each binding site is separated by at least 2 amino acids. For example, in some embodiments the HbcAg detection antibody binds to multiple binding sites, wherein each binding site comprises at least 2 contiguous amino acids and wherein each binding site is separated by at least 2 amino acids. In some embodiments, each binding site comprises at least 2 contiguous amino acids (e.g. at least 2, at least 3, at least 4, at least 5, at least 6, at least 7, at least 8, at least 9, or at least 10 amino acids) and each binding site is separated by at least 10 amino acids. In some embodiments, each binding site is separated by at least 20 amino acids (e.g. at least 20, at least 25, at least 30, at least 35, at least 40, at least 45, at least 50 amino acids).

In still other aspects, the detection antibody binds to an epitope contained within amino acids 1-149 of SEQ ID NO: 1. Amino acids 1-149 of SEQ ID NO: 1 are represented by SEQ ID NO: 3. In some embodiments, the HbcAg detection antibody binds to an epitope of about 3 to about 50 amino acids on SEQ ID NO: 3. In some embodiments, the HbcAg detection antibody binds to an epitope of about 3 to about 50 contiguous amino acids on SEQ ID NO: 3 In some embodiments, the detection antibody binds to an epitope of about 3 to about 40 contiguous amino acids, about 3 to about 35 contiguous amino acids, about 3 to about 30 contiguous amino acids, about 3 to about 25 contiguous amino acids, about 3 to about 20 contiguous amino acids, or about 3 to about 15 contiguous amino acids on SEQ ID NO: 3. In some embodiments, the HbcAg detection antibody binds to an epitope of about 3 to about 15 amino acids (e.g., contiguous amino acids) on SEQ ID NO: 3 For example, in some embodiments, the HbcAg detection antibody binds to an epitope of about 3, about 4, about 5, about 6, about 7, about 8, about 9, about 10, about 11, about 12, about 13, about 14, or about 15 contiguous amino acids on SEQ ID NO: 3. In some embodiments, the HbcAg detection antibody binds to non-contiguous epitopes on SEQ ID NO: 3. For example, in some embodiments the HbcAg detection antibody binds to more multiple binding sites, and each binding site is separated by at least 2 amino acids. For example, in some embodiments the HbcAg detection antibody binds to multiple binding sites, wherein each binding site comprises at least 2 contiguous amino acids and wherein each binding site is separated by at least 2 amino acids. In some embodiments, each binding site comprises at least 2 contiguous amino acids (e.g. at least 2, at least 3, at least 4, at least 5, at least 6, at least 7, at least 8, at least 9, or at least 10 amino acids) and each binding site is separated by at least 10 amino acids. In some embodiments, each binding site is separated by at least 20 amino acids (e.g. at least 20, at least 25, at least 30, at least 35, at least 40, at least 45, at least 50 amino acids).

In some embodiments, the HbcAg capture antibody binds to an epitope on HbcAg other than the C-terminus. In some embodiments, the HbcAg capture antibody binds to an epitope contained within SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, or SEQ ID NO: 40. In some embodiments, the HbcAg capture antibody binds to an epitope contained within SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, or SEQ ID NO: 40. In some embodiments, the HbcAg capture antibody binds to an epitope of about 3 to about 50 contiguous amino acids (about 3 to about 40 contiguous amino acids, about 3 to about 35 contiguous amino acids, about 3 to about 30 contiguous amino acids, about 3 to about 25 contiguous amino acids, about 3 to about 20 contiguous amino acids, or about 3 to about 15 contiguous amino acids).

In yet still other embodiments, the HbcAg capture antibody binds to an epitope on HbcAg other than the C-terminus. In some embodiments, the HbcAg capture antibody binds to an epitope contained within amino acids 1-149 of SEQ ID NO: 1, SEQ ID NO: 4, SEQ ID NO: 5, SEQ ID NO: 6, SEQ ID NO: 7, SEQ ID NO: 8, SEQ ID NO: 10, SEQ ID NO: 11, or SEQ ID NO: 12. In some embodiments, the HbcAg capture antibody binds to an epitope contained within amino acids 1-161 of SEQ ID NO: 9. In some embodiments, the HbcAg capture antibody binds to an epitope contained within amino acids 1-149 of an amino acid sequence having at least 95% sequence identity with SEQ ID NO: 1, SEQ ID NO: 4, SEQ ID NO: 5, SEQ ID NO: 6, SEQ ID NO: 7, SEQ ID NO: 8, SEQ ID NO: 10, SEQ ID NO: 11, or SEQ ID NO: 12. In some embodiments, the HbcAg capture antibody binds to an epitope contained within amino acids 1-161 of an amino acid sequence having at least 95% sequence identity with SEQ ID NO: 9. In some embodiments, the HbcAg capture antibody binds to an epitope of about 3 to about 50 contiguous amino acids (about 3 to about 40 contiguous amino acids, about 3 to about 35 contiguous amino acids, about 3 to about 30 contiguous amino acids, about 3 to about 25 contiguous amino acids, about 3 to about 20 contiguous amino acids, or about 3 to about 15 contiguous amino acids).

In some embodiments, the HbcAg capture antibody binds to an epitope of about 3 to about 50 contiguous amino acids (about 3 to about 40 contiguous amino acids, about 3 to about 35 contiguous amino acids, about 3 to about 30 contiguous amino acids, about 3 to about 25 contiguous amino acids, about 3 to about 20 contiguous amino acids, or about 3 to about 15 contiguous amino acids) within SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, or SEQ ID NO: 40. In some embodiments, the HbcAg capture antibody binds to non-contiguous epitopes. In some embodiments, the HbcAg capture antibody binds to non-contiguous epitopes on SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, or SEQ ID NO: 40. In some embodiments the HbcAg capture antibody binds to more multiple binding sites, and each binding site is separated by at least 2 amino acids. For example, in some embodiments the HbcAg capture antibody binds to multiple binding sites, wherein each binding site comprises at least 2 contiguous amino acids and wherein each binding site is separated by at least 2 amino acids. In some embodiments, each binding site comprises at least 2 contiguous amino acids (e.g. at least 2, at least 3, at least 4, at least 5, at least 6, at least 7, at least 8, at least 9, or at least 10 amino acids) and each binding site is separated by at least 10 amino acids. In some embodiments, each binding site is separated by at least 20 amino acids (e.g. at least 20, at least 25, at least 30, at least 35, at least 40, at least 45, at least 50 amino acids).

In still other embodiments, the HbcAg capture antibody binds to an epitope of about 3 to about 50 contiguous amino acids (about 3 to about 40 contiguous amino acids, about 3 to about 35 contiguous amino acids, about 3 to about 30 contiguous amino acids, about 3 to about 25 contiguous amino acids, about 3 to about 20 contiguous amino acids, or about 3 to about 15 contiguous amino acids) within amino acids 1-149 of SEQ ID NO: 1, SEQ ID NO: 4, SEQ ID NO: 5, SEQ ID NO: 6, SEQ ID NO: 7, SEQ ID NO: 8, SEQ ID NO: 10, SEQ ID NO: 11, or SEQ ID NO: 12, or within amino acids 1-161 of SEQ ID NO: 9. In some embodiments, the HBcAg capture antibody binds to non-contiguous epitopes. In some embodiments, the HbcAg capture antibody binds to non-contiguous epitopes on SEQ ID NO: 1, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, or SEQ ID NO: 12. In some embodiments the HbcAg capture antibody binds to more multiple binding sites, and each binding site is separated by at least 2 amino acids. For example, in some embodiments the HbcAg capture antibody binds to multiple binding sites, wherein each binding site comprises at least 2 contiguous amino acids and wherein each binding site is separated by at least 2 amino acids. In some embodiments, each binding site comprises at least 2 contiguous amino acids (e.g. at least 2, at least 3, at least 4, at least 5, at least 6, at least 7, at least 8, at least 9, or at least 10 amino acids) and each binding site is separated by at least 10 amino acids. In some embodiments, each binding site is separated by at least 20 amino acids (e.g. at least 20, at least 25, at least 30, at least 35, at least 40, at least 45, at least 50 amino acids).

In some embodiments, the HbcAg capture antibody binds to an epitope contained within amino acids 1-149 of SEQ ID NO: 1. Amino acids 1-149 of SEQ ID NO: 1 are shown in SEQ ID NO: 3. In some embodiments, the HBcAg capture antibody binds to an epitope of about 3 to about 50 amino acids on SEQ ID NO: 3. In some embodiments, the HBcAg capture antibody binds to an epitope of about 3 to about 40 contiguous amino acids, about 3 to about 35 contiguous amino acids, about 3 to about 30 contiguous amino acids, about 3 to about 25 contiguous amino acids, about 3 to about 20 contiguous amino acids, or about 3 to about 15 contiguous amino acids on SEQ ID NO: 3. In some embodiments, the HBcAg capture antibody binds to an epitope of about 3 to about 15 amino acids (e.g., contiguous amino acids) on SEQ ID NO: 3. In some embodiments, the HBcAg capture antibody binds to an epitope of about 3, about 4, about 5, about 6, about 7, about 8, about 9, about 10, about 11, about 12, about 13, about 14, or about 15 contiguous amino acids on SEQ ID NO: 3. In some embodiments, the HBcAg capture antibody binds to non-contiguous epitopes. For example, in some embodiments the HBcAg capture antibody binds to more multiple binding sites, and each binding site is separated by at least 2 amino acids. For example, in some embodiments the capture antibody binds to multiple binding sites, wherein each binding site comprises at least 2 contiguous amino acids and wherein each binding site is separated by at least 2 amino acids. In some embodiments, each binding site comprises at least 2 contiguous amino acids (e.g. at least 2, at least 3, at least 4, at least 5, at least 6, at least 7, at least 8, at least 9, or at least 10 amino acids) and each binding site is separated by at least 10 amino acids. In some embodiments, each binding site is separated by at least 20 amino acids (e.g. at least 20, at least 25, at least 30, at least 35, at least 40, at least 45, at least 50 amino acids).

In some embodiments, the HBcAg detection antibody binds to an epitope on HBcAg that is not bound by the capture antibody, thus forming a capture antibody-HBcAg-detection antibody complex. In some embodiments, the HBcAg detection antibody binds to an epitope on the C-terminus of HBcAg. In some embodiments, HBcAg detection antibody binds to an epitope on the C-terminus of SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, or SEQ ID NO: 40. In some embodiments, HBcAg detection antibody binds to an epitope on the C-terminus of an amino acid sequence having at least 95% sequence identity to SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, or SEQ ID NO: 40. In some embodiments the HBcAg detection antibody binds to an epitope on SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, or SEQ ID NO: 40. In some embodiments, the HBcAg detection antibody binds to an epitope of about 3 to about 36 amino acids (e.g., contiguous amino acids) in length. In some embodiments, the HBcAg detection antibody binds to an epitope of about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, or about 36 contiguous amino acids in length.

In yet other embodiments, the HBcAg detection antibody binds to an epitope on HBcAg that is not bound by the capture antibody, thus forming a capture antibody-HBcAg-detection antibody complex. In some embodiments, the HBcAg detection antibody binds to an epitope on the C-terminus of HBcAg. In some embodiments, HBcAg detection antibody binds to an epitope on the C-terminus of SEQ ID NO: 1, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, or SEQ ID NO: 12. In some embodiments, HBcAg detection antibody binds to an epitope on the C-terminus of an amino acid sequence having at least 95% sequence identity to SEQ ID NO: 1, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, or SEQ ID NO: 12. In some embodiments the HBcAg detection antibody binds to an epitope on SEQ ID NO: 2, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, or SEQ ID NO: 21. In some embodiments, the HBcAg detection antibody binds to an epitope of about 3 to about 36 amino acids (e.g., contiguous amino acids) in length. In some embodiments, the HBcAg detection antibody binds to an epitope of about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, or about 36 contiguous amino acids in length. In yet other embodiments, the HBcAg detection antibody capture antibody specifically binds to an epitope within amino acids 150-185 of SEQ ID NO:1, SEQ ID NO: 4, SEQ ID NO: 5, SEQ ID NO: 6, SEQ ID NO: 7, SEQ ID NO: 8, SEQ ID NO: 10, SEQ ID NO: 11, or SEQ ID NO: 12 and the HBcAg detection antibody specifically binds to an epitope within amino acids 1-149 of SEQ ID NO: 1, SEQ ID NO: 4, SEQ ID NO: 5, SEQ ID NO: 6, SEQ ID NO: 7, SEQ ID NO: 8, SEQ ID NO: 10, SEQ ID NO: 11, or SEQ ID NO: 12. In some aspects of this embodiment, the HBcAg capture antibody and HBcAg detection antibody can specifically bind to overlapping epitope within amino acids of SEQ ID NO:1, SEQ ID NO: 4, SEQ ID NO: 5, SEQ ID NO: 6, SEQ ID NO: 7, SEQ ID NO: 8, SEQ ID NO: 10, SEQ ID NO: 11, or SEQ ID NO: 12. For example, the HBcAg capture antibody can bind to an epitope within amino acids 145-155 of SEQ ID NO:1, SEQ ID NO: 4, SEQ ID NO: 5, SEQ ID NO: 6, SEQ ID NO: 7, SEQ ID NO: 8, SEQ ID NO: 10, SEQ ID NO: 11, or SEQ ID NO: 12 and the HBcAg detection antibody can bind to an epitope within amino acids 139-149 of SEQ ID NO:1, SEQ ID NO: 4, SEQ ID NO: 5, SEQ ID NO: 6, SEQ ID NO: 7, SEQ ID NO: 8, SEQ ID NO: 10, SEQ ID NO: 11, or SEQ ID NO: 12, etc.

In still yet other embodiments, In yet other embodiments, the HBcAg capture antibody specifically binds to an epitope within amino acids 1-149 of SEQ ID NO:1, SEQ ID NO: 4, SEQ ID NO: 5, SEQ ID NO: 6, SEQ ID NO: 7, SEQ ID NO: 8, SEQ ID NO: 10, SEQ ID NO: 11, or SEQ ID NO: 12 and the HBcAg detection antibody specifically binds to an epitope within amino acids 150-185 of SEQ ID NO: 1, SEQ ID NO: 4, SEQ ID NO: 5, SEQ ID NO: 6, SEQ ID NO: 7, SEQ ID NO: 8, SEQ ID NO: 10, SEQ ID NO: 11, or SEQ ID NO: 12. In some aspects of this embodiment, the HbcAg capture antibody and HBcAg detection antibody can specifically bind to overlapping epitope within amino acids of SEQ ID NO:1, SEQ ID NO: 4, SEQ ID NO: 5, SEQ ID NO: 6, SEQ ID NO: 7, SEQ ID NO: 8, SEQ ID NO: 10, SEQ ID NO: 11, or SEQ ID NO: 12. For example, the HbcAg capture antibody can bind to an epitope within amino acids 139-149 of SEQ ID NO:1, SEQ ID NO: 4, SEQ ID NO: 5, SEQ ID NO: 6, SEQ ID NO: 7, SEQ ID NO: 8, SEQ ID NO: 10, SEQ ID NO: 11, or SEQ ID NO: 12 and the HBcAg detection antibody can bind to an epitope within amino acids 145-155 of SEQ ID NO:1, SEQ ID NO: 4, SEQ ID NO: 5, SEQ ID NO: 6, SEQ ID NO: 7, SEQ ID NO: 8, SEQ ID NO: 10, SEQ ID NO: 11, or SEQ ID NO: 12, etc.

In some embodiments, the HBcAg detection antibody binds to an epitope of about 3 to about 36 amino acids (e.g., contiguous amino acids) in length on SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37 or SEQ ID NO: 39. In some embodiments, the HBcAg detection antibody binds to an epitope of about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, or about 36 contiguous amino acids on SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37 or SEQ ID NO: 39. In some embodiments, the HBcAg detection antibody binds to non-contiguous epitopes. In some embodiments, the HBcAg detection antibody binds to non-contiguous epitopes on the C-terminus of HBcAg. For example, in some embodiments the HBcAg detection antibody binds to multiple binding sites, wherein each binding site comprises at least three contiguous amino acids (e.g. at least 3, at least 4, at least 5, at least 6, at least 7 contiguous amino acids) and wherein each binding site is separated by at least one (e.g. at least one, at least two, at least three) amino acid. In some embodiments, the HBcAg detection antibody binds to multiple binding sites on SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37 or SEQ ID NO: 39, wherein each binding site comprises at least three contiguous amino acids (e.g. at least 3, at least 4, at least 5, at least 6, at least 7 contiguous amino acids) and wherein each binding site is separated by at least one (e.g. at least one, at least two, at least three) amino acid.

In still other embodiments, the HBcAg detection antibody binds to an epitope of about 3 to about 36 amino acids (e.g., contiguous amino acids) in length on SEQ ID NO: 2, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, or SEQ ID NO: 21. In some embodiments, the HBcAg detection antibody binds to an epitope of about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, or about 36 contiguous amino acids on SEQ ID NO: 2, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, or SEQ ID NO: 21. In some embodiments, the HBcAg detection antibody binds to non-contiguous epitopes. In some embodiments, the HBcAg detection antibody binds to non-contiguous epitopes on the C-terminus of HBcAg. For example, in some embodiments the HBcAg detection antibody binds to multiple binding sites, wherein each binding site comprises at least three contiguous amino acids (e.g. at least 3, at least 4, at least 5, at least 6, at least 7 contiguous amino acids) and wherein each binding site is separated by at least one (e.g. at least one, at least two, at least three) amino acid. In some embodiments, the HBcAg detection antibody binds to multiple binding sites on SEQ ID NO: 2, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, or SEQ ID NO: 21, wherein each binding site comprises at least three contiguous amino acids (e.g. at least 3, at least 4, at least 5, at least 6, at least 7 contiguous amino acids) and wherein each binding site is separated by at least one (e.g. at least one, at least two, at least three) amino acid.

In some embodiments, the HBcAg detection antibody binds to an epitope of about 3 to about 36 contiguous amino acids on SEQ ID NO: 2. In some embodiments, the HBcAg detection antibody binds to an epitope of about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, or about 36 amino acids (e.g., contiguous) in length on SEQ ID NO: 2. In some embodiments the HBcAg detection antibody binds to multiple binding sites on SEQ ID NO: 2, wherein each binding site comprises at least three contiguous amino acids (e.g. at least 3, at least 4, at least 5, at least 6, at least 7 contiguous amino acids) and wherein each binding site is separated by at least one (e.g. at least one, at least two, at least three) amino acid.

In some embodiments, the detection antibody further comprises a detectable label. Suitable detectable labels are described herein. In some embodiments, a signal generated by the detectable label in the capture antibody-HBcAg-detection antibody complex is indicative of the presence and/or amount (e.g. level) of HBcAg in the sample.

In some embodiments, detecting the presence, level, or status of human P-HBcAg in the sample comprises contacting the sample with an antibody that specifically binds to P-HBcAg (e.g. a P-HBcAg capture antibody) to form a capture antibody-P-HBcAg complex. In some embodiments, the P-HBcAg capture antibody binds to an epitope on the C-terminus of P-HBcAg. In some embodiments, P-HBcAg capture antibody binds to an epitope on the C-terminus of SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, or SEQ ID NO: 40. In some embodiments, P-HBcAg capture antibody binds to an epitope on the C-terminus of an amino acid sequence having at least 95% sequence identity to SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, or SEQ ID NO: 40. In some embodiments, at least one amino acid, at least two amino acids, at least three amino acids, at least four amino acids, at least 5 amino acids, at least 6 amino acids, or 7 amino acids are phosphorylated.

In still some other embodiments, detecting the presence, level, or status of human P-HBcAg in the sample comprises contacting the sample with an antibody that specifically binds to P-HBcAg (e.g. a P-HBcAg capture antibody) to form a capture antibody-P-HBcAg complex. In some embodiments, the P-HBcAg capture antibody binds to an epitope on the C-terminus of P-HBcAg. In some embodiments, P-HBcAg capture antibody binds to an epitope on the C-terminus of SEQ ID NO: 1, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, or SEQ ID NO: 12. In some embodiments, P-HBcAg capture antibody binds to an epitope on the C-terminus of an amino acid sequence having at least 95% sequence identity to SEQ ID NO: 1, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, or SEQ ID NO: 12. In some embodiments, at least one amino acid, at least two amino acids, at least three amino acids, at least four amino acids, at least 5 amino acids, at least 6 amino acids, or 7 amino acids are phosphorylated.

In some embodiments the P-HBcAg capture antibody binds to an epitope on SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37 or SEQ ID NO: 39. In some embodiments, the P-HBcAg capture antibody binds to an epitope of about 3 to about 36 amino acids (e.g. contiguous) in length. In some embodiments, the P-HBcAg capture antibody binds to an epitope of about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, or about 36 amino acids (e.g., contiguous) in length, provided that at least one amino acid, at least two amino acids, at least three amino acids, at least four amino acids, at least 5 amino acids, at least 6 amino acids, or 7 amino acids are phosphorylated.

In still yet other embodiments the P-HBcAg capture antibody binds to an epitope on SEQ ID NO: 2, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, or SEQ ID NO: 21. In some embodiments, the P-HBcAg capture antibody binds to an epitope of about 3 to about 36 amino acids (e.g. contiguous) in length. In some embodiments, the P-HBcAg capture antibody binds to an epitope of about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, or about 36 amino acids (e.g., contiguous) in length, provided that at least one amino acid, at least two amino acids, at least three amino acids, at least four amino acids, at least 5 amino acids, at least 6 amino acids, or 7 amino acids are phosphorylated.

In some embodiments, the P-HBcAg capture antibody binds to an epitope of about 3 to about 36 amino acids (e.g. contiguous) in length on SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37 or SEQ ID NO: 39, provided that at least one amino acid, at least two amino acids, at least three amino acids, at least four amino acids, at least 5 amino acids, at least 6 amino acids, or 7 amino acids are phosphorylated. In some embodiments, the P-HBcAg capture antibody binds to an epitope of about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, or about 36 amino acids (e.g., contiguous) in length on SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37 or SEQ ID NO: 39, provided that at least one amino acid, at least two amino acids, at least three amino acids, at least four amino acids, at least 5 amino acids, at least 6 amino acids, or 7 amino acids are phosphorylated. In some embodiments, the P-HBcAg capture antibody binds to non-contiguous epitopes on the C-terminus of P-HBcAg. In some embodiments, the P-HBcAg capture antibody binds to multiple binding sites, wherein each binding site comprises at least three contiguous amino acids (e.g. at least 3, at least 4, at least 5, at least 6, at least 7 contiguous amino acids) and wherein each binding site is separated by at least one (e.g. at least one, at least two, at least three) amino acid, and wherein at least one amino acid, at least two amino acids, at least three amino acids, at least four amino acids, at least 5 amino acids, at least 6 amino acids, or 7 amino acids are phosphorylated. For example, in some embodiments, the P-HBcAg capture antibody binds to multiple binding sites on SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37 or SEQ ID NO: 39, wherein each binding site comprises at least three contiguous amino acids (e.g. at least 3, at least 4, at least 5, at least 6, at least 7 contiguous amino acids) and wherein each binding site is separated by at least one (e.g. at least one, at least two, at least three) amino acid, and wherein at least one amino acid, at least two amino acids, at least three amino acids, at least four amino acids, at least 5 amino acids, at least 6 amino acids, or 7 amino acids are phosphorylated.

In yet other embodiments, the P-HBcAg capture antibody binds to an epitope of about 3 to about 36 amino acids (e.g. contiguous) in length on SEQ ID NO: 2, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, or SEQ ID NO: 21, provided that at least one amino acid, at least two amino acids, at least three amino acids, at least four amino acids, at least 5 amino acids, at least 6 amino acids, or 7 amino acids are phosphorylated. In some embodiments, the P-HBcAg capture antibody binds to an epitope of about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, or about 36 amino acids (e.g., contiguous) in length on SEQ ID NO: 2, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, or SEQ ID NO: 21, provided that at least one amino acid, at least two amino acids, at least three amino acids, at least four amino acids, at least 5 amino acids, at least 6 amino acids, or 7 amino acids are phosphorylated. In some embodiments, the P-HBcAg capture antibody binds to non-contiguous epitopes on the C-terminus of P-HBcAg. In some embodiments, the P-HBcAg capture antibody binds to multiple binding sites, wherein each binding site comprises at least three contiguous amino acids (e.g. at least 3, at least 4, at least 5, at least 6, at least 7 contiguous amino acids) and wherein each binding site is separated by at least one (e.g. at least one, at least two, at least three) amino acid, and wherein at least one amino acid, at least two amino acids, at least three amino acids, at least four amino acids, at least 5 amino acids, at least 6 amino acids, or 7 amino acids are phosphorylated. For example, in some embodiments, the P-HBcAg capture antibody binds to multiple binding sites on SEQ ID NO: 2, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, or SEQ ID NO: 21, wherein each binding site comprises at least three contiguous amino acids (e.g. at least 3, at least 4, at least 5, at least 6, at least 7 contiguous amino acids) and wherein each binding site is separated by at least one (e.g. at least one, at least two, at least three) amino acid, and wherein at least one amino acid, at least two amino acids, at least three amino acids, at least four amino acids, at least 5 amino acids, at least 6 amino acids, or 7 amino acids are phosphorylated.

The C-terminus of P-HBcAg genotype A is represented by amino acids 150-185 of SEQ ID NO: 1. Amino acids 150-185 of SEQ ID NO: 1 are represented by SEQ ID NO: 2. In some embodiments, the P-HBcAg capture antibody binds to an epitope of about 3 to about 36 amino acids (e.g., contiguous) in length on SEQ ID NO: 2, provided that at least one amino acid, at least two amino acids, at least three amino acids, at least four amino acids, at least 5 amino acids, at least 6 amino acids, or 7 amino acids are phosphorylated. In some embodiments, the P-HBcAg capture antibody binds to an epitope of about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, or about 36 amino acids (e.g., contiguous) in length on SEQ ID NO: 2, provided that at least one amino acid, at least two amino acids, at least three amino acids, at least four amino acids, at least 5 amino acids, at least 6 amino acids, or 7 amino acids are phosphorylated.

In some embodiments, detecting the presence, level, or status of P-HBcAg in the sample further comprises contacting the sample with a detection antibody that binds to an epitope on P-HBcAg that is not bound by the P-HBcAg capture antibody, thus forming a capture antibody-P-HBcAg-detection antibody complex.

In some embodiments, the P-HBcAg detection antibody binds to an epitope on HBcAg other than the C-terminus. In some embodiments, the P-HBcAg detection antibody binds to an epitope contained within SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, or SEQ ID NO: 40. In some embodiments, the P-HBcAg detection antibody binds to an epitope contained SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, or SEQ ID NO: 40. In some embodiments, the P-HBcAg detection antibody binds to an epitope of about 3 to about 50 contiguous amino acids (about 3 to about 40 contiguous amino acids, about 3 to about 35 contiguous amino acids, about 3 to about 30 contiguous amino acids, about 3 to about 25 contiguous amino acids, about 3 to about 20 contiguous amino acids, or about 3 to about 15 contiguous amino acids).

In still other embodiments, the P-HBcAg detection antibody binds to an epitope on HBcAg other than the C-terminus. In some embodiments, the P-HBcAg detection antibody binds to an epitope contained within amino acids 1-149 of SEQ ID NO: 1, SEQ ID NO: 4, SEQ ID NO: 5, SEQ ID NO: 6, SEQ ID NO: 7, SEQ ID NO: 8, SEQ ID NO: 10, SEQ ID NO: 11, or SEQ ID NO: 12. In some embodiments, the P-HBcAg detection antibody binds to an epitope contained within amino acids 1-161 of SEQ ID NO: 9. In some embodiments, the P-HBcAg detection antibody binds to an epitope contained within amino acids 1-149 of an amino acid sequence having at least 95% sequence identity to SEQ ID NO: 1, SEQ ID NO: 4, SEQ ID NO: 5, SEQ ID NO: 6, SEQ ID NO: 7, SEQ ID NO: 8, SEQ ID NO: 10, SEQ ID NO: 11, or SEQ ID NO: 12. In some embodiments, the P-HBcAg detection antibody binds to an epitope contained within amino acids 1-161 of an amino acid sequence having at least 95% sequence identity to SEQ ID NO: 9. In some embodiments, the P-HBcAg detection antibody binds to an epitope of about 3 to about 50 contiguous amino acids (about 3 to about 40 contiguous amino acids, about 3 to about 35 contiguous amino acids, about 3 to about 30 contiguous amino acids, about 3 to about 25 contiguous amino acids, about 3 to about 20 contiguous amino acids, or about 3 to about 15 contiguous amino acids).

In some embodiments, the P-HBcAg detection antibody binds to an epitope of about 3 to about 50 contiguous amino acids (about 3 to about 40 contiguous amino acids, about 3 to about 35 contiguous amino acids, about 3 to about 30 contiguous amino acids, about 3 to about 25 contiguous amino acids, about 3 to about 20 contiguous amino acids, or about 3 to about 15 contiguous amino acids) within SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, or SEQ ID NO: 40. In some embodiments, the P-HBcAg detection antibody binds to non-contiguous epitopes. In some embodiments, the P-HBcAg detection antibody binds to non-contiguous epitopes on SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, or SEQ ID NO: 40. In some embodiments the P-HBcAg detection antibody binds to more multiple binding sites, and each binding site is separated by at least 2 amino acids. For example, in some embodiments the P-HBcAg detection antibody binds to multiple binding sites, wherein each binding site comprises at least 2 contiguous amino acids and wherein each binding site is separated by at least 2 amino acids. In some embodiments, each binding site comprises at least 2 contiguous amino acids (e.g. at least 2, at least 3, at least 4, at least 5, at least 6, at least 7, at least 8, at least 9, or at least 10 amino acids) and each binding site is separated by at least 10 amino acids. In some embodiments, each binding site is separated by at least 20 amino acids (e.g. at least 20, at least 25, at least 30, at least 35, at least 40, at least 45, at least 50 amino acids).

In still other embodiments, the P-HBcAg detection antibody binds to an epitope of about 3 to about 50 contiguous amino acids (about 3 to about 40 contiguous amino acids, about 3 to about 35 contiguous amino acids, about 3 to about 30 contiguous amino acids, about 3 to about 25 contiguous amino acids, about 3 to about 20 contiguous amino acids, or about 3 to about 15 contiguous amino acids) within amino acids 1-149 of SEQ ID NO: 1, SEQ ID NO: 4, SEQ ID NO: 5, SEQ ID NO: 6, SEQ ID NO: 7, SEQ ID NO: 8, SEQ ID NO: 10, SEQ ID NO: 11, or SEQ ID NO: 12, or within amino acids 1-161 of SEQ ID NO: 9. In some embodiments, the P-HBcAg detection antibody binds to non-contiguous epitopes. In some embodiments, the P-HBcAg detection antibody binds to non-contiguous epitopes on SEQ ID NO: 1, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, or SEQ ID NO: 12. In some embodiments the P-HBcAg detection antibody binds to more multiple binding sites, and each binding site is separated by at least 2 amino acids. For example, in some embodiments the P-HBcAg detection antibody binds to multiple binding sites, wherein each binding site comprises at least 2 contiguous amino acids and wherein each binding site is separated by at least 2 amino acids. In some embodiments, each binding site comprises at least 2 contiguous amino acids (e.g. at least 2, at least 3, at least 4, at least 5, at least 6, at least 7, at least 8, at least 9, or at least 10 amino acids) and each binding site is separated by at least 10 amino acids. In some embodiments, each binding site is separated by at least 20 amino acids (e.g. at least 20, at least 25, at least 30, at least 35, at least 40, at least 45, at least 50 amino acids).

In some aspects, the detection antibody binds to an epitope contained within amino acids 1-149 of SEQ ID NO: 1. Amino acids 1-149 of SEQ ID NO: 1 are represented by SEQ ID NO: 3. In some embodiments, the P-HBcAg detection antibody binds to an epitope of about 3 to about 50 amino acids on SEQ ID NO: 3. In some embodiments, the P-HBcAg detection antibody binds to an epitope of about 3 to about 40 contiguous amino acids, about 3 to about 35 contiguous amino acids, about 3 to about 30 contiguous amino acids, about 3 to about 25 contiguous amino acids, about 3 to about 20 contiguous amino acids, or about 3 to about 15 contiguous amino acids on SEQ ID NO: 3. In some embodiments, the P-HBcAg detection antibody binds to an epitope of about 3 to about 15 amino acids (e.g., contiguous amino acids) on SEQ ID NO: 3 In some embodiments, the P-HBcAg detection antibody binds to an epitope of about 3 to about 15 amino acids (e.g., contiguous) in length on SEQ ID NO: 3 For example, in some embodiments, the P-HBcAg detection antibody binds to an epitope of about 3, about 4, about 5, about 6, about 7, about 8, about 9, about 10, about 11, about 12, about 13, about 14, or about 15 contiguous amino acids on SEQ ID NO: 3. In some embodiments, the P-HBcAg detection antibody binds to non-contiguous epitopes. For example, in some embodiments the P-HBcAg detection antibody binds to more multiple binding sites, and each binding site is separated by at least 2 amino acids. For example, in some embodiments the detection antibody binds to multiple binding sites, wherein each binding site comprises at least 2 contiguous amino acids and wherein each binding site is separated by at least 2 amino acids. In some embodiments, each binding site comprises at least 2 contiguous amino acids (e.g. at least 2, at least 3, at least 4, at least 5, at least 6, at least 7, at least 8, at least 9, or at least 10 amino acids) and each binding site is separated by at least 10 amino acids. In some embodiments, each binding site is separated by at least 20 amino acids (e.g. at least 20, at least 25, at least 30, at least 35, at least 40, at least 45, at least 50 amino acids).

In some embodiments, the P-HBcAg capture antibody binds to an epitope on HBcAg other than the C-terminus. In some embodiments, the P-HBcAg capture antibody binds to an epitope contained within SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, or SEQ ID NO: 40. In some embodiments, the P-HBcAg capture antibody binds to an epitope contained within an amino acid sequence having at least 95% sequence identity to SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, or SEQ ID NO: 40. In some embodiments, the P-HBcAg capture antibody binds to an epitope of about 3 to about 50 contiguous amino acids (about 3 to about 40 contiguous amino acids, about 3 to about 35 contiguous amino acids, about 3 to about 30 contiguous amino acids, about 3 to about 25 contiguous amino acids, about 3 to about 20 contiguous amino acids, or about 3 to about 15 contiguous amino acids). In still further embodiments, the P-HBcAg capture antibody binds to an epitope on HBcAg other than the C-terminus. In some embodiments, the P-HBcAg capture antibody binds to an epitope contained within amino acids 1-149 of SEQ ID NO: 1, SEQ ID NO: 4, SEQ ID NO: 5, SEQ ID NO: 6, SEQ ID NO: 7, SEQ ID NO: 8, SEQ ID NO: 10, SEQ ID NO: 11, or SEQ ID NO: 12. In some embodiments, the P-HBcAg capture antibody binds to an epitope contained within amino acids 1-161 of SEQ ID NO: 9. In some embodiments, the P-HBcAg capture antibody binds to an epitope contained within amino acids 1-149 of an amino acid sequence having at least 95% sequence identity to SEQ ID NO: 1, SEQ ID NO: 4, SEQ ID NO: 5, SEQ ID NO: 6, SEQ ID NO: 7, SEQ ID NO: 8, SEQ ID NO: 10, SEQ ID NO: 11, or SEQ ID NO: 12. In some embodiments, the P-HBcAg capture antibody binds to an epitope contained within amino acids 1-161 of an amino acid sequence having at least 95% sequence identity to SEQ ID NO: 9. In some embodiments, the P-HBcAg capture antibody binds to an epitope of about 3 to about 50 contiguous amino acids (about 3 to about 40 contiguous amino acids, about 3 to about 35 contiguous amino acids, about 3 to about 30 contiguous amino acids, about 3 to about 25 contiguous amino acids, about 3 to about 20 contiguous amino acids, or about 3 to about 15 contiguous amino acids).

In some embodiments, the P-HBcAg capture antibody binds to an epitope of about 3 to about 50 contiguous amino acids (about 3 to about 40 contiguous amino acids, about 3 to about 35 contiguous amino acids, about 3 to about 30 contiguous amino acids, about 3 to about 25 contiguous amino acids, about 3 to about 20 contiguous amino acids, or about 3 to about 15 contiguous amino acids) within SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, or SEQ ID NO: 40. In some embodiments, the P-HBcAg capture antibody binds to non-contiguous epitopes. In some embodiments, the P-HBcAg capture antibody binds to non-contiguous epitopes on SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, or SEQ ID NO: 40. In some embodiments the P-HBcAg capture antibody binds to more multiple binding sites, and each binding site is separated by at least 2 amino acids. For example, in some embodiments the P-HBcAg detection antibody binds to multiple binding sites, wherein each binding site comprises at least 2 contiguous amino acids and wherein each binding site is separated by at least 2 amino acids. In some embodiments, each binding site comprises at least 2 contiguous amino acids (e.g. at least 2, at least 3, at least 4, at least 5, at least 6, at least 7, at least 8, at least 9, or at least 10 amino acids) and each binding site is separated by at least 10 amino acids. In some embodiments, each binding site is separated by at least 20 amino acids (e.g. at least 20, at least 25, at least 30, at least 35, at least 40, at least 45, at least 50 amino acids).

In still further embodiments, the P-HBcAg capture antibody binds to an epitope of about 3 to about 50 contiguous amino acids (about 3 to about 40 contiguous amino acids, about 3 to about 35 contiguous amino acids, about 3 to about 30 contiguous amino acids, about 3 to about 25 contiguous amino acids, about 3 to about 20 contiguous amino acids, or about 3 to about 15 contiguous amino acids) within amino acids 1-149 of SEQ ID NO: 1, SEQ ID NO: 4, SEQ ID NO: 5, SEQ ID NO: 6, SEQ ID NO: 7, SEQ ID NO: 8, SEQ ID NO: 10, SEQ ID NO: 11, or SEQ ID NO: 12, or within amino acids 1-161 of SEQ ID NO: 9. In some embodiments, the P-HBcAg capture antibody binds to non-contiguous epitopes. In some embodiments, the P-HBcAg capture antibody binds to non-contiguous epitopes on SEQ ID NO: 1, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, or SEQ ID NO: 12. In some embodiments the P-HBcAg capture antibody binds to more multiple binding sites, and each binding site is separated by at least 2 amino acids. For example, in some embodiments the P-HBcAg detection antibody binds to multiple binding sites, wherein each binding site comprises at least 2 contiguous amino acids and wherein each binding site is separated by at least 2 amino acids. In some embodiments, each binding site comprises at least 2 contiguous amino acids (e.g. at least 2, at least 3, at least 4, at least 5, at least 6, at least 7, at least 8, at least 9, or at least 10 amino acids) and each binding site is separated by at least 10 amino acids. In some embodiments, each binding site is separated by at least 20 amino acids (e.g. at least 20, at least 25, at least 30, at least 35, at least 40, at least 45, at least 50 amino acids).

In some embodiments, the P-HBcAg capture antibody binds to an epitope contained within amino acids 1-149 of SEQ ID NO: 1. In some embodiments, the P-HBcAg capture antibody binds to an epitope of about 3 to about 50 amino acids on SEQ ID NO: 3. In some embodiments, the P-HBcAg capture antibody binds to an epitope of about 3 to about 40 contiguous amino acids, about 3 to about 35 contiguous amino acids, about 3 to about 30 contiguous amino acids, about 3 to about 25 contiguous amino acids, about 3 to about 20 contiguous amino acids, or about 3 to about 15 contiguous amino acids on SEQ ID NO: 3. In some embodiments, the P-HBcAg capture antibody binds to an epitope of about 3 to about 15 amino acids (e.g., contiguous amino acids) on SEQ ID NO: 3. In some embodiments, the P-HBcAg capture antibody binds to an epitope of about 3, about 4, about 5, about 6, about 7, about 8, about 9, about 10, about 11, about 12, about 13, about 14, or about 15 contiguous amino acids on SEQ ID NO: 3. In some embodiments, the P-HBcAg capture antibody binds to non-contiguous epitopes. For example, in some embodiments the P-HBcAg capture antibody binds to more multiple binding sites, and each binding site is separated by at least 2 amino acids. For example, in some embodiments the capture antibody binds to multiple binding sites, wherein each binding site comprises at least 2 contiguous amino acids and wherein each binding site is separated by at least 2 amino acids. In some embodiments, each binding site comprises at least 2 contiguous amino acids (e.g. at least 2, at least 3, at least 4, at least 5, at least 6, at least 7, at least 8, at least 9, or at least 10 amino acids) and each binding site is separated by at least 10 amino acids. In some embodiments, each binding site is separated by at least 20 amino acids (e.g. at least 20, at least 25, at least 30, at least 35, at least 40, at least 45, at least 50 amino acids).

In some embodiments, the P-HBcAg detection antibody binds to an epitope on P-HBcAg that is not bound by the capture antibody, thus forming a capture antibody-P-HBcAg-detection antibody complex. In some embodiments, the P-HBcAg detection antibody binds to an epitope on the C-terminus of P-HBcAg. In some embodiments, P-HBcAg detection antibody binds to an epitope on the C-terminus of SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, or SEQ ID NO: 40. In some embodiments, P-HBcAg detection antibody binds to an epitope on the C-terminus of an amino acid sequence having at least 95% sequence identity to SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, or SEQ ID NO: 40. In some embodiments the P-HBcAg detection antibody binds to an epitope on SEQ ID NO: 23, SEQ ID NO: 25, SEQ ID NO: 27, SEQ ID NO:

29, SEQ ID NO: 31, SEQ ID NO: 33, SEQ ID NO: 35, SEQ ID NO: 37 or SEQ ID NO: 39. In some embodiments, the P-HBcAg detection antibody binds to an epitope of about 3 to about 36 amino acids (e.g. contiguous) in length. In some embodiments, the P-HBcAg detection antibody binds to an epitope of about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, or about 36 amino acids (e.g., contiguous) in length, provided that at least one amino acid, at least two amino acids, at least three amino acids, at least four amino acids, at least 5 amino acids, at least 6 amino acids, or 7 amino acids are phosphorylated.

In yet other embodiments, the P-HBcAg detection antibody capture antibody specifically binds to an epitope within amino acids 150-185 of SEQ ID NO:1, SEQ ID NO: 4, SEQ ID NO: 5, SEQ ID NO: 6, SEQ ID NO: 7, SEQ ID NO: 8, SEQ ID NO: 10, SEQ ID NO: 11, or SEQ ID NO: 12 and the P-HBcAg detection antibody specifically binds to an epitope within amino acids 1-149 of SEQ ID NO: 1, SEQ ID NO: 4, SEQ ID NO: 5, SEQ ID NO: 6, SEQ ID NO: 7, SEQ ID NO: 8, SEQ ID NO: 10, SEQ ID NO: 11, or SEQ ID NO: 12. In some aspects of this embodiment, the P-HBcAg capture antibody and P-HBcAg detection antibody can specifically bind to overlapping epitope within amino acids of SEQ ID NO:1, SEQ ID NO: 4, SEQ ID NO: 5, SEQ ID NO: 6, SEQ ID NO: 7, SEQ ID NO: 8, SEQ ID NO: 10, SEQ ID NO: 11, or SEQ ID NO: 12. For example, the P-HBcAg capture antibody can bind to an epitope within amino acids 145-155 of SEQ ID NO:1, SEQ ID NO: 4, SEQ ID NO: 5, SEQ ID NO: 6, SEQ ID NO: 7, SEQ ID NO: 8, SEQ ID NO: 10, SEQ ID NO: 11, or SEQ ID NO: 12 and the P-HBcAg detection antibody can bind to an epitope within amino acids 139-149 of SEQ ID NO:1, SEQ ID NO: 4, SEQ ID NO: 5, SEQ ID NO: 6, SEQ ID NO: 7, SEQ ID NO: 8, SEQ ID NO: 10, SEQ ID NO: 11, or SEQ ID NO: 12, etc.

In still yet other embodiments, In yet other embodiments, the P-HBcAg capture antibody specifically binds to an epitope within amino acids 1-149 of SEQ ID NO:1, SEQ ID NO: 4, SEQ ID NO: 5, SEQ ID NO: 6, SEQ ID NO: 7, SEQ ID NO: 8, SEQ ID NO: 10, SEQ ID NO: 11, or SEQ ID NO: 12 and the P-HBcAg detection antibody specifically binds to an epitope within amino acids 150-185 of SEQ ID NO: 1, SEQ ID NO: 4, SEQ ID NO: 5, SEQ ID NO: 6, SEQ ID NO: 7, SEQ ID NO: 8, SEQ ID NO: 10, SEQ ID NO: 11, or SEQ ID NO: 12. In some aspects of this embodiment, the P-HbcAg capture antibody and P-HBcAg detection antibody can specifically bind to overlapping epitope within amino acids of SEQ ID NO:1, SEQ ID NO: 4, SEQ ID NO: 5, SEQ ID NO: 6, SEQ ID NO: 7, SEQ ID NO: 8, SEQ ID NO: 10, SEQ ID NO: 11, or SEQ ID NO: 12. For example, the P-HbcAg capture antibody can bind to an epitope within amino acids 139-149 of SEQ ID NO:1, SEQ ID NO: 4, SEQ ID NO: 5, SEQ ID NO: 6, SEQ ID NO: 7, SEQ ID NO: 8, SEQ ID NO: 10, SEQ ID NO: 11, or SEQ ID NO: 12 and the P-HBcAg detection antibody can bind to an epitope within amino acids 145-155 of SEQ ID NO:1, SEQ ID NO: 4, SEQ ID NO: 5, SEQ ID NO: 6, SEQ ID NO: 7, SEQ ID NO: 8, SEQ ID NO: 10, SEQ ID NO: 11, or SEQ ID NO: 12, etc.

In still further embodiments, the P-HBcAg detection antibody binds to an epitope on P-HBcAg that is not bound by the capture antibody, thus forming a capture antibody-P-HBcAg-detection antibody complex. In some embodiments, the P-HBcAg detection antibody binds to an epitope on the C-terminus of P-HBcAg. In some embodiments, P-HBcAg detection antibody binds to an epitope on the C-terminus of SEQ ID NO: 1, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, or SEQ ID NO: 12. In some embodiments, P-HBcAg detection antibody binds to an epitope on the C-terminus of an amino acid sequence having at least 95% sequence identity to SEQ ID NO: 1, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, or SEQ ID NO: 12. In some embodiments the P-HBcAg detection antibody binds to an epitope on SEQ ID NO: 2, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, or SEQ ID NO: 21. In some embodiments, the P-HBcAg detection antibody binds to an epitope of about 3 to about 36 amino acids (e.g. contiguous) in length. In some embodiments, the P-HBcAg detection antibody binds to an epitope of about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, or about 36 amino acids (e.g., contiguous) in length, provided that at least one amino acid, at least two amino acids, at least three amino acids, at least four amino acids, at least 5 amino acids, at least 6 amino acids, or 7 amino acids are phosphorylated.

In some embodiments, the P-HBcAg detection antibody binds to an epitope of about 3 to about 36 amino acids (e.g. contiguous) in length on SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37 or SEQ ID NO: 39, provided that at least one amino acid, at least two amino acids, at least three amino acids, at least four amino acids, at least 5 amino acids, at least 6 amino acids, or 7 amino acids are phosphorylated. In some embodiments, the P-HBcAg detection antibody binds to an epitope of about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, or about 36 amino acids (e.g., contiguous) in length on SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37 or SEQ ID NO: 39, provided that at least one amino acid, at least two amino acids, at least three amino acids, at least four amino acids, at least 5 amino acids, at least 6 amino acids, or 7 amino acids are phosphorylated. In some embodiments, the P-HBcAg detection antibody binds to non-contiguous epitopes on the C-terminus of P-HBcAg. In some embodiments, the P-HBcAg detection antibody binds to multiple binding sites. wherein each binding site comprises at least three contiguous amino acids (e.g. at least 3, at least 4, at least 5, at least 6, at least 7 contiguous amino acids) and wherein each binding site is separated by at least one (e.g. at least one, at least two, at least three) amino acid, and wherein at least one amino acid, at least two amino acids, at least three amino acids, at least four amino acids, at least 5 amino acids, at least 6 amino acids, or 7 amino acids are phosphorylated. For example, in some embodiments, the P-HBcAg detection antibody binds to multiple binding sites on SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37 or SEQ ID NO: 39, wherein each binding site comprises at least three contiguous amino acids (e.g. at least 3, at least 4, at least 5, at least 6, at least 7 contiguous amino acids) and wherein each binding site is separated by at least one (e.g. at least one, at least two, at least three) amino acid, and wherein at least one amino acid, at least two amino acids, at least three amino acids, at least four amino acids, at least 5 amino acids, at least 6 amino acids, or 7 amino acids are phosphorylated.

In still yet further embodiments, the P-HBcAg detection antibody binds to an epitope of about 3 to about 36 amino acids (e.g. contiguous) in length on SEQ ID NO: 2, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, or SEQ ID NO: 21, provided that at least one amino acid, at least two amino acids, at least three amino acids, at least four amino acids, at least 5 amino acids, at least 6 amino acids, or 7 amino acids are phosphorylated. In some embodiments, the P-HBcAg detection antibody binds to an epitope of about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, or about 36 amino acids (e.g., contiguous) in length on SEQ ID NO: 2, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, or SEQ ID NO: 21, provided that at least one amino acid, at least two amino acids, at least three amino acids, at least four amino acids, at least 5 amino acids, at least 6 amino acids, or 7 amino acids are phosphorylated. In some embodiments, the P-HBcAg detection antibody binds to non-contiguous epitopes on the C-terminus of P-HBcAg. In some embodiments, the P-HBcAg detection antibody binds to multiple binding sites. wherein each binding site comprises at least three contiguous amino acids (e.g. at least 3, at least 4, at least 5, at least 6, at least 7 contiguous amino acids) and wherein each binding site is separated by at least one (e.g. at least one, at least two, at least three) amino acid, and wherein at least one amino acid, at least two amino acids, at least three amino acids, at least four amino acids, at least 5 amino acids, at least 6 amino acids, or 7 amino acids are phosphorylated. For example, in some embodiments, the P-HBcAg detection antibody binds to multiple binding sites on SEQ ID NO: 2, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, or SEQ ID NO: 21, wherein each binding site comprises at least three contiguous amino acids (e.g. at least 3, at least 4, at least 5, at least 6, at least 7 contiguous amino acids) and wherein each binding site is separated by at least one (e.g. at least one, at least two, at least three) amino acid, and wherein at least one amino acid, at least two amino acids, at least three amino acids, at least four amino acids, at least 5 amino acids, at least 6 amino acids, or 7 amino acids are phosphorylated.

In some embodiments, the P-HBcAg detection antibody binds to an epitope of about 3 to about 36 contiguous amino acids on SEQ ID NO: 2 or SEQ ID NO: 25, provided that at least one amino acid, at least two amino acids, at least three amino acids, at least four amino acids, at least 5 amino acids, at least 6 amino acids, or 7 amino acids are phosphorylated. In some embodiments, the P-HBcAg detection antibody binds to an epitope of about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, or about 36 amino acids (e.g., contiguous) in length on SEQ ID NO: 2 or SEQ ID NO:25, provided that at least one amino acid, at least two amino acids, at least three amino acids, at least four amino acids, at least 5 amino acids, at least 6 amino acids, or 7 amino acids are phosphorylated.

In some embodiments, the detection antibody further comprises a detectable label. Suitable detectable labels are described herein. In some embodiments, a signal generated by the detectable label in the capture antibody-P-HBcAg-detection antibody complex is indicative of the presence and/or amount (e.g. level) of P-HBcAg in the sample.

In some embodiments, the first specific binding member is immobilized on a solid support. In some embodiments, the second specific binding member is immobilized on a solid support. In some embodiments, the first specific binding member is an HBV biomarker antibody as described below.

In some embodiments, the sample is diluted or undiluted. The sample can be from about 1 to about 25 microliters, about 1 to about 24 microliters, about 1 to about 23 microliters, about 1 to about 22 microliters, about 1 to about 21 microliters, about 1 to about 20 microliters, about 1 to about 18 microliters, about 1 to about 17 microliters, about 1 to about 16 microliters, about 15 microliters or about 1 microliter, about 2 microliters, about 3 microliters, about 4 microliters, about 5 microliters, about 6 microliters, about 7 microliters, about 8 microliters, about 9 microliters, about 10 microliters, about 11 microliters, about 12 microliters, about 13 microliters, about 14 microliters, about 15 microliters, about 16 microliters, about 17 microliters, about 18 microliters, about 19 microliters, about 20 microliters, about 21 microliters, about 22 microliters, about 23 microliters, about 24 microliters or about 25 microliters. In some embodiments, the sample is from about 1 to about 150 microliters or less or from about 1 to about 25 microliters or less.

Some instruments (such as, for example the Abbott Laboratories instruments ARCHITECT®, Abbott Alinity instruments, and other core laboratory instruments) other than a point-of-care device may be capable of measuring levels of an HBV biomarker in a sample at about 4 pg/L at 10% CV or lower. Other methods of detection include the use of or can be adapted for use on a nanopore device or nanowell device. Examples of nanopore devices are described in International Patent Publication No. WO 2016/161402, which is hereby incorporated by reference in its entirety. Examples of nanowell device are described in International Patent Publication No. WO 2016/161400, which is hereby incorporated by reference in its entirety.

Antibodies may be prepared by any of a variety of techniques, including those well known to those skilled in the art. In general, antibodies can be produced by cell culture techniques, including the generation of monoclonal antibodies via conventional techniques, or via transfection of antibody genes, heavy chains, and/or light chains into suitable bacterial or mammalian cell hosts, in order to allow for the production of antibodies, wherein the antibodies may be recombinant. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is possible to express the antibodies in either prokaryotic or eukaryotic host cells, expression of antibodies in eukaryotic cells is specifically contemplated, and includes mammalian host cells, because such eukaryotic cells (e.g., mammalian cells) are more likely than prokaryotic cells to assemble and secrete a properly folded and immunologically active antibody.

Exemplary mammalian host cells for expressing the recombinant antibodies include Chinese Hamster Ovary (CHO cells) (including dhfr-CHO cells, described in Urlaub and Chasin, *Proc. Natl. Acad. Sci. USA,* 77: 4216-4220 (1980)), used with a DHFR selectable marker, e.g., as described in Kaufman and Sharp, *J. Mol. Biol.,* 159: 601-621 (1982), NS0 myeloma cells, COS cells, and SP2 cells. When recombinant expression vectors encoding antibody genes are introduced into mammalian host cells, the antibodies are produced by culturing the host cells for a period of time sufficient to allow for expression of the antibody in the host cells, or secretion of the antibody into the culture medium in which the host cells are grown. Antibodies can be recovered from the culture medium using standard protein purification methods.

Host cells can also be used to produce functional antibody fragments, such as Fab fragments or scFv molecules. It will be understood that variations on the above procedure may be performed. For example, it may be desirable to transfect a host cell with DNA encoding functional fragments of either the light chain and/or the heavy chain of an antibody. Recombinant DNA technology may also be used to remove some, or all, of the DNA encoding either or both of the light and heavy chains that is not necessary for binding to the antigens of interest. The molecules expressed from such truncated DNA molecules are also encompassed by the antibodies. In addition, bifunctional antibodies may be produced in which one heavy and one light chain are an antibody (i.e., binds human troponin I) and the other heavy and light chain are specific for an antigen other than a human HBV biomarker by crosslinking an antibody to a second antibody by standard chemical crosslinking methods.

In some embodiments, a system for recombinant expression of an antibody, or antigen-binding portion thereof, includes a recombinant expression vector encoding both the antibody heavy chain and the antibody light chain that is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells, and recover the antibody from the culture medium. Still further, the method of synthesizing a recombinant antibody may be by culturing a host cell in a suitable culture medium until a recombinant antibody is synthesized. The method can further comprise isolating the recombinant antibody from the culture medium.

Methods of preparing monoclonal antibodies involve the preparation of immortal cell lines capable of producing antibodies having the desired specificity. Such cell lines may be produced from spleen cells obtained from an immunized animal. The animal may be immunized with an HBV biomarker or a fragment and/or variant thereof. The peptide used to immunize the animal may comprise amino acids encoding human Fc, for example the fragment crystallizable region or tail region of human antibody. The spleen cells may then be immortalized by, for example, fusion with a myeloma cell fusion partner. A variety of fusion techniques may be employed. For example, the spleen cells and myeloma cells may be combined with a nonionic detergent for a few minutes and then plated at low density on a selective medium that supports that growth of hybrid cells, but not myeloma cells. One such technique uses hypoxanthine, aminopterin, thymidine (HAT) selection. Another technique includes electrofusion. After a sufficient time, usually about 1 to 2 weeks, colonies of hybrids are observed. Single colonies are selected and their culture supernatants tested for binding activity against the polypeptide. Hybridomas having high reactivity and specificity may be used.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. Affinity chromatography is an example of a method that can be used in a process to purify the antibodies.

The proteolytic enzyme papain preferentially cleaves IgG molecules to yield several fragments, two of which (the F(ab) fragments) each comprise a covalent heterodimer that includes an intact antigen-binding site. The enzyme pepsin is able to cleave IgG molecules to provide several fragments, including the $F(ab')_2$ fragment, which comprises both antigen-binding sites.

The Fv fragment can be produced by preferential proteolytic cleavage of an IgM, and on rare occasions IgG or IgA immunoglobulin molecules. The Fv fragment may be derived using recombinant techniques. The Fv fragment includes a non-covalent VH:VL heterodimer including an antigen-binding site that retains much of the antigen recognition and binding capabilities of the native antibody molecule.

The antibody, antibody fragment, or derivative may comprise a heavy chain and a light chain complementarity determining region ("CDR") set, respectively interposed between a heavy chain and a light chain framework ("FR") set which provide support to the CDRs and define the spatial relationship of the CDRs relative to each other. The CDR set may contain three hypervariable regions of a heavy or light chain V region.

Other suitable methods of producing or isolating antibodies of the requisite specificity can be used, including, but not limited to, methods that select recombinant antibody from a peptide or protein library (e.g., but not limited to, a bacteriophage, ribosome, oligonucleotide, RNA, cDNA, yeast or the like, display library); e.g., as available from various commercial vendors such as Cambridge Antibody Technologies (Cambridgeshire, UK), MorphoSys (Martinsreid/Planegg, Del.), Biovation (Aberdeen, Scotland, UK) BioInvent (Lund, Sweden), using methods known in the art. See U.S. Pat. Nos. 4,704,692; 5,723,323; 5,763,192; 5,814,476; 5,817,483; 5,824,514; 5,976,862. Alternative methods rely upon immunization of transgenic animals (e.g., SCID mice, Nguyen et al. (1997) *Microbiol. Immunol.* 41:901-907; Sandhu et al. (1996) *Crit. Rev. Biotechnol.* 16:95-118; Eren et al. (1998) *Immunol.* 93:154-161) that are capable of producing a repertoire of human antibodies, as known in the art and/or as described herein. Such techniques, include, but are not limited to, ribosome display (Hanes et al. (1997) *Proc. Natl. Acad. Sci. USA,* 94:4937-4942; Hanes et al.

(1998) *Proc. Natl. Acad. Sci. USA,* 95:14130-14135); single cell antibody producing technologies (e.g., selected lymphocyte antibody method ("SLAM") (U.S. Pat. No. 5,627,052, Wen et al. (1987) *J. Immunol.* 17:887-892; Babcook et al. (1996) *Proc. Natl. Acad. Sci. USA* 93:7843-7848); gel microdroplet and flow cytometry (Powell et al. (1990) Biotechnol. 8:333-337; One Cell Systems, (Cambridge, Mass).; Gray et al. (1995) J. Imm. Meth. 182:155-163; Kenny et al. (1995) Bio/Technol. 13:787-790); B-cell selection (Steenbakkers et al. (1994) *Molec. Biol. Reports* 19:125-134 (1994)).

An affinity matured antibody may be produced by any one of a number of procedures that are known in the art. For example, see Marks et al., *BioTechnology,* 10: 779-783 (1992) describes affinity maturation by VH and VL domain shuffling. Random mutagenesis of CDR and/or framework residues is described by Barbas et al., *Proc. Nat. Acad. Sci. USA,* 91: 3809-3813 (1994); Schier et al., Gene, 169: 147-155 (1995); Yelton et al., *J. Immunol.,* 155: 1994-2004 (1995); Jackson et al., *J. Immunol.,* 154(7): 3310-3319 (1995); Hawkins et al, *J. Mol. Biol.,* 226: 889-896 (1992). Selective mutation at selective mutagenesis positions and at contact or hypermutation positions with an activity enhancing amino acid residue is described in U.S. Pat. No. 6,914,128 B1.

Antibody variants can also be prepared using delivering a polynucleotide encoding an antibody to a suitable host such as to provide transgenic animals or mammals, such as goats, cows, horses, sheep, and the like, that produce such antibodies in their milk. These methods are known in the art and are described for example in U.S. Pat. Nos. 5,827,690; 5,849,992; 4,873,316; 5,849,992; 5,994,616; 5,565,362; and 5,304,489.

Antibody variants also can be prepared by delivering a polynucleotide to provide transgenic plants and cultured plant cells (e.g., but not limited to tobacco, maize, and duckweed) that produce such antibodies, specified portions or variants in the plant parts or in cells cultured therefrom. For example, Cramer et al. (1999) *Curr. Top. Microbiol. Immunol.* 240:95-118 and references cited therein, describe the production of transgenic tobacco leaves expressing large amounts of recombinant proteins, e.g., using an inducible promoter. Transgenic maize have been used to express mammalian proteins at commercial production levels, with biological activities equivalent to those produced in other recombinant systems or purified from natural sources. See, e.g., Hood et al., *Adv. Exp. Med. Biol.* (1999) 464:127-147 and references cited therein. Antibody variants have also been produced in large amounts from transgenic plant seeds including antibody fragments, such as single chain antibodies (scFv's), including tobacco seeds and potato tubers. See, e.g., Conrad et al. (1998) *Plant Mol. Biol.* 38:101-109 and reference cited therein. Thus, antibodies can also be produced using transgenic plants, according to known methods.

Antibody derivatives can be produced, for example, by adding exogenous sequences to modify immunogenicity or reduce, enhance or modify binding, affinity, on-rate, off-rate, avidity, specificity, half-life, or any other suitable characteristic. Generally, part or all of the non-human or human CDR sequences are maintained while the non-human sequences of the variable and constant regions are replaced with human or other amino acids.

Small antibody fragments may be diabodies having two antigen-binding sites, wherein fragments comprise a heavy chain variable domain (VH) connected to a light chain variable domain (VL) in the same polypeptide chain (VH VL). See for example, EP 404,097; WO 93/11161; and Hollinger et al., (1993) *Proc. Natl. Acad. Sci. USA* 90:6444-6448. By using a linker that is too short to allow pairing between the two domains on the same chain, the domains are forced to pair with the complementary domains of another chain and create two antigen-binding sites. See also, U.S. Pat. No. 6,632,926 to Chen et al. which is hereby incorporated by reference in its entirety and discloses antibody variants that have one or more amino acids inserted into a hypervariable region of the parent antibody and a binding affinity for a target antigen which is at least about two fold stronger than the binding affinity of the parent antibody for the antigen.

The antibody may be a linear antibody. The procedure for making a linear antibody is known in the art and described in Zapata et al., (1995) *Protein Eng.* 8(10):1057-1062. Briefly, these antibodies comprise a pair of tandem Fd segments (VH-CH1-VH-CH1) which form a pair of antigen binding regions. Linear antibodies can be bispecific or monospecific.

The antibodies may be recovered and purified from recombinant cell cultures by known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be used for purification.

It may be useful to detectably label the antibody. Methods for conjugating antibodies to these agents are known in the art. For the purpose of illustration only, antibodies can be labeled with a detectable moiety such as a radioactive atom, a chromophore, a fluorophore, or the like. Such labeled antibodies can be used for diagnostic techniques, either in vivo, or in an isolated test sample. They can be linked to a cytokine, to a ligand, to another antibody. Suitable agents for coupling to antibodies to achieve an anti-tumor effect include cytokines, such as interleukin 2 (IL-2) and Tumor Necrosis Factor (TNF); photosensitizers, for use in photodynamic therapy, including aluminum (III) phthalocyanine tetrasulfonate, hematoporphyrin, and phthalocyanine; radionuclides, such as iodine-131 (131I), yttrium-90 (90Y), bismuth-212 (212Bi), bismuth-213 (213Bi), technetium-99m (99mTc), rhenium-186 (186Re), and rhenium-188 (188Re); antibiotics, such as doxorubicin, adriamycin, daunorubicin, methotrexate, daunomycin, neocarzinostatin, and carboplatin; bacterial, plant, and other toxins, such as diphtheria toxin, *pseudomonas* exotoxin A, staphylococcal enterotoxin A, abrin-A toxin, ricin A (deglycosylated ricin A and native ricin A), TGF-alpha toxin, cytotoxin from chinese cobra (*Naja atra*), and gelonin (a plant toxin); ribosome inactivating proteins from plants, bacteria and fungi, such as restrictocin (a ribosome inactivating protein produced by *Aspergillus restrictus*), saporin (a ribosome inactivating protein from *Saponaria officinalis*), and RNase; tyrosine kinase inhibitors; 1y207702 (a difluorinated purine nucleoside); liposomes containing anti cystic agents (e.g., antisense oligonucleotides, plasmids which encode for toxins, methotrexate, etc.); and other antibodies or antibody fragments, such as F(ab).

Antibody production via the use of hybridoma technology, the selected lymphocyte antibody method (SLAM), transgenic animals, and recombinant antibody libraries is described in more detail below.

A sample, as defined herein, is "suspected" of containing HBV if the sample is obtained from a subject, preferably a human, suspected of being infected with HBV. A subject is suspected of being infected with HBV if the subject has an increased risk for HBV. An infant born to a mother infected with HBV is at a high risk of HBV infection. Other high-risk factors for HBV infection include, for example, intravenous drug use, hemophilia, high-risk sexual activity, hemodialysis, needle stick injury in health care staff, and body piercing and tattooing.

The sample can be any suitable sample obtained from any suitable subject, typically a mammal (e.g., a human). The sample may be obtained from any biological source, such as, a cervical, vaginal or anal swab or brush, or a physiological fluid including, but not limited to, whole blood, serum, plasma, interstitial fluid, saliva, ocular lens fluid, cerebral spinal fluid, sweat, urine, milk, ascites fluid, mucous, nasal fluid, sputum, synovial fluid, peritoneal fluid, vaginal fluid, menses, amniotic fluid, semen, and the like. The sample can be obtained from the subject using routine techniques known to those skilled in the art, and the sample may be used directly as obtained from the biological source or following a pretreatment to modify the character of the sample. Such pretreatment may include, for example, preparing plasma from blood, diluting viscous fluids, filtration, precipitation, dilution, distillation, mixing, concentration, inactivation of interfering components, the addition of reagents, lysing, etc.

a. Aptamers

The methods of the present disclosure include the use of aptamers to detect or identify one or more HBV biomarkers. Aptamers are suitable for use in developing probes having high affinity and selectivity for target molecules, such as HBV peptide biomarkers. Aptamers include single-stranded DNA (ssDNA), RNA, or modified nucleic acids, which have the ability to bind specifically to their targets, which range from small organic molecules to proteins and peptides. The basis for target recognition is the tertiary structures formed by the single-stranded oligonucleotides, as known in the art. In some embodiments, aptamers used to detect or identify one or more HBV biomarkers can be obtained through an in vitro selection process known as SELEX, in which aptamers are selected from a library of random sequences of synthetic DNA or RNA by repetitive binding of the oligonucleotides to target molecules.

In some embodiments, nucleic acids that constitute an aptamer library mixture used for screening for candidate HBV biomarker capture agents can be single-stranded DNA or RNA with or without chemical modifications. The introduction of additional chemical entities into DNA during the selection process can include, for example, the use of a 5-alkyne modified nucleobase, (e.g., thymine). Additionally, 5-C8-alkyne modified nucleotide-triphosphates, for example deoxythymidines, are commercially available or can be synthesized. Such 5-C8-alkyne modified nucleobases can be introduced into DNA by PCR. Such modifications can be further derivatized with so called bio-orthogonal chemistry, for example, using the Cu(I) catalyzed 1,3-dipolar cycloaddition of respective azides with the alkyne. Beside the Cu(I) catalysed azide-alkyne cycloaddition (CuAAC), copper-free strain-promoted azide-alkyne cycloaddition (SPAAC) reactions also are useful. In some embodiments involving cellular or living systems, the strain-promoted azide-alkyne cycloaddition can overcome toxicity issues associated with the use of Cu(I). Any number of desirable chemical modifications can be added to the oligonucleotide library used for screening purposes. Examples of such modifications include without limitation aliphatic-aromatic-, charged-, basic-, acidic, heteroaromatic-, sugar-kind of-, metal-containing- or peptide-residues.

In some embodiments, a nucleobase that is to be modified to contain an azide-alkyne chemical group can include an ethynyl-, propynyl- or butynyl-dU, dA, dC or dG nucleotide. In other embodiments, a nucleobase that is to be modified to contain an azide-alkyne chemical group may be an ethynyl-dU nucleotide, or an ethynyl-dA nucleotide, an ethynyl-dC nucleotide or an ethynyl-dG nucleotide. Nucleotide aptamer libraries with these example modifications can be used in various SELEX-based selection methods, in order to enhance the chemical diversity of DNA aptamer libraries. The starting, or candidate, mixture of nucleic acids can be modified such that at least 25%, 30%, 35%, 40%, 45%, 50%, 55%, 60%, 65%, 70%, 75%, 80%, 85%, 90%, 91%, 92%, 93%, 94%, 95%, 96%, 97%, 98%, at least 99%, or 100% of the members of the mixture are modified to comprise the functionalization introduced by click chemistry, for example. Less than 100% modification may allow for enhanced diversity by allowing certain positions in an oligonucleotide to be modified but not others, whereas 100% modification ensures consistency during the selection process. In some embodiments, different modifications are made at different positions in the oligonucleotide to further enhance diversity.

HBV biomarker-recognizing aptamers can be used in various methods to detect a presence or level of one or more HBV biomarker in a biological sample (e.g., biological entities of interest such as proteins, nucleic acids, or microvesicles). The aptamer can function as a binding agent or capture agent to assess presence or level of the cognate HBV biomarker. In various embodiments of the present disclosure directed to diagnostics and/or prognostics, one or more aptamers can be configured in a ligand-target based assay, where one or more aptamers can be contacted with a selected biological sample to allow the or more aptamer to associate with or binds to its target HBV biomarker molecule. Aptamers can also be used to identify a profile of multiple HBV biomarkers (a "biomarker" profile or signature) based on the biological samples assessed and biomarkers detected. A biomarker profile of a biological sample may comprise a presence, level or other characteristic of one or more biomarker of interest that can be assessed, including without limitation a presence, level, sequence, mutation, rearrangement, translocation, deletion, epigenetic modification, methylation, post-translational modification, allele, activity, complex partners, stability, half-life, and the like.

Biomarker profiles or signatures can be used to evaluate diagnostic and/or prognostic criteria such as presence of disease, disease staging, disease monitoring, disease stratification, or surveillance for detection, metastasis or recurrence or progression of disease. For example, methods of the present disclosure can include methods for correlating an HBV biomarker profile to a selected condition or disease. A biomarker profile can also be used clinically in making decisions concerning treatment modalities including therapeutic intervention. Biomarker profiles based on aptamer detection, identification, and/or quantification can further be used clinically to make treatment decisions, including whether to alter the course of treatment, such as administering a different HBV therapeutic to the subject.

b. Assay Variations

The disclosed methods of determining the presence or amount of analyte of interest (e.g., HBV biomarker) present in a sample may be as described herein. The methods may also be adapted in view of other methods for analyzing analytes. Examples of well-known variations include, but are not limited to, immunoassay, such as sandwich immunoassay (e.g., monoclonal-monoclonal sandwich immunoassays, monoclonal-polyclonal sandwich immunoassays, including enzyme detection (enzyme immunoassay (EIA) or enzyme-linked immunosorbent assay (ELISA), competitive inhibition immunoassay (e.g., forward and reverse), enzyme multiplied immunoassay technique (EMIT), a competitive binding assay, bioluminescence resonance energy transfer (BRET), one-step antibody detection assay, homogeneous assay, heterogeneous assay, capture on the fly assay, etc.

i. Immunoassay

The analyte of interest, and/or peptides of fragments thereof (e.g., HBV biomarker and/or peptides or fragments thereof), may be analyzed using HBV biomarker antibodies in an immunoassay. The presence or amount of analyte (e.g., HBV biomarker) can be determined using antibodies and detecting specific binding to the analyte. For example, the antibody, or antibody fragment thereof, may specifically bind to the analyte. If desired, one or more of the antibodies can be used in combination with one or more commercially available monoclonal/polyclonal antibodies. Such antibodies are available from companies such as R&D Systems, Inc. (Minneapolis, MN) and Enzo Life Sciences International, Inc. (Plymouth Meeting, PA).

The presence or amount of analyte (e.g., HBV biomarker) present in a body sample may be readily determined using an immunoassay, such as sandwich immunoassay (e.g., monoclonal-monoclonal sandwich immunoassays, monoclonal-polyclonal sandwich immunoassays, including radioisotope detection (radioimmunoassay (RIA)) and enzyme detection (enzyme immunoassay (EIA) or enzyme-linked immunosorbent assay (ELISA) (e.g., Quantikine ELISA assays, R&D Systems, Minneapolis, MN)). An example of a point-of-care device that can be used is i-STAT® (Abbott, Laboratories, Abbott Park, Ill.). Other methods that can be used include a chemiluminescent microparticle immunoassay, including one employing the ARCHITECT® automated analyzer (Abbott Laboratories, Abbott Park, Ill.), as an example. Other methods include, for example, mass spectrometry, and immunohistochemistry (e.g., with sections from tissue biopsies), using anti-analyte (e.g., anti-HBV biomarker) antibodies (monoclonal, polyclonal, chimeric, humanized, human, etc.) or antibody fragments thereof against analyte (e.g., HBV biomarker). Other methods of detection include those described in, for example, U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, each of which is hereby incorporated by reference in its entirety. Specific immunological binding of the antibody to the analyte can be detected via direct labels, such as fluorescent or luminescent tags, metals and radionuclides attached to the antibody or via indirect labels, such as alkaline phosphatase or horseradish peroxidase.

The use of immobilized antibodies or antibody fragments thereof may be incorporated into the immunoassay. The antibodies may be immobilized onto a variety of supports, such as magnetic or chromatographic matrix particles, the surface of an assay plate (such as microtiter wells), pieces of a solid substrate material, and the like. An assay strip can be prepared by coating the antibody or plurality of antibodies in an array on a solid support. This strip can then be dipped into the test sample and processed quickly through washes and detection steps to generate a measurable signal, such as a colored spot.

A homogeneous format may be used. For example, after the test sample is obtained from a subject, a mixture is prepared. The mixture contains the test sample being assessed for analyte (e.g., HBV biomarker) and a specific binding partner. The order in which the test sample and the specific binding partner are added to form the mixture is not critical. The test sample is simultaneously contacted with the specific binding partner. In some embodiments, the specific binding partner and any HBV biomarker contained in the test sample may form a specific binding partner-analyte (e.g., HBV biomarker)-antigen complex. The specific binding partner may be an anti-analyte antibody (e.g., anti-HBV biomarker antibody that binds to an epitope having an amino acid sequence comprising at least three contiguous (3) amino acids of the HBV biomarker. Moreover, the specific binding partner may be labeled with or contains a detectable label as described above.

A heterogeneous format may be used. For example, after the test sample is obtained from a subject, a first mixture is prepared. The mixture contains the test sample being assessed for analyte (e.g., HBV biomarker) and a first specific binding partner, wherein the first specific binding partner and any HBV biomarker contained in the test sample form a first specific binding partner-analyte (e.g., HBV biomarker)-antigen complex. The first specific binding partner may be an anti-analyte antibody (e.g., anti-HBV biomarker antibody that binds to an epitope having an amino acid sequence comprising at least three contiguous (3) amino acids of the HBV biomarker. The order in which the test sample and the first specific binding partner are added to form the mixture is not critical.

The first specific binding partner may be immobilized on a solid phase. The solid phase used in the immunoassay (for the specific binding partner) can be any solid phase known in the art, such as, but not limited to, a magnetic particle, a bead, a test tube, a microtiter plate, a cuvette, a membrane, a scaffolding molecule, a film, a filter paper, a disc, and a chip. In those embodiments where the solid phase is a bead, the bead may be a magnetic bead or a magnetic particle. Magnetic beads/particles may be ferromagnetic, ferrimagnetic, paramagnetic, superparamagnetic or ferrofluidic. Exemplary ferromagnetic materials include Fe, Co, Ni, Gd, Dy, $CrO_2$, MnAs, MnBi, EuO, and NiO/Fe. Examples of ferrimagnetic materials include $NiFe_2O_4$, $CoFe_2O_4$, $Fe_3O_4$ (or $FeO \cdot Fe_2O_3$). Beads can have a solid core portion that is magnetic and is surrounded by one or more non-magnetic layers. Alternately, the magnetic portion can be a layer around a non-magnetic core. The solid support on which the first specific binding member is immobilized may be stored in dry form or in a liquid. The magnetic beads may be subjected to a magnetic field prior to or after contacting with the sample with a magnetic bead on which the first specific binding member is immobilized.

After the mixture containing the first specific binding partner-analyte (e.g., HBV biomarker) antigen complex is formed, any unbound analyte (e.g., HBV biomarker) is removed from the complex using any technique known in the art. For example, the unbound analyte can be removed by washing. Desirably, however, the first specific binding partner is present in excess of any analyte present in the test sample, such that all analyte that is present in the test sample is bound by the first specific binding partner.

After any unbound analyte (e.g., HBV biomarker) is removed, a second specific binding partner is added to the mixture to form a first specific binding partner-analyte of interest (e.g., HBV biomarker)-second specific binding partner complex. The second specific binding partner may be an anti-analyte antibody (e.g., HBV biomarker antibody that binds to an epitope having an amino acid sequence comprising at least three contiguous (3) amino acids of the HBV biomarker. Moreover, the second specific binding partner is labeled with or contains a detectable label as described above.

The use of immobilized antibodies or antibody fragments thereof may be incorporated into the immunoassay. The antibodies may be immobilized onto a variety of supports, such as magnetic or chromatographic matrix particles (such as a magnetic bead), latex particles or modified surface latex particles, polymer or polymer film, plastic or plastic film, planar substrate, the surface of an assay plate (such as microtiter wells), pieces of a solid substrate material, and the like. An assay strip can be prepared by coating the antibody or plurality of antibodies in an array on a solid support. This strip can then be dipped into the test sample and processed quickly through washes and detection steps to generate a measurable signal, such as a colored spot.

ii. Sandwich Immunoassay

A sandwich immunoassay measures the amount of antigen between two layers of antibodies (i.e., at least one capture antibody) and a detection antibody (i.e., at least one detection antibody). The capture antibody and the detection antibody bind to different epitopes on the antigen, e.g., analyte of interest such as a HBV biomarker). Desirably, binding of the capture antibody to an epitope does not interfere with binding of the detection antibody to an epitope. Either monoclonal or polyclonal antibodies may be used as the capture and detection antibodies in the sandwich immunoassay.

Generally, at least two antibodies are employed to separate and quantify analyte (e.g., HBV biomarker) in a test sample. More specifically, the at least two antibodies bind to certain epitopes of analyte forming an immune complex which is referred to as a "sandwich." One or more antibodies can be used to capture the analyte in the test sample (these antibodies are frequently referred to as a "capture" antibody or "capture" antibodies) and one or more antibodies is used to bind a detectable (namely, quantifiable) label to the sandwich (these antibodies are frequently referred to as the "detection" antibody or "detection" antibodies). In a sandwich assay, the binding of an antibody to its epitope desirably is not diminished by the binding of any other antibody in the assay to its respective epitope. Antibodies are selected so that the one or more first antibodies brought into contact with a test sample suspected of containing analyte do not bind to all or part of an epitope recognized by the second or subsequent antibodies, thereby interfering with the ability of the one or more second detection antibodies to bind to the analyte.

The antibodies may be used as a first antibody in said immunoassay. The antibody immunospecifically binds to epitopes on analyte (e.g., HBV biomarker). In addition to the antibodies of the present disclosure, said immunoassay may comprise a second antibody that immunospecifically binds to epitopes that are not recognized or bound by the first antibody.

A test sample suspected of containing analyte (e.g., HBV biomarker) can be contacted with at least one first capture antibody (or antibodies) and at least one second detection antibodies either simultaneously or sequentially. In the sandwich assay format, a test sample suspected of containing analyte is first brought into contact with the at least one first capture antibody that specifically binds to a particular epitope under conditions which allow the formation of a first antibody-analyte antigen complex. If more than one capture antibody is used, a first multiple capture antibody-HBV biomarker antigen complex is formed. In a sandwich assay, the antibodies, such as the at least one capture antibody, are used in molar excess amounts of the maximum amount of analyte expected in the test sample. For example, from about 5 μg/mL to about 1 mg/mL of antibody per ml of microparticle coating buffer may be used.

iii. Single Molecule Detection

The methods and kits as described herein may also involve single molecule counting. In certain embodiments, a method for analyte analysis may involve assessing an analyte present in a sample. In certain embodiments, the assessing may be used for determining presence of and/or concentration of an analyte in a sample. In certain embodiments, the method may also be used for determining presence of and/or concentration of a plurality of different analytes present in a sample.

Any device known in the art that allows for the detection of a single molecule of one or more analytes of interest can be used in the systems described herein. For example, the device can be a microfluidics device, digital microfluidics device (DMF), a surface acoustic wave based microfluidic device (SAW), an integrated DMF and analyte detection device, an integrated SAW and analyte detection device, or robotics based assay processing unit. Examples of other devices that can be used include the Quanterix SIMOA™ (Lexington, MA), Singulex's single molecule counting (SMC™) technology (Alameda, CA, see for example, U.S. Pat. No. 9,239,284, the contents of which are herein incorporated by reference), etc.

Other methods of detection include the use of or can be adapted for use on a nanopore device or nanowell device. Examples of nanopore devices are described in International Patent Publication No. WO 2016/161402, which is hereby incorporated by reference in its entirety. Examples of nanowell device are described in International Patent Publication No. WO 2016/161400, which is hereby incorporated by reference in its entirety.

The methods and kits as described herein can involve mass spectrometry using DIA-MS, DDA-MS or SRM/MRM-MS or PRM-MS. In certain embodiments, methods for analyte analysis can involve assessing a sample for the presence of an analyte. In certain embodiments, assessing a sample for the presence of an analyte can be used for determining presence of and/or concentration of an analyte or a fragment in a sample. In certain embodiments, a method can also be used for determining presence of and/or concentration of a plurality of different analytes or analyte fragments present in a sample. Quantification can be performed using internal control proteins or peptide fragments.

6. Samples

As used herein, "sample", "test sample", "biological sample" refer to fluid sample containing or suspected of containing an HBV biomarker. The sample may be derived from any suitable source. In some cases, the sample may comprise a liquid, fluent particulate solid, or fluid suspension of solid particles. In some cases, the sample may be processed prior to the analysis described herein. For example, the sample may be separated or purified from its source prior to analysis; however, in certain embodiments, an unprocessed sample containing an HBV biomarker may be assayed directly. In one example, the source containing an HBV biomarker is a human bodily substance (e.g., bodily fluid, blood such as whole blood, serum, plasma, urine, saliva, sweat, sputum, semen, mucus, lacrimal fluid, lymph fluid, amniotic fluid, interstitial fluid, lung lavage, cerebrospinal fluid, feces, tissue, organ, or the like). Tissues may include, but are not limited to skeletal muscle tissue, liver tissue, lung tissue, kidney tissue, myocardial tissue, brain tissue, bone marrow, cervix tissue, skin, etc. The sample may be a liquid sample or a liquid extract of a solid sample. In certain cases, the source of the sample may be an organ or tissue, such as a biopsy sample, which may be solubilized by tissue disintegration/cell lysis.

A wide range of volumes of the fluid sample may be analyzed. In a few exemplary embodiments, the sample volume may be about 0.5 nL, about 1 nL, about 3 nL, about 0.01 μL, about 0.1 μL, about 1 μL, about 5 μL, about 10 μL, about 100 μL, about 1 mL, about 5 mL, about 10 mL, or the like. In some cases, the volume of the fluid sample is between about 0.01 μL and about 10 mL, between about 0.01 μL and about 1 mL, between about 0.01 μL and about 100 μL, or between about 0.1 μL and about 10 μL.

In some cases, the fluid sample may be diluted prior to use in an assay. For example, in embodiments where the source containing an HBV biomarker is a human body fluid (e.g., blood, serum), the fluid may be diluted with an appropriate solvent (e.g., a buffer such as PBS buffer). A fluid sample may be diluted about 1-fold, about 2-fold, about 3-fold, about 4-fold, about 5-fold, about 6-fold, about 10-fold, about 100-fold, or greater, prior to use. In other cases, the fluid sample is not diluted prior to use in an assay.

In some cases, the sample may undergo pre-analytical processing. Pre-analytical processing may offer additional functionality such as nonspecific protein removal and/or effective yet cheaply implementable mixing functionality. General methods of pre-analytical processing may include the use of electrokinetic trapping, AC electrokinetics, surface acoustic waves, isotachophoresis, dielectrophoresis, electrophoresis, or other pre-concentration techniques known in the art. In some cases, the fluid sample may be concentrated prior to use in an assay. For example, in embodiments where the source containing an HBV biomarker is a human body fluid (e.g., blood, serum), the fluid may be concentrated by precipitation, evaporation, filtration, centrifugation, or a combination thereof. A fluid sample may be concentrated about 1-fold, about 2-fold, about 3-fold, about 4-fold, about 5-fold, about 6-fold, about 10-fold, about 100-fold, or greater, prior to use.

It may be desirable to include a control. The control may be analyzed concurrently with the sample from the subject as described above. The results obtained from the subject sample can be compared to the results obtained from the control sample. Standard curves may be provided, with which assay results for the sample may be compared. Such standard curves present levels of marker as a function of assay units, i.e., fluorescent signal intensity, if a fluorescent label is used. Using samples taken from multiple donors, standard curves can be provided for reference levels of an HBV biomarker in normal healthy tissue, as well as for "at-risk" levels of the HBV biomarker in tissue taken from donors, who may have one or more of the characteristics set forth above.

Thus, in view of the above, a method for determining the presence, amount, or concentration of an HBV biomarker in a test sample is provided. The method comprises assaying the test sample for an HBV biomarker by an immunoassay, for example, employing at least one capture antibody that binds to an epitope on an HBV biomarker and at least one detection antibody that binds to an epitope on an HBV biomarker which is different from the epitope for the capture antibody and optionally includes a detectable label, and comprising comparing a signal generated by the detectable label as a direct or indirect indication of the presence, amount or concentration of an HBV biomarker in the test sample to a signal generated as a direct or indirect indication of the presence, amount or concentration of an HBV biomarker in a calibrator. The calibrator is optionally, and in some embodiments, is part of a series of calibrators in which each of the calibrators differs from the other calibrators in the series by the concentration of the HBV biomarker.

7. Kits and Systems

In some embodiments, the present disclosure further provides kits and systems for detecting the presence, level, or status of HBcAg and/or P-HBcAg in a sample. In some embodiments, provided herein is a kit or a system comprising reagents for detecting the presence, level, or status of HBcAg. In some embodiments, provided herein is a kit or a system comprising reagents for detecting the presence, level, or status of P-HBcAg. In some embodiments, provided herein is a kit or a system comprising reagents for detecting the presence, level, or status of HBcAg and P-HBcAg. In some embodiments, the kits or systems find use in multiplex and/or automated analysis methods. Exemplary reagents include, but are not limited to, nucleic acid primers, nucleic acid probes, antibodies, colorimetric reagents, enzymes, buffers, etc.

Optionally, the kit can also contain at least one calibrator or control. Any calibrator or control can be included in the kit.

Thus, the present disclosure further provides for diagnostic and quality control kits comprising one or more antibodies or other detection reagents. Optionally the assays, kits and kit components of the disclosure are optimized for use on commercial platforms (e.g., immunoassays on the Prism®, AxSYM®, ARCHITECT® and EIA (Bead) platforms of Abbott Laboratories, Abbott Park, Ill., as well as other commercial and/or in vitro diagnostic assays). Additionally, the assays, kits and kit components can be employed in other formats, for example, on electrochemical or other hand-held or point-of-care assay systems. The present disclosure is, for example, applicable to the commercial Abbott Point of Care (i-STAT®, Abbott Laboratories, Abbott Park, Ill.) electrochemical immunoassay system. Immunosensors and methods of operating them in single-use test devices are described, for example, in U.S. Patent Applications 20030170881, 20040018577, 20050054078 and 20060160164 which are incorporated herein by reference. Additional background on the manufacture of electrochemical and other types of immunosensors is found in U.S. Pat. No. 5,063,081 which is also incorporated by reference for its teachings regarding same.

Optionally the kits include quality control reagents (for example, sensitivity panels, calibrators, and positive controls). Preparation of quality control reagents is well known in the art, and is described, e.g., on a variety of immunodiagnostic or nucleic acid product insert sheets.

In another embodiment, the present disclosure provides for a quality control kit comprising one or more antibodies described herein for use as a sensitivity panel to evaluate assay performance characteristics and/or to quantitate and monitor the integrity of the antigen(s) or nucleic acids used in the assay.

The kits can optionally include other reagents required to conduct a diagnostic assay or facilitate quality control evaluations, such as buffers, salts, enzymes, enzyme co-factors, substrates, detection reagents, and the like. Other components, such as buffers and solutions for the isolation and/or treatment of a test sample (e.g., pretreatment reagents), may also be included in the kit. The kit may additionally include one or more other controls. One or more of the components of the kit may be lyophilized and the kit may further comprise reagents suitable for the reconstitution of the lyophilized components.

The various components of the kit optionally are provided in suitable containers. As indicated above, one or more of the containers may be a microtiter plate. The kit further can include containers for holding or storing a sample (e.g., a container or cartridge for a blood or urine sample). Where appropriate, the kit may also optionally contain reaction vessels, mixing vessels and other components that facilitate the preparation of reagents or the test sample. The kit may also include one or more instruments for assisting with obtaining a test sample, such as a syringe, pipette, forceps, measured spoon, or the like.

The kit further can optionally include instructions for use, which may be provided in paper form or in computer-readable form, such as a disc, CD, DVD or the like.

The disclosure as described herein also can be adapted for use in a variety of automated and semi-automated systems (including those wherein the solid phase comprises a microparticle), as described, e.g., in U.S. Pat. Nos. 5,089,424 and 5,006,309, and as, e.g., commercially marketed by Abbott Laboratories (Abbott Park, Ill.) including but not limited to Abbott's ARCHITECT®, AxSYM®, IMX, PRISM®, and Quantum II instruments, as well as other platforms. Moreover, the disclosure optionally is adaptable for the Abbott Laboratories commercial Point of Care (i-STAT™) electrochemical immunoassay system for performing sandwich immunoassays. Immunosensors, and their methods of manufacture and operation in single-use test devices are described, for example in, U.S. Pat. No. 5,063,081, U.S. Patent Application 2003/0170881, U.S. Patent Application 2004/0018577, U.S. Patent Application 2005/0054078, and U.S. Patent Application 2006/0160164, which are incorporated in their entireties by reference for their teachings regarding same.

8. HBV Therapeutics

For any of the methods described herein, the method may further comprise identifying a treatment for chronic HBV infection and administering the treatment to the subject. For example, in some embodiments the method comprises detecting the presence, level, or status of HBcAg and/or P-HBcAg in a sample obtained from a subject diagnosed with HBV, selecting an appropriate treatment based upon the presence, level, or status of HBcAg and/or P-HBcAg in the sample, and providing the treatment to the subject. In some embodiments, the subject has received a treatment for chronic HBV. In some embodiments, the subject has received a treatment for chronic HBV and methods described herein are employed to monitor responsiveness to the treatment.

For any of the methods described herein, the treatment may be any suitable HBV treatment, including those described in detail below.

The treatment is an agent that impacts reverse transcription of HBV RNA (e.g. pgRNA) to HBV DNA. For example, some HBV treatments such as nucleoside inhibitors inhibit pgRNA reverse transcription, and therefore reduce the amount of HBV DNA (e.g. infectious particles) released from the cell. Accordingly, such treatments can be determined to be efficacious or not efficacious in a subject by measuring HBcAg, which is indicative of the amount of infectious DNA particles in a sample. However, such HBV treatments do not interfere with the process of transcribing cccDNA to pgRNA, and accordingly these treatments do not reduce the amount of HBV RNA (e.g. pgRNA) secreted from the cell in "empty" or "non-infectious" particles. Accordingly, measurements of P-HBcAg, which correlate to non-infectious HBV particles, should be unaffected by such a treatment.

Therapeutic agents used to treat HBV include any of the following, as described further herein. Generally, the aim and/or ultimate goal of such therapeutic agents is to silence and/or eliminate covalently closed circular DNA (cccDNA). cccDNA is a DNA structure that arises in the cell nucleus during the propagation of HBV. cccDNA is able to form a stable minichromosome within the nucleus of infected cells. cccDNA can serve as a template for viral replication, which allows for the production of viral antigens. Chronic HBV infection is characterized by the persistence of the cccDNA minichromosome in the nuclei of hepatocytes of an infected subject. Current HBV treatments are unable to eliminate the cccDNA minichrososome from host cells, and as such elimination of cccDNA is considered a "functional cure" in subjects suffering from HBV. Thus, a variety of therapeutic agents that are useful in silencing and/or eliminating cccDNA can be used in the methods described herein. In some embodiments, an HBV therapeutic includes tenofovir disoproxil fumarate, emtricitabine (Truvada®), adefovir, clevudine, ABX-203, lamivudine, PEG-IFNalpha, ABX-203, adefovir, PEG-IFNalpha and GBV-015. In some embodiments, an HBV therapeutic includes HBV DNA polymerase inhibitors such as besifovir, entecavir (Baraclude®), adefovir (Hepsera®), tenofovir disoproxil fumarate (Viread®), tenofovir alafenamide, tenofovir, tenofovir disoproxil, tenofovir alafenamide fumarate, tenofovir alafenamide hemifumarate, tenofovir dipivoxil, tenofovir dipivoxil fumarate, tenofovir octadecyloxyethyl ester, telbivudine (Tyzeka®), pradefovir, Clevudine, emtricitabine (Emtriva®), ribavirin, lamivudine (Epivir-HBV®), phosphazide, famciclovir, SNC-019754, FMCA, fusolin, AGX-1009 and metacavir.

In some embodiments, an HBV therapeutic includes immunomodulators such as rintatolimod, imidol hydrochloride, ingaron, dermaVir, plaquenil (hydroxychloroquine), proleukin, hydroxyurea, mycophenolate mofetil (MPA) and its ester derivative mycophenolate mofetil (MMF), WF-10, ribavirin, IL-12, polymer polyethyleneimine (PEI), Gepon, VGV-1, MOR-22, BMS-936559 and IR-103. In some embodiments, an HBV therapeutic includes toll-like receptor 7 modulators such as GS-9620, GSK-2245035, imiquimod, resiquimod, DSR-6434, DSP-3025, IMO-4200, MCT-465, 3M-051, SB-9922, 3M-052, Limtop, TMX-30X, TMX-202 RG-7863 and RG-7795. In some embodiments, an HBV therapeutic includes nucleic acid polymers (NAPs), such as, for example, REP 2139.

Toll-like receptor 8 modulators include motolimod, resiquimod, 3M-051, 3M-052, MCT-465, IMO-4200, VTX-763, VTX-1463. Toll-like receptor 3 modulators include rintatolimod, poly-ICLC, MCT-465, MCT-475, Riboxxon, Riboxxim and ND-1.1. Interferon alpha receptor ligands include interferon alpha-2b (Intron A®), pegylated interferon alpha-2a (Pegasys®), interferon alpha 1b (Hapgen®), Veldona, Infradure, Roferon-A, YPEG-interferon alfa-2a (YPEG-rhIFNalpha-2a), P-1101, Algeron, Alfarona, Ingaron (interferon gamma), rSIFN-co (recombinant super compound interferon), Ypeginterferon alfa-2b (YPEG-rhIFNalpha-2b), MOR-22, peginterferon alfa-2b (PEG-Intron®), Bioferon, Novaferon, Inmutag (IFN), Multiferon®, interferon alfa-n1 (Humoferon®), interferon beta-1a (Avonex®), Shaferon, interferon alfa-2b (AXXO), Alfaferone, interferon alfa-2b (BioGeneric Pharma), interferon-alpha 2 (CJ), Laferonum, VIPEG, BLAUFERON-B, BLAUFERON-A, Intermax Alpha, Realdiron, Lanstion, Pegaferon, PDferon-B, interferon alfa-2b (IFN, Laboratories Bioprofarma), alfainterferona 2b, Kalferon, Pegnano, Feronsure, PegiHep, interferon alfa 2b (Zydus-Cadila), Optipeg A, Realfa 2B, Reliferon, interferon alfa-2b (Amega), interferon alfa-2b (Virchow), peginterferon alfa-2b (Amega), Reaferon-EC, Proquiferon, Uniferon, Urifron, interferon alfa-2b (Changchun Institute of Biological Products), Anterferon, Shanferon, Layfferon, Shang Sheng Lei Tai, INTEFEN, SINOGEN, Fukangtai, Pegstat, rHSA-IFN alpha-2b and Interapo (Interapa).

Hyaluronidase inhibitors include astodrimer. HBsAg inhibitors include HBF-0259, PBHB V-001, PBHBV-2-15, PBHBV-2-1, REP 9 AC, REP-9C and REP 9AC. Toll like receptor 9 modulators include CYT003. Cyclophilin inhibitors include OCB-030, SCY-635 and NVP-018. HBV Prophylactic vaccines include Hexaxim, Heplisav, Mosquirix, DTwP-HBV vaccine, Bio-Hep-B, D/T/P/HBV/M (LBVP-0101; LBVW-0101), DTwP-Hepb-Hib-IPV vaccine, Heberpenta L, DTwP-HepB-Hib, V-419, CVI-HBV-001, Tetrabhay, hepatitis B prophylactic vaccine (Advax Super D), Hepatrol-07, GSK-223192A, Engerix B®, recombinant hepatitis B vaccine (intramuscular, Kangtai Biological Products), recombinant hepatitis B vaccine (Hansenual polymorpha yeast, intramuscular, Hualan Biological Engineering), Bimmugen, Euforavac, Eutravac, anrix-DTaP-IPV-Hep B, Infanrix-DTaP-IPV-Hep B-Hib, Pentabio Vaksin DTP-HB-Hib, Comvac 4, Twinrix, Euvax-B, Tritanrix HB, Infanrix Hep B, Comvax, DTP-Hib-HBV vaccine, DTP-HBV vaccine, Yi Tai, Heberbiovac HB, Trivac HB, GerVax, DTwP-Hep B-Hib vaccine, Bilive, Hepavax-Gene, SUPERVAX, Comvac5, Shanvac-B, Hebsulin, Recombivax HB, Revac B mcf, Revac B+, Fendrix, DTwP-HepB-Hib, DNA-001, Shan6, rhHBsAG vaccine, and DTaP-rHB-Hib vaccine.

HBV Therapeutic vaccines include HBsAG-HBIG complex, Bio-Hep-B, NASVAC, abi-HB (intravenous), ABX-203, Tetrabhay, GX-110E, GS-4774, peptide vaccine (epsilonPA-44), Hepatrol-07, NASVAC (NASTERAP), IMP-321, BEVAC, Revac B mcf, Revac B+, MGN-1333, KW-2, CVI-HBV-002, AltraHepB, VGX-6200, FP-02, TG-1050, NU-500, HBV ax, im/TriGrid/antigen vaccine, Mega-CD40L-adjuvanted vaccine, HepB-v, NO-1800, recombinant VLP-based therapeutic vaccine (HBV infection, VLP Biotech), AdTG-17909, AdTG-17910 AdTG-18202, ChronVac-B, and Lm HBV.

HBV viral entry inhibitors include Myrcludex B. Antisense oligonucleotide targeting viral mRNA include ISIS-HBVRx. Interfering RNA, including short interfering RNAs (siRNA) can be used. For example, siRNA that can be used include TKM-HBV(TKM-HepB), ALN-HBV, SR-008, ddRNAi and ARC-520. Endonuclease modulators include PGN-514. Inhibitors of ribonucleotide reductase include Trimidox. Hepatitis B virus E antigen inhibitors include wogonin. HBV antibodies targeting the surface antigens of the hepatitis B virus include GC-1102, XTL-17, XTL-19, XTL-001, K-003 and fully human monoclonal antibody therapy (hepatitis B virus infection, Humabs BioMed). HBV antibodies including monoclonal antibodies and polyclonal antibodies include Zutectra, Shang Sheng Gan Di, Uman Big (Hepatitis B Hyperimmune), Omri-Hep-B, Nabi-HB, Hepatect CP, HepaGam B, igantibe, Niuliva, CT-P24, hepatitis B immunoglobulin (intravenous, pH4, HBV infection, Shanghai RAAS Blood Products) and Fovepta (BT-088). CCR2 chemokine antagonists include propagermanium. Thymosin agonists include Thymalfasin. Cytokines include recombinant IL-7, CYT-107, interleukin-2 (IL-2, Immunex); recombinant human interleukin-2 (Shenzhen Neptunus) and celmoleukin. Nucleoprotein inhibitors (HBV core or capsid protein inhibitors) include NVR-1221, NVR-3778, BAY 41-4109, morphothiadine mesilate and DVR-23. Stimulators of retinoic acid-inducible gene 1 include SB-9200, SB-40, SB-44, ORI-7246, ORI-9350, ORI-7537, ORI-9020, ORI-9198 and ORI-7170; (28) Stimulators of NOD2 selected from the group consisting of SB-9200. Recombinant thymosin alpha-1 include NL-004 and PEGylated thymosin alpha 1.

Hepatitis B virus replication inhibitors include isothiafludine, IQP-HBV, RM-5038 and Xingantie. PI3K inhibitors include idelalisib, AZD-8186, buparlisib, CLR-457, pictilisib, neratinib, rigosertib, rigosertib sodium, EN-3342, TGR-1202, alpelisib, duvelisib, UCB-5857, taselisib, XL-765, gedatolisib, VS-5584, copanlisib, CAI orotate, perifosine, RG-7666, GSK-2636771, DS-7423, panulisib, GSK-2269557, GSK-2126458, CUDC-907, PQR-309, INCB-040093, pilaralisib, BAY-1082439, puquitinib mesylate, SAR-245409, AMG-319, RP-6530, ZSTK-474, MLN-1117, SF-1126, RV-1729, sonolisib, LY-3023414, SAR-260301 and CLR-1401; (32) cccDNA inhibitors selected from the group consisting of BSBI-25.

PD-L1 inhibitors include MEDI-0680, RG-7446, durvalumab, KY-1003, KD-033, MSB-0010718C, TSR-042, ALN-PDL, STI-A1014 and BMS-936559. PD-1 inhibitors include nivolumab, pembrolizumab, pidilizumab, BGB-108 and mDX-400. BTK inhibitors include ACP-196, dasatinib, ibrutinib, PRN-1008, SNS-062, ONO-4059, BGB-3111, MSC-2364447, X-022, spebrutinib, TP-4207, HM-71224, KBP-7536 and AC-0025.

Other drugs for treating HBV include gentiopicrin (gentiopicroside), nitazoxanide, birinapant, NOV-205 (Molixan; BAM-205), Oligotide, Mivotilate, Feron, levamisole, Ka Shu Ning, Alloferon, WS-007, Y-101 (Ti Fen Tai), rSIFN-co, PEG-IIFNm, KW-3, BP-Inter-014, oleanolic acid, HepB-nRNA, cTP-5 (rTP-5), HSK-II-2, HEISCO-106-1, HEISCO-106, Hepbama, IBPB-006IA, Hepuyinfen, DasKloster 0014-01, Jiangantai (Ganxikang), picroside, GA5 NM-HBV, DasKloster-0039, hepulantai, IMB-2613, TCM-800B, reduced glutathione and ZH-2N.

In some embodiments, the HBV therapeutic comprises a capsid assembly modulator (CAM). A capsid assembly modulator refers to an agent that disrupts the encapsidation of pre-genomic RNA and can cause nucleocapsid disassembly, thereby disrupting multiple steps of HBV replication. In some embodiments, the CAM is JNJ-632, AT130, or BAY41-4109.

In some embodiments, an HBV therapeutic can be combined with one, two, three, four or more additional therapeutic agents. In certain embodiments, a compound disclosed herein, or a pharmaceutically acceptable salt thereof, is combined with two additional therapeutic agents. In other embodiments, a compound disclosed herein, or a pharmaceutically acceptable salt thereof, is combined with three additional therapeutic agents. In further embodiments, a compound disclosed herein, or a pharmaceutically acceptable salt thereof, is combined with four additional therapeutic agents. The one, two, three, four or more additional therapeutic agents can be different therapeutic agents selected from the same class of therapeutic agents, and/or they can be selected from different classes of therapeutic agents.

In one embodiment, an HBV therapeutic includes immunomodulators, toll-like receptor modulators (modulators of tlr1, tlr2, tlr3, tlr4, tlr5, tlr6, tlr7, tlr8, tlr9, tlr10, tlr11, tlr12 and tlr13), interferon alpha receptor ligands, hyaluronidase inhibitors, recombinant IL-7, HBsAg inhibitors, compounds targeting HBcAg, cyclophilin inhibitors, HB V therapeutic vaccines, HBV prophylactic vaccines HBV viral entry inhibitors, NTCP inhibitors, antisense oligonucleotide targeting viral mRNA, short interfering RNAs (siRNA), miRNA gene therapy agents, endonuclease modulators, inhibitors of ribonucleotide reductase, Hepatitis B virus E antigen inhibitors, recombinant scavenger receptor A (SRA) proteins, src kinase inhibitors, HBx inhibitors, cccDNA inhibitors, short synthetic hairpin RNAs (sshRNAs), HBV antibodies including HBV antibodies targeting the surface antigens of the hepatitis B virus and bispecific antibodies and “antibody-like” therapeutic proteins (such as DARTs®, Duobodies®, Bites®, XmAbs®, TandAbs®, Fab derivatives), CCR2 chemokine antagonists, thymosin agonists, cytokines, nucleoprotein inhibitors (HBV core or capsid protein inhibitors), stimulators of retinoic acid-inducible gene 1, stimulators of NOD2, stimulators of NODI, Arginase-1 inhibitors, STING agonists, PI3K inhibitors, lymphotoxin beta receptor activators, Natural Killer Cell Receptor 2B4 inhibitors, Lymphocyte-activation gene 3 inhibitors, CD160 inhibitors, cytotoxic T-lymphocyte-associated protein 4 inhibitors, CD 137 inhibitors, Killer cell lectin-like receptor subfamily G member 1 inhibitors, TIM-3 inhibitors, B- and T-lymphocyte attenuator inhibitors, CD305 inhibitors, PD-1 inhibitors, PD-L1 inhibitors, PEG-Interferon Lambda, recombinant thymosin alpha-1, BTK inhibitors, modulators of TIGIT, modulators of CD47, modulators of SIRPalpha, modulators of ICOS, modulators of CD27, modulators of CD70, modulators of OX40, modulators of NKG2D, modulators of Tim-4, modulators of B7-H4, modulators of B7-H3, modulators of NKG2A, modulators of GITR, modulators of CD160, modulators of HEVEM, modulators of CD161, modulators of Axl, modulators of Mer, modulators of Tyro, gene modifiers or editors such as CRISPR (including CRISPR Cas9), zinc finger nucleases or synthetic nucleases (TALENs), and Hepatitis B virus replication inhibitors.

In one embodiment, an HBV therapeutic includes HBsAg inhibitors, HBV therapeutic vaccines, HBV antibodies including HBV antibodies targeting the surface antigens of the hepatitis B virus and bispecific antibodies and “antibody-like” therapeutic proteins (such as DARTs®, Duobodies®, Bites®, XmAbs®, TandAbs®, Fab derivatives), cyclophilin inhibitors, stimulators of retinoic acid-inducible gene 1, PD-1 inhibitors, PD-L1 inhibitors, Arginase-1 inhibitors, PI3K inhibitors and stimulators of NOD2.

In one embodiment, an HBV therapeutic includes HBV viral entry inhibitors, NTCP inhibitors, HBx inhibitors, cccDNA inhibitors, HBV antibodies targeting the surface antigens of the hepatitis B virus, short interfering RNAs (siRNA), miRNA gene therapy agents, short synthetic hairpin RNAs (sshRNAs), and nucleoprotein inhibitors (HBV core or capsid protein inhibitors).

In one embodiment, an HBV therapeutic includes immunomodulators, toll-like receptor modulators (modulators of tlr1, tlr2, tlr3, tlr4, tlr5, tlr6, tlr7, tlr8, tlr9, tlr10, tlr11, tlr12 and tlr13), HBsAg inhibitors, HBV therapeutic vaccines, HBV antibodies including HBV antibodies targeting the surface antigens of the hepatitis B virus and bispecific antibodies and “antibody-like” therapeutic proteins (such as DARTs®, Duobodies®, Bites®, XmAbs®, TandAbs®, Fab derivatives), cyclophilin inhibitors, stimulators of retinoic acid-inducible gene 1, PD-1 inhibitors, PD-L1 inhibitors, Arginase-1 inhibitors, PI3K inhibitors and stimulators of NOD2, and one or two additional therapeutic agents selected from the group consisting of: HBV viral entry inhibitors, NTCP inhibitors, HBx inhibitors, cccDNA inhibitors, HBV antibodies targeting the surface antigens of the hepatitis B virus, short interfering RNAs (siRNA), miRNA gene therapy agents, short synthetic hairpin RNAs (sshRNAs), and nucleoprotein inhibitors (HBV core or capsid protein inhibitors).

In one embodiment, an HBV therapeutic includes adefovir (Hepsera®), tenofovir disoproxil fumarate+emtricitabine (Truvada®), tenofovir disoproxil fumarate (Viread®), entecavir (Baraclude®), lamivudine (Epivir-HBV®), tenofovir alafenamide, tenofovir, tenofovir disoproxil, tenofovir alafenamide fumarate, tenofovir alafenamide hemifumarate, telbivudine (Tyzeka®), Clevudine®, emtricitabine (Emtriva®), peginterferon alfa-2b (PEG-Intron®), Multiferon®, interferon alpha 1b (Hapgen®), interferon alpha-2b (Intron A®), pegylated interferon alpha-2a (Pegasys®), interferon alfa-n1 (Humoferon®), ribavirin, interferon beta-1a (Avonex®), Bioferon, Ingaron, Inmutag (IFN), Algeron, Roferon-A, Oligotide, Zutectra, Shaferon, interferon alfa-2b (AXXO), Alfaferone, interferon alfa-2b (BioGeneric Pharma), Feron, interferon-alpha 2 (CJ), BEVAC, Laferonum, VIPEG, BLAUFERON-B, BLAUFERON-A, Intermax Alpha, Realdiron, Lanstion, Pegaferon, PDferon-B, interferon alfa-2b (IFN, Laboratorios Bioprofarma), alfainterferona 2b, Kalferon, Pegnano, Feronsure, PegiHep, interferon alfa 2b (Zydus-Cadila), Optipeg A, Realfa 2B, Reliferon, interferon alfa-2b (Amega), interferon alfa-2b (Virchow), peginterferon alfa-2b (Amega), Reaferon-EC, Proquiferon, Uniferon, Urifron, interferon alfa-2b (Changchun Institute of Biological Products), Anterferon, Shanferon, MOR-22, interleukin-2 (IL-2, Immunex), recombinant human interleukin-2 (Shenzhen Neptunus), Layfferon, Ka Shu Ning, Shang Sheng Lei Tai, INTEFEN, SINOGEN, Fukangtai, Alloferon and celmoleukin.

In some embodiments, combinations of one or more HBV therapeutics (“cocktails”) can be used. Such combinations can be administered simultaneously or sequentially as part of treatment and can optionally be staggered over time with various combinations of HBV therapeutics. In some embodiments, a treating physician will develop or design an individualized treatment regimen (meaning a treatment regimen that is specific for that subject or patient) for a subject using one or more HBV therapeutics based on clinical parameters, cutoffs, publications or combinations thereof. In some embodiments, a treating physician will use an algorithm(s) designed to assess data relating to HBV treatment, as disclosed herein, as part of the development of an individualized treatment regimen for a subject. In some embodiments, the treatment being administered is part of a clinical trial. The treatment that is being administered as part of a clinical trial comprises a treatment regimen that has been designed or developed for one or more subjects or patients by a clinician or physician based on clinical parameters (such as, for example, those obtained from a prior clinical trial), cutoffs (such as, for example, those obtained from a prior clinical trial), patient profiles, publications or any combinations thereof.

Embodiments of the present disclosure also include methods of treatment that combine the diagnostic methods described herein with literature-based treatments, protocols, analytics and combinations thereof to establish personalized treatment plans (such as individualized treatment regimens) for a subject in need of HBV therapy. In some embodiments, the methods of treatment of the present disclosure enable a prescribing physician to develop a personalized/individualized dosing regimen using one or more published mathematical models reflecting actual clinical data, without the loss of resolution in the data and/or model that results from distillation of the actual clinical data into a relatively coarsely stratified set of recommendations for an “average” or “typical” patient. Generally, the method involves assembling mathematical models developed from clinical data gathered from patients to whom a particular medication had been administered (e.g., an HBV therapeutic), processing the models to create a composite model rich in patient data, and determining patient-specific dosing regimens as a function of patient-specific observed response data processed in conjunction with data from the mathematical model(s). In some embodiments, the methods involve Bayesian averaging, Bayesian updating and Bayesian forecasting techniques to develop patient-specific dosing regimens as a function of not only generic mathematical models and patient-specific characteristics accounted for in the models as covariate patient factors, but also observed patient-specific responses that are not accounted for within the models themselves, and that reflect “between-subject variability” that distinguishes the specific patient from the typical patient reflected by the model. Examples of such models are described in U.S. Patent Publication No. 2014/0351197, the contents of which are herein incorporated by reference.

Typical models also describe the expected impact of specific patient characteristics, such as the results of a diagnostic test, on response, as well as quantify the amount of unexplained variability that cannot be accounted for solely by patient characteristics. In such models, patient characteristics are reflected as patient factor covariates within the mathematical model. Thus, the mathematical model is typically a mathematical function that describes underlying clinical data and the associated variability seen in the patient population. These mathematical functions include terms that describe the variation of an individual patient from the “average” or typical patient, allowing the model to describe or predict a variety of outcomes for a given dose and making the model not only a mathematical function, but also a statistical function, though the models and functions are referred to herein in a generic and non-limiting fashion as “mathematical” models and functions. It will be appreciated that many suitable mathematical models already exist and are used for purposes such as drug product development. Examples of suitable mathematical models describing response profiles for a population of patients and accounting for patient factor covariates include pharmacokinetic (PK) models, pharmacodynamic (PD) models, and exposure/response models, which are well known to those of skill in the art. Such mathematical models are typically published or otherwise obtainable from medication manufacturers, the peer-reviewed literature, and the FDA or other regulatory agencies. Alternatively, suitable mathematical models may be prepared by original research.

Embodiments of the present disclosure also contemplate continuing treatment in subjects currently receiving treatment with one or more HBV therapeutics in order to prevent or reduce the risk of DNA reactivation and/or relapse. In other embodiments, the assays of the present disclosure can be used to predict or determine whether a subject for whom treatment has been stopped (e.g., due to seroclearance), may have or has a potential relapse.

All patents and publications mentioned in the specification are indicative of the levels of those skilled in the art to which the disclosure pertains. All patents and publications are herein incorporated by reference to the same extent as if each individual publication was specifically and individually indicated to be incorporated by reference.

The disclosure illustratively described herein suitably may be practiced in the absence of any element or elements, limitation or limitations which is not specifically disclosed herein. Thus, for example, in each instance herein any of the terms “comprising,” “consisting essentially of” and “consisting of” may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the disclosure claimed. Thus, it should be understood that although the present disclosure includes various embodiments and optional features, modification and variation of the concepts herein disclosed may be resorted to by those skilled in the art, and that such modifications and variations are considered to be within the scope of this disclosure as defined by the appended claims.

EXAMPLES

Example 1

Described herein is the development and use of two fully automated assays to specifically analyze phosphorylated HBcAg levels (P-HBcAg, representing non-infectious or “empty” particles) and non-phosphorylated HBcAg levels (representing HBV DNA-containing particles (“infectious” particles) in single timepoint patients with active infections, in a longitudinal seroconversion panel, and in a patient receiving HBV treatment.

The assays developed are chemiluminescent microparticle immunoassays (CMIA) on a fully automated platform which use specific monoclonal antibodies to capture and detect either phosphorylated or non-phosphorylated HBcAg circulating in HBV infected patients.

Methods:

P-HBcAg/HBcAg detection: Patient specimens were fully automated analyzed on the ARCHITECT i2000SR instrument. HBcAg was captured and detected by monoclonal antibodies directed to phosphorylated or non-phosphorylated HBcAg. Detection was achieved by antibodies labeled with a luminescent molecule.

Other HBV markers: HBV DNA viral loads were determined using the Abbott HBV Realtime assay with 0.2 ml input volume as per package insert instructions. Serologic testing was performed on the Abbott ARCHITECT for HBeAg. HBcrAg levels were analyzed on a LUMIPULSE G1200 instrument.

Results:

Table 1 shows the HBcAg assay limit of detection (LOD) and limit of quantitation (LOQ), which were determined in triplicate using recombinant P-HBcAg/HBcAg.

| Antigen | LOD (pg/ml) | LOQ (pg/ml) |
|---|---|---|
| HBcAg | 6 | 14 |
| P-HBcAg | 0.8 | 4 |

HBeAg cross-reactivity was evaluated with recombinant HBeAg for concentrations up to 10 μg/ml in triplicate. No cross-reactivity was observed for both P-HBcAg/HBcAg assay formats. P-HBcAg/HBcAg assay linearity was evaluated in triplicate using recombinant antigens. Linear detection was demonstrated over 5-$10^4$ pg/ml ($R^2$=0.999) for P-HBcAg and $10^1$-$10^5$ pg/ml ($R^2$=0.991) for HBcAg.

Figure 4A:
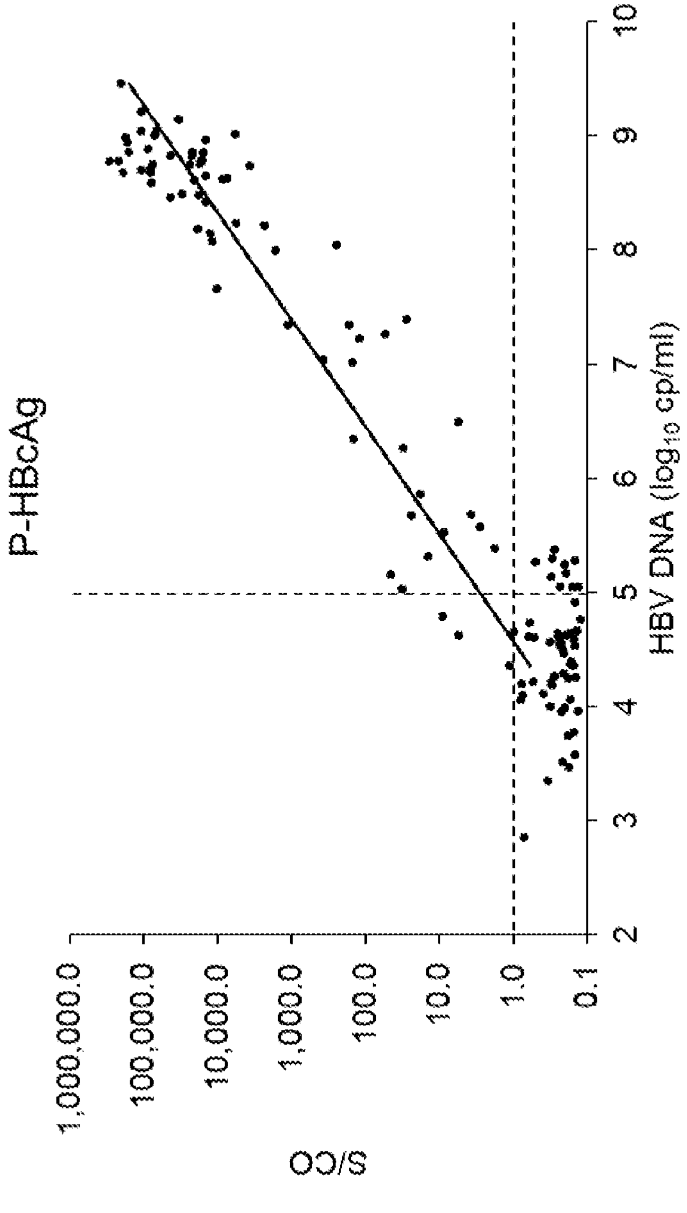
FIG. 4A shows an analysis of P-HBcAg levels in clinical samples that tested positive for HBsAg and containing a viral load from $10^3$ to $10^9$ HBV DNA copies/ml.
Figure 4B:
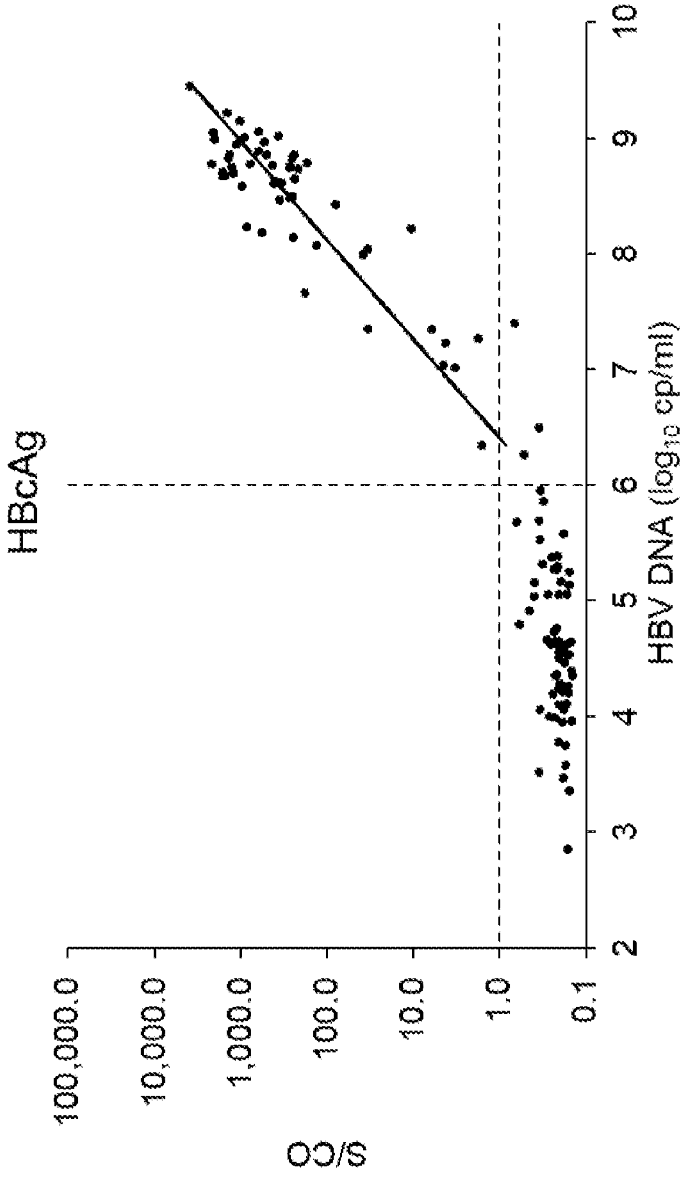
FIG. 4B shows an analysis of HBcAg levels in clinical samples that tested positive for HBsAg and containing a viral load from $10^3$ to $10^9$ HBV DNA copies/ml. P-HBcAg could be detected in 84% of the samples containing a viral load of $\geq 10^5$ cp/ml. HBcAg was detected in 94% of the samples with a viral load of $\geq 10^6$ cp/ml.
Figure 5B:
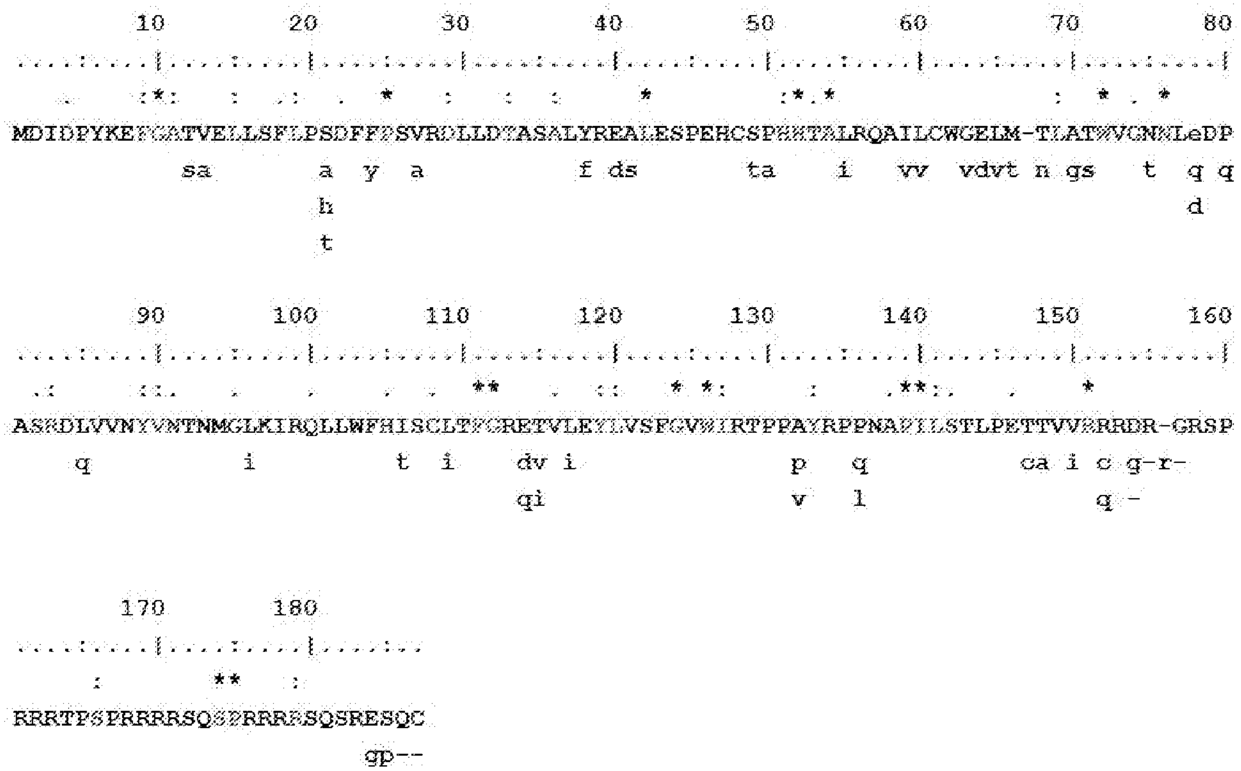
FIG. 5B shows a consensus sequence for HBcAg Genotype A.
Figure 5E:
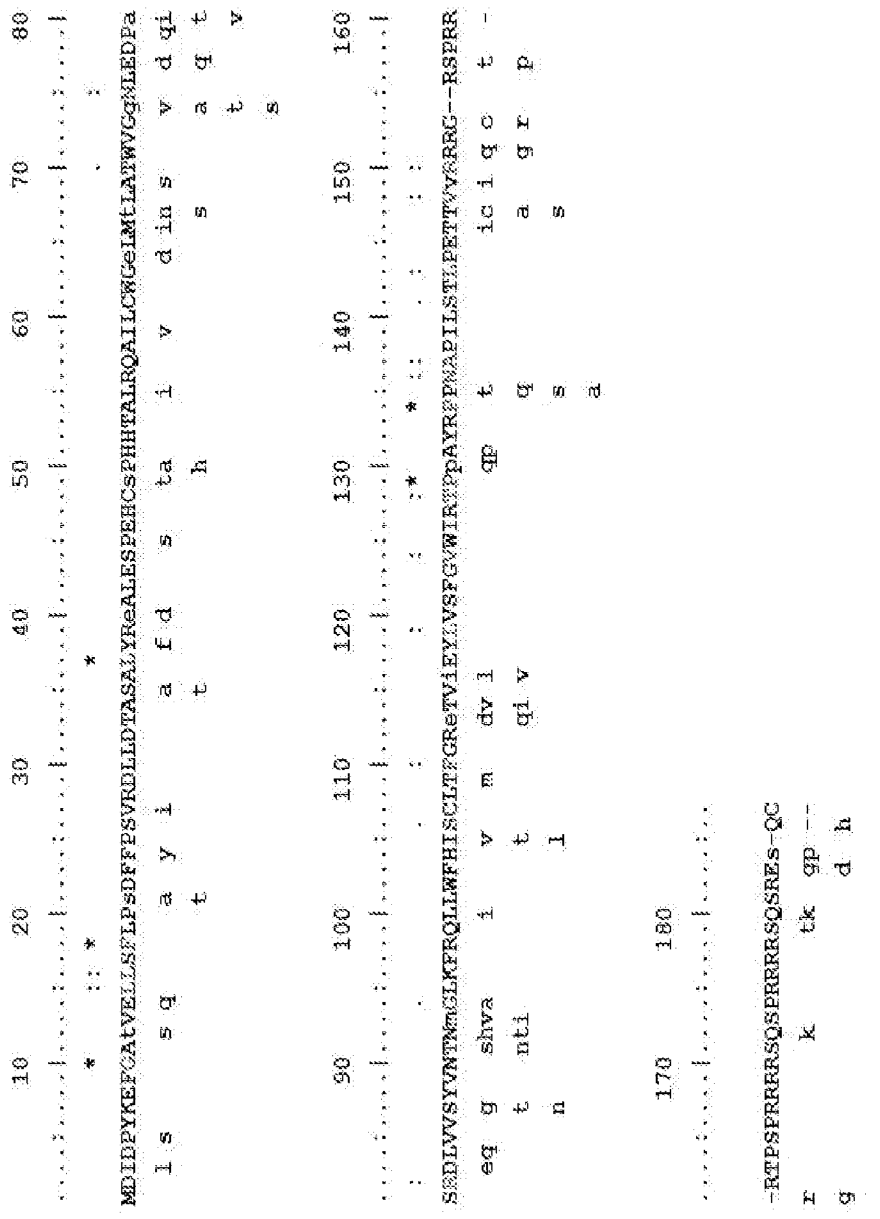
FIG. 5E shows a consensus sequence for HBcAg Genotype D.
Figure 5F:
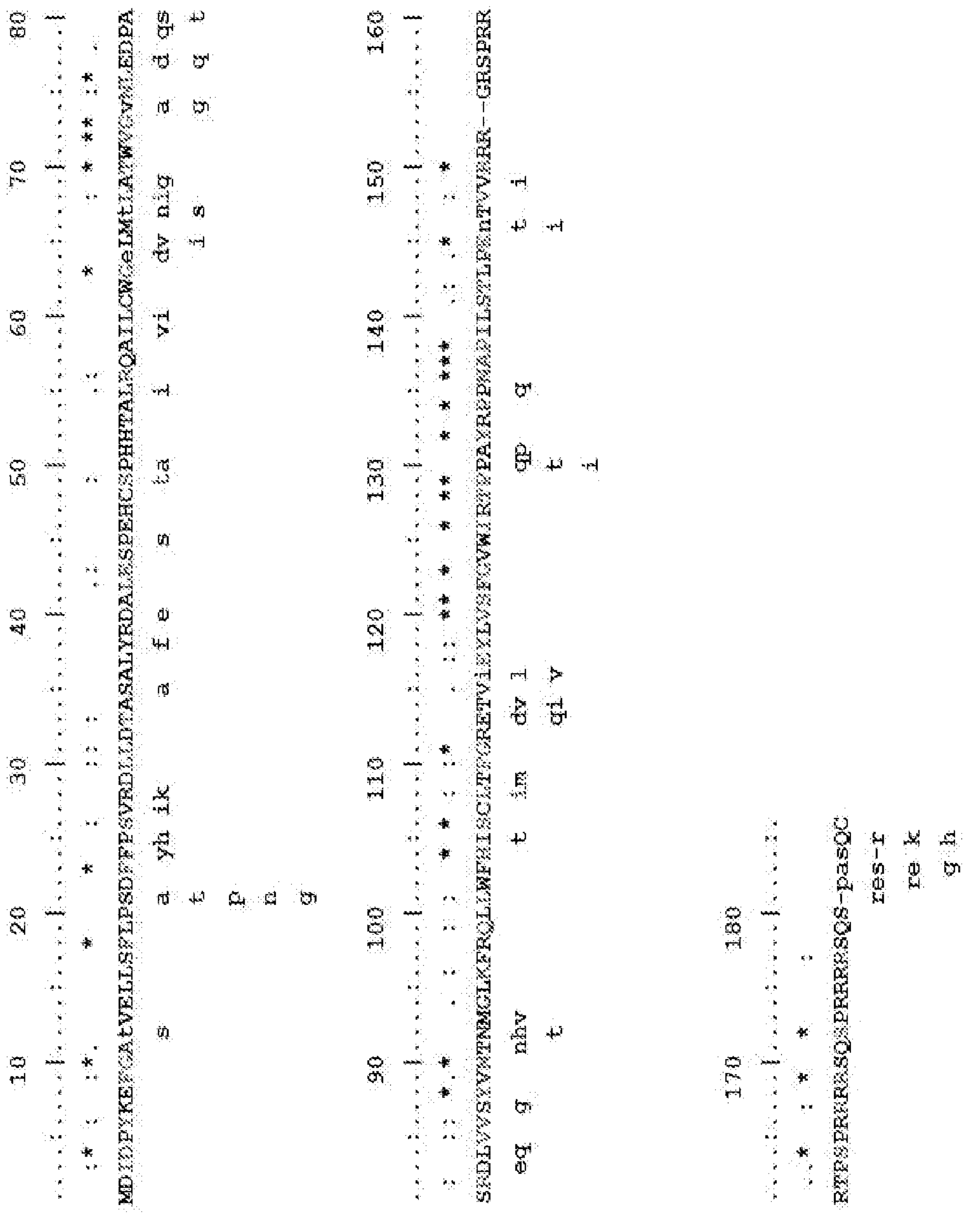
FIG. 5F shows a consensus sequence for HBcAg Genotype E.
Figure 5G:
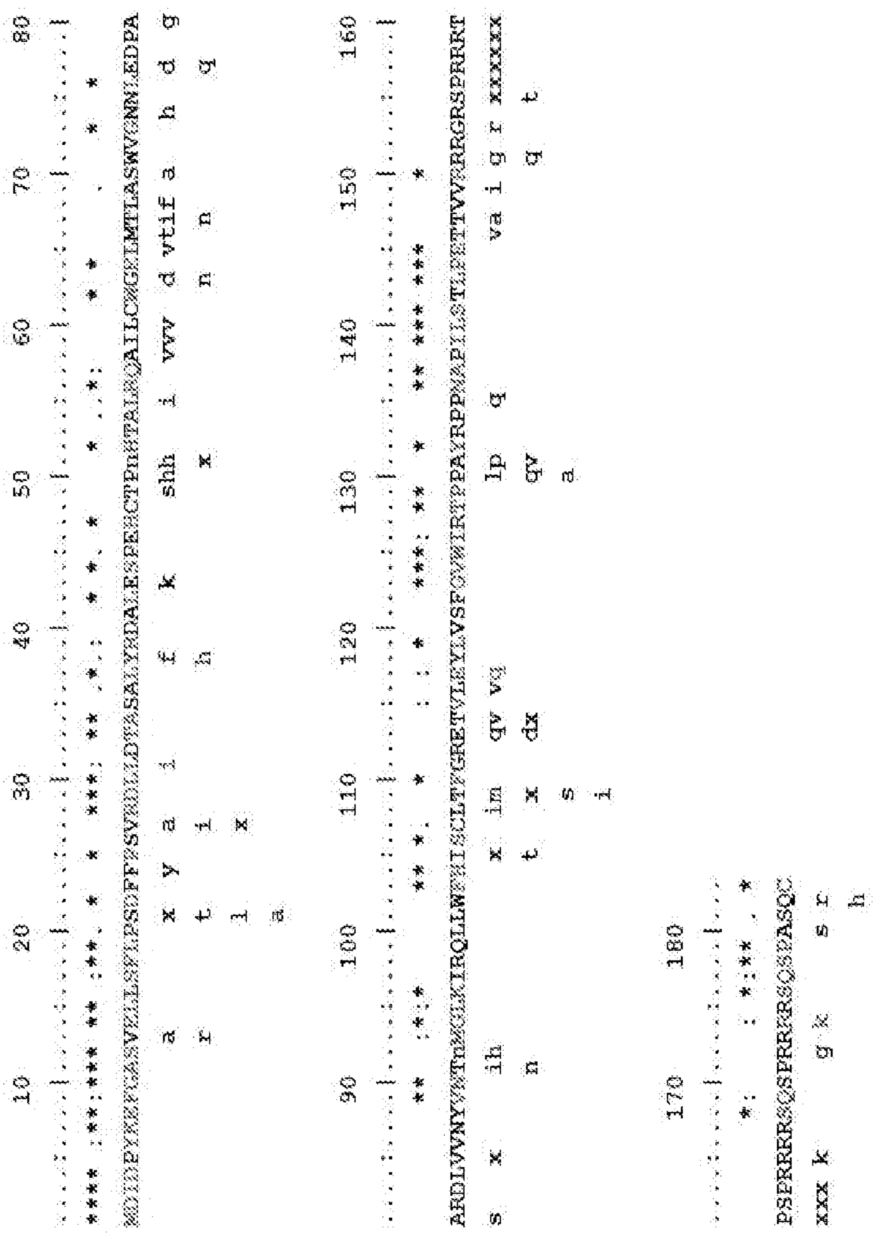
FIG. 5G shows a consensus sequence for HBcAg Genotype F.
Figure 5H:
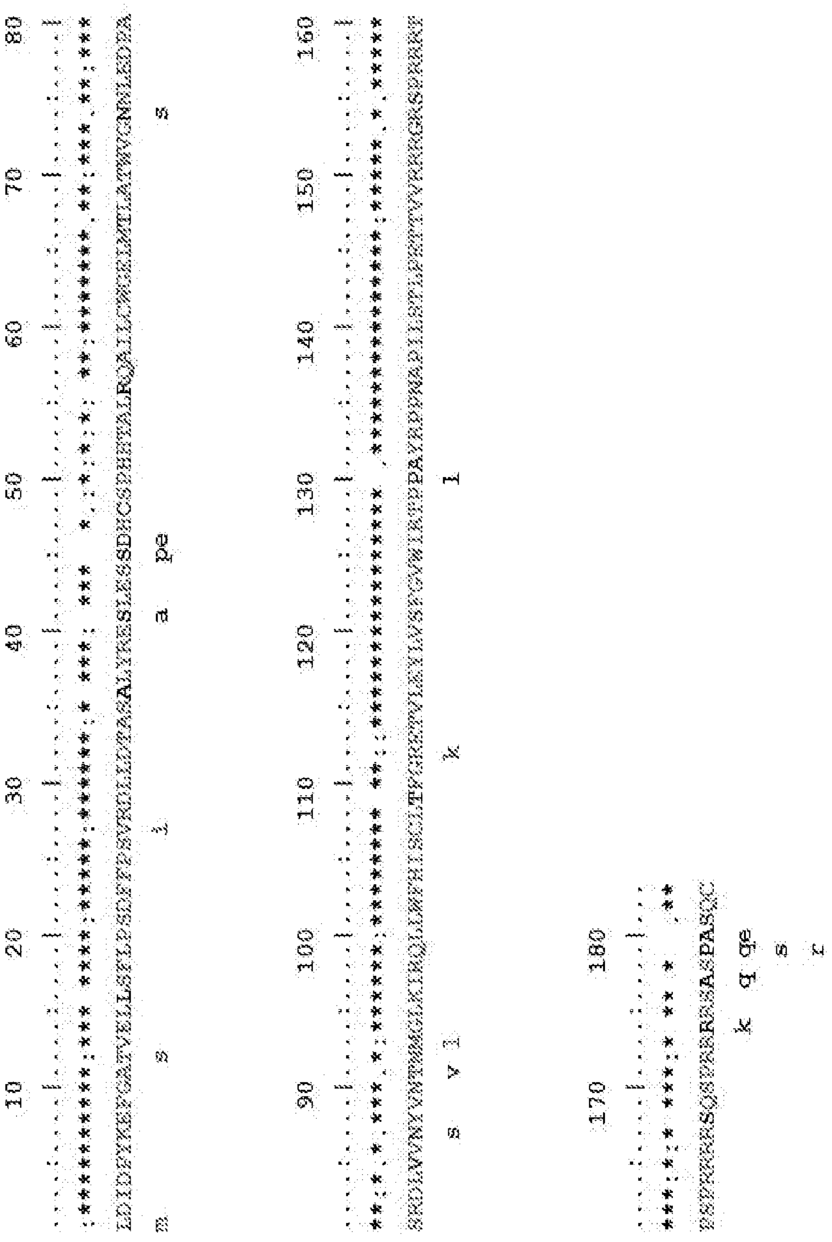
FIG. 5H shows a consensus sequence for HBcAg Genotype G.
Figure 5I:
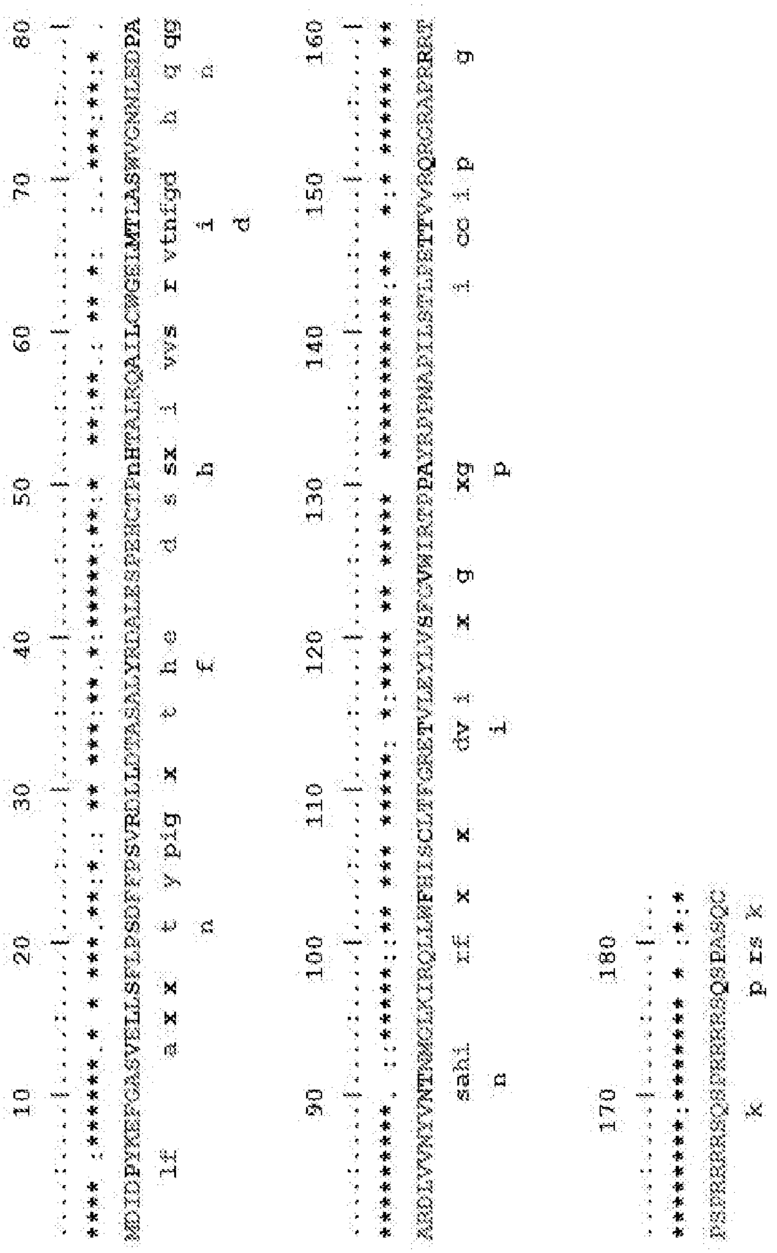
FIG. 5I shows a consensus sequence for HBcAg Genotype H. In each of FIG. 5A-5I, an * (asterisk) indicates positions which have a single, fully conserved residue. A:(colon) indicates conservation between groups of strongly similar properties as below—roughly equivalent to scoring >0.5 in the Gonnet PAM 250 matrix.

FIG. 4 shows an analysis of P-HBcAg/HBcAg levels in clinical samples that tested positive for HBsAg and containing a viral load from ~$10^3$ to $10^9$ HBV DNA copies/ml. P-HBcAg could be detected in 84% of the samples containing a viral load of ≥$10^5$ cp/ml. HBcAg was detected in 94% of the samples with a viral load of ≥$10^6$ cp/ml.

FIG. 1 shows an HBV seroconversion panel comparing levels of phosphorylated HBV core antigen (P-HBcAg), HBV core antigen (HBcAg), HBeAg and HBcrAg with levels of HBV DNA over time. As shown in FIG. 1, P-HBcAg and HBcAg levels correlate well with HBV DNA levels and can detect acute HBV infection, whereas HBcrAg levels appeared to track more closely to HBeAg levels rather than HBcAg/P-HBcAg levels after HBV DNA reaches peak levels.

Figure 2:
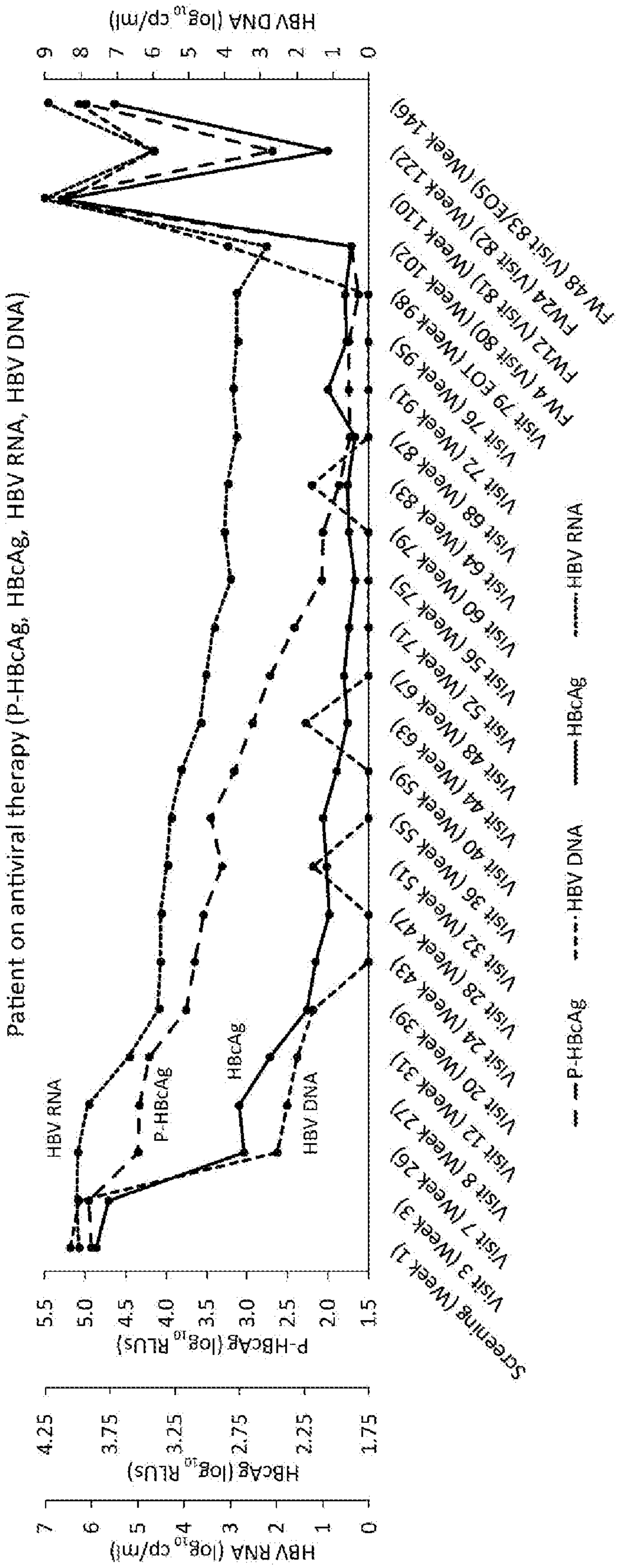
FIG. 2 shows a comparison of levels of P-HBcAg and HBcAg to HBV DNA and HBV RNA levels following treatment for HBV infection. Levels of HBcAg (black line) corresponds with HBV DNA levels over the course of treatment. Phosphorylated P-HBcAg (blue line) correlates more closely with HBV RNA levels compared to HBV DNA levels over the course of treatment. Some data presented in the figure is obtained from Bazinet et al., Hepatology Communications 5; 11 (2021) 1873-1887.

HBV positive subject received antiviral treatment with nucleos(t)ide analogues, interferon, or HBsAg inhibitors. Levels of P-HBcAg, HBV DNA, HBcAg, and HBV RNA were measured in samples obtained from the subject at 1-4 week intervals during therapy, starting on the first day of treatment and ending 146 weeks after treatment. As shown in FIG. 2, levels of HBcAg (black line) corresponds with HBV DNA levels over the course of treatment. Accordingly, this data demonstrates that non-phosphorylated HBcAg (present in infectious HBV particles, black line) is able to show the efficacy of nucleotide analogs right at the beginning of the treatment (i.e. decrease of HBcAg levels). Moreover, phosphorylated P-HBcAg (present in non-infectious particles, blue line) can measure the transcriptional activity of cccDNA (i.e. non-infectious, empty, particles are still secreted despite non-detectable HBV DNA in the blood).

For reasons of completeness, various aspects of the disclosure are set out in the following numbered clauses:

Clause 1: A method of assessing and monitoring stage or phase of chronic Hepatitis B (HBV) infection or monitoring response to a treatment for chronic HBV in a subject, the method comprising the steps of:

a) performing an assay to detect the presence or level of Hepatitis B core antigen (HBcAg) and phosphorylated Hepatitis B core antigen (P-HBcAg) in at least one sample obtained from a subject diagnosed with chronic HBV or receiving a treatment for chronic HBV, wherein the assay comprises contacting the at least one sample with an antibody that specifically binds to HBcAg and an antibody that specifically binds to P-HBcAg; and b) assessing and monitoring stage or phase of chronic HBV infection or monitoring response to the treatment for chronic HBV based on the presence or level of HBcAg and P-HBcAg in the at least one sample.

Clause 2: The method of clause 1, wherein the subject is being assessed and monitored for the stage or phase of chronic HBV, and wherein the method further comprises providing a treatment for chronic HBV to the subject based upon the presence or level of HBcAg and P-HBcAg in the at least one sample.

Clause 3: The method of clause 1, wherein the subject is receiving a treatment for chronic HBV, and wherein the method further comprises altering the treatment for HBV based on the presence or level of HBcAg and P-HBcAg in the at least one sample.

Clause 4: A method of assessing and monitoring stage or phase of chronic Hepatitis B (HBV) infection, the method comprising the steps of:

a) performing an assay to detect the presence or level of Hepatitis B core antigen (HBcAg) in at least one sample obtained from a subject diagnosed with chronic HBV, wherein the assay comprises contacting the at least one sample with an antibody that specifically binds to HBcAg; and b) determining the amount of infectious HBV particles in the at least one sample based upon the presence or level of HBcAg in the at least one sample, wherein the amount of infectious HBV particles is determined regardless of whether the subject has or has not received a treatment for HBV prior to performing the assay of step a).

Clause 5: The method of clause 4, further comprising providing a treatment for chronic HBV to the subject when the amount of infectious HBV particles in the at least one sample is equal to or above a threshold value.

Clause 6: A method of assessing and monitoring stage or phase of chronic Hepatitis B (HBV) infection, the method comprising the steps of:

a) performing an assay to detect the presence or level of Hepatitis B core antigen (HBcAg) in at least one sample obtained from a subject diagnosed with chronic HBV, wherein the assay comprises contacting the at least one sample with an antibody that specifically binds to HBcAg;

b) determining the amount of infectious HBV particles in the at least one sample based upon the presence or level of HBcAg in the at least one sample, wherein the amount of infectious HBV particles is determined regardless of whether the subject has or has not received a treatment for HBV prior to performing the assay of step a); and c) providing a treatment for chronic HBV to the subject when the amount of infectious HBV particles in the at least one sample is equal to or above a threshold value.

Clause 7: A method of monitoring response to a treatment for chronic Hepatitis B (HBV) infection in a subject, the method comprising the steps of:

a) performing an assay to detect the presence or level of Hepatitis B core antigen (HBcAg) in at least one sample obtained from a subject receiving a treatment for chronic HBV, wherein the assay comprises contacting the at least one sample with an antibody that specifically binds to HBcAg;

b) determining the amount of infectious HBV particles in the at least one sample based upon the presence or level of HBcAg in the at least one sample; and c) determining that the treatment is efficacious when the amount of infectious HBV particles in the at least one sample is less than a reference level; or d) determining that the treatment is not efficacious when the amount of infectious HBV particles in the at least one sample is greater than or equal to a reference level.

Clause 8: A method of monitoring response to a treatment for chronic Hepatitis B (HBV) infection in a subject, the method comprising the steps of:

a) performing an assay to detect the presence or level of Hepatitis B core antigen (HBcAg) and phosphorylated Hepatitis B core antigen (P-HBcAg) in at least one sample obtained from a subject receiving a treatment for chronic HBV, wherein the assay comprises contacting the at least one sample with an antibody that specifically binds to HBcAg and an antibody that specifically binds to P-HBcAg;

b) determining the amount of infectious HBV particles in the at least one sample based upon the presence or level of HBcAg in the at least one sample;

c) determining the amount of non-infectious HBV particles in the at least one sample based upon the presence or level of P-HBcAg in the at least one sample; and d) determining response to the treatment for chronic HBV based upon the amount of infectious and/or non-infectious HBV particles in the at least one sample.

Clause 9: The method of clause 8, wherein:

a) the treatment is determined to be efficacious when the amount of infectious HBV particles in the at least one sample is less than a reference level;

b) the treatment is determined to be efficacious when the amount of infectious HBV particles in the at least one sample is less than a reference level and the amount of non-infectious HBV particles in the at least one sample is less than a reference level; or c) the treatment is determined to not be efficacious when the amount of infectious HBV particles in the at least one sample is greater than or equal to a reference level.

Clause 10: A method of monitoring response to a treatment for chronic Hepatitis B (HBV) infection in a subject, the method comprising the steps of:

a) performing an assay to detect the presence or level of Hepatitis B core antigen (HBcAg) and phosphorylated Hepatitis B core antigen (P-HBcAg) in at least two samples obtained from a subject receiving a treatment for chronic HBV, wherein the at least two samples comprise a first sample obtained from the subject at a first time point before or after receiving the treatment for chronic HBV and a second sample obtained from the subject at a second time point after the first time point, and wherein the assay comprises contacting the at least two samples with an antibody that specifically binds to HBcAg and an antibody that specifically binds to P-HBcAg;

b) determining the amount of infectious HBV particles in the at least two samples based upon the presence or level of HBcAg and/or determining the amount of non-infectious HBV particles in the at least two samples based upon the presence or level of P-HBcAg; and determining response to the treatment for chronic HBV based upon the amount of infectious and/or non-infectious HBV particles in the at least two samples.

Clause 11: The method of clause 10, wherein:

a) the treatment is determined to be efficacious when the amount of infectious HBV particles in the second sample reduced by at least an absolute amount compared to the amount of infectious HBV particles in the first sample;

b) the treatment is determined to be efficacious when the amount of infectious HBV particles in the second sample reduced by at least an absolute amount compared to the amount of infectious HBV particles in the first sample and wherein the amount of non-infectious HBV particles in the second sample is reduced by at least an absolute amount compared to the amount of non-infectious HBV particles in the first sample; or c) the treatment is determined to not be efficacious when the amount of infectious HBV particles in the second sample is not reduced by at least an absolute amount compared to the amount of infectious HBV particles in the first sample.

Clause 12: The method of clause 11, wherein the first sample is obtained from the subject within 24 hours of receiving the treatment for chronic HBV.

Clause 13: The method of clause 11 or clause 12, wherein the second sample is obtained from the subject 10-14 weeks after the first sample.

Clause 14: the method of clause 13, wherein the first sample is obtained from the subject within 24 hours of receiving the treatment for chronic HBV and the second sample is obtained from the subject 10-14 weeks after the first sample.

Clause 15: The method of clause 7, clause 9, or clause 11, further comprising altering the treatment for chronic HBV when the treatment is determined to not be efficacious.

Clause 16: The method of clause 15, wherein altering the treatment for chronic HBV comprises providing to the subject an increased dose of the treatment, increasing the frequency of dosing with the treatment, providing to the subject a second treatment, or any combination thereof.

Clause 17: The method of any one of the preceding clauses, wherein: (a) the antibody that specifically binds to HBcAg binds to an epitope comprising at least 3 amino acids of SEQ ID NO: 2 and/or wherein the antibody that specifically binds to P-HBcAg binds to an epitope comprising at least 3 amino acids of SEQ ID NO: 2 or SEQ ID NO:25, provided that at least one amino acid of SEQ ID NO: 2 or SEQ ID NO:25 is phosphorylated; and/or (b) the antibody that specifically binds to HBcAg binds to an epitope within amino acids 1-149 of SEQ ID NO: 1 and/or the antibody that specifically binds to P-HBcAg binds to an epitope within amino acids 1-149 of SEQ ID NO: 1, provided that at least one of amino acids 1-149 is phosphorylated.

Clause 18: The method of any one of the preceding clauses, wherein the treatment for chronic HBV is an interferon, nucleos(t)ide analogue, a nucleic acid, an immunomodulator, a core protein assembly inhibitor, a capsid assembly modulator (CAM), an HBsAg release inhibitor, an entry inhibitor, interfering RNA, a DNA modifying agent, or a combination thereof.

Clause 19: The method of clause 18, wherein:

a) the interferon is interferon alpha-2a or PEGylated interferon alpha-2a;

b) the nucleos(t)ide analogue is lamivudine, adefovir, tenofovir, telbivudine, or entecavir;

c) the nucleic acid is an siRNA, an antisense oligonucleotide, an shRNA, or a miRNA;

d) the core protein assembly inhibitor is NVR 3-1983, GLS4 or BAY 41-4109;

e) the CAM is JNJ-632, AT130, or BAY41-4109;

f) the HBsAg release inhibitor is REP 9 AC;

g) the entry inhibitor is Myrcludex-B; or h) any combination of a)-g).

Clause 20: The method of any one of the preceding clauses, wherein performing the assay to measure the level of HBcAg in the at least one sample comprises contacting the at least one sample, either simultaneously or sequentially, in any order with:

a) a Hepatitis B core antigen (HBcAg) capture antibody which binds to an epitope on the C-terminus of HBcAg to form a capture antibody-HBcAg complex; and b) a detection antibody binds to an epitope on HBcAg that is not bound by the HBcAg capture antibody, such that a capture antibody-HBcAg-detection antibody complex is formed; and c) measuring the level of HBcAg in the sample based on a signal generated by a detectable label in the capture antibody-HBcAg-detection antibody complex.

Clause 21: The method of any one of the preceding clauses, wherein performing the assay to measure the level of P-HBcAg in the sample comprises contacting the sample, either simultaneously or sequentially, in any order with:

a) a phosphorylated Hepatitis B core antigen (P-HBcAg) capture antibody which binds to an epitope on the C-terminus of P-HBcAg to form a capture antibody-P-HBcAg complex; and b) a detection antibody binds to an epitope on P-HBcAg that is not bound by the P-HBcAg capture antibody, such that a capture antibody-P-HBcAg-detection antibody complex is formed; and c) measuring the level of P-HBcAg in the sample based on a signal generated by a detectable label in the capture antibody-P-HBcAg-detection antibody complex.

Clause 22: Use of reagents for detection of the presence or level of Hepatitis B core antigen (HBcAg) and phosphorylated Hepatitis B core antigen (P-HBcAg) in a method of assessing a stage or phase of Hepatitis B (HBV) infection or monitoring a response to a treatment for chronic HBV in a subject.

Clause 23: A kit or system comprising reagents for detection of the presence, level, or status of Hepatitis B core antigen (HBcAg) and phosphorylated Hepatitis B core antigen (P-HBcAg).

```
                          SEQUENCE LISTING

Sequence total quantity: 40
SEQ ID NO: 1              moltype = AA  length = 185
FEATURE                   Location/Qualifiers
REGION                    1..185
                          note = Synthetic
source                    1..185
                          mol_type = protein
                          organism = synthetic construct
SEQUENCE: 1
MDIDPYKEFG ATVELLSFLP SDFFPSVRDL LDTASALYRE ALESPEHCSP HHTALRQAIL  60
CWGELMTLAT WVGNNLEDPA SRDLVVNYVN TNMGLKIRQL LWFHISCLTF GRETVLEYLV  120
SFGVWIRTPP AYRPPNAPIL STLPETTVVR RRDRGRSPRR RTPSPRRRRS QSPRRRRSQS  180
RESQC                                                              185

SEQ ID NO: 2              moltype = AA  length = 36
FEATURE                   Location/Qualifiers
REGION                    1..36
                          note = Synthetic
source                    1..36
                          mol_type = protein
                          organism = synthetic construct
SEQUENCE: 2
RRRDRGRSPR RRTPSPRRRR SQSPRRRRSQ SRESQC                            36

SEQ ID NO: 3              moltype = AA  length = 149
FEATURE                   Location/Qualifiers
REGION                    1..149
                          note = Synthetic
source                    1..149
                          mol_type = protein
                          organism = synthetic construct
SEQUENCE: 3
MDIDPYKEFG ATVELLSFLP SDFFPSVRDL LDTASALYRE ALESPEHCSP HHTALRQAIL  60
CWGELMTLAT WVGNNLEDPA SRDLVVNYVN TNMGLKIRQL LWFHISCLTF GRETVLEYLV  120
SFGVWIRTPP AYRPPNAPIL STLPETTVV                                    149

SEQ ID NO: 4              moltype = AA  length = 183
FEATURE                   Location/Qualifiers
REGION                    1..183
                          note = Synthetic
source                    1..183
                          mol_type = protein
                          organism = synthetic construct
SEQUENCE: 4
MDIDPYKEFG ASVELLSFLP SDFFPSIRDL LDTASALYRE ALESPEHCSP HHTALRQAIL  60
CWGELMNLAT WVGSNLEDPA SRELVVSYVN VNMGLKIRQL LWFHISCLTF GRETVLEYLV  120
SFGVWIRTPP AYRPPNAPIL STLPETTVVR RRGRSPRRRT PSPRRRRSQS PRRRRSQSRE  180
SQC                                                                183

SEQ ID NO: 5              moltype = AA  length = 183
FEATURE                   Location/Qualifiers
REGION                    1..183
                          note = Synthetic
source                    1..183
                          mol_type = protein
```

```
                        organism = synthetic construct
SEQUENCE: 5
MDIDPYKEFG ASVELLSFLP SDFFPSIRDL LDTASALYRE ALESPEHCSP HHTALRQAIL  60
CWGELMNLAT WVGSNLEDPA SRELVVSYVN VNMGLKIRQL LWFHISCLTF GRETVLEYLV  120
SFGVWIRTPP AYRPPNAPIL STLPETTVVR RRGRSPRRRT PSPRRRRSQS PRRRRSQSRE  180
SQC                                                               183

SEQ ID NO: 6            moltype = AA  length = 183
FEATURE                 Location/Qualifiers
REGION                  1..183
                        note = Synthetic
source                  1..183
                        mol_type = protein
                        organism = synthetic construct
SEQUENCE: 6
MDIDPYKEFG ATVELLSFLP SDFFPSVRDL LDTASALYRE ALESPEHCSP HHTALRQAIL  60
CWGELMTLAT WVGGNLEDPA SRDLVVSYVN TNMGLKFRQL LWFHISCLTF GRETVIEYLV  120
SFGVWIRTPP AYRPPNAPIL STLPETTVVR RRGRSPRRRT PSPRRRRSQS PRRRRSQSRE  180
SQC                                                               183

SEQ ID NO: 7            moltype = AA  length = 183
FEATURE                 Location/Qualifiers
REGION                  1..183
                        note = Synthetic
source                  1..183
                        mol_type = protein
                        organism = synthetic construct
SEQUENCE: 7
MDIDPYKEFG ATVELLSFLP SDFFPSVRDL LDTASALYRD ALESPEHCSP HHTALRQAIL  60
CWGELMTLAT WVGVNLEDPA SRDLVVSYVN TNMGLKFRQL LWFHISCLTF GRETVIEYLV  120
SFGVWIRTPP AYRPPNAPIL STLPENTVVR RRGRSPRRRT PSPRRRRSQS PRRRRSQSPA  180
SQC                                                               183

SEQ ID NO: 8            moltype = AA  length = 183
FEATURE                 Location/Qualifiers
REGION                  1..183
                        note = Synthetic
source                  1..183
                        mol_type = protein
                        organism = synthetic construct
SEQUENCE: 8
MDIDPYKEFG ASVELLSFLP SDFFPSVRDL LDTASALYRD ALESPEHCTP NHTALRQAIL  60
CWGELMTLAS WVGNNLEDPA ARDLVVNYVN TNMGLKIRQL LWFHISCLTF GRETVLEYLV  120
SFGVWIRTPP AYRPPNAPIL STLPETTVVR RRGRSPRRRT PSPRRRRSQS PRRRRSQSPA  180
SQC                                                               183

SEQ ID NO: 9            moltype = AA  length = 195
FEATURE                 Location/Qualifiers
REGION                  1..195
                        note = Synthetic
source                  1..195
                        mol_type = protein
                        organism = synthetic construct
SEQUENCE: 9
MDRTTLPYGL FGLDIDPYKE FGATVELLSF LPSDFFPSVR DLLDTASALY RESLESSDHC  60
SPHHTALRQA ILCWGELMTL ATWVGNNLED PASRDLVVNY VNTNMGLKIR QLLWFHISCL  120
TFGRETVLEY LVSFGVWIRT PPAYRPPNAP ILSTLPETTV VRRRGRSPRR RTPSPRRRRS  180
QSPRRRRSAS PASQC                                                  195

SEQ ID NO: 10           moltype = AA  length = 183
FEATURE                 Location/Qualifiers
REGION                  1..183
                        note = Synthetic
source                  1..183
                        mol_type = protein
                        organism = synthetic construct
SEQUENCE: 10
MDIDPYKEFG ASVELLSFLP SDFFPSVRDL LDTASALYRD ALESPEHCTP NHTALRQAIL  60
CWGELMTLAS WVGNNLEDPA ARDLVVNYVN TNMGLKIRQL LWFHISCLTF GRETVLEYLV  120
SFGVWIRTPP AYRPPNAPIL STLPETTVVR QRGRAPRRRT PSPRRRRSQS PRRRRSQSPA  180
SQC                                                               183

SEQ ID NO: 11           moltype = AA  length = 183
FEATURE                 Location/Qualifiers
REGION                  1..183
                        note = Synthetic
source                  1..183
                        mol_type = protein
                        organism = synthetic construct
```

```
SEQUENCE: 11
MDIDPYKEFG ASVELLSFLP SDFFPSIRDL LDTASALYRE ALESPEHCSP HHTALRQAIV  60
CWGELMNLAT WVGSNLEDPA SRELVVSYVN VNMGLKIRQL LWFHISCLTF GRETVLEYLV  120
SFGVWIRTPP AYRPPNAPIL STLPETTVVR RRGRSPRRRT PSPRRRRSQS PRRRRSQSRE  180
SQC                                                               183

SEQ ID NO: 12          moltype = AA  length = 183
FEATURE                Location/Qualifiers
REGION                 1..183
                       note = Synthetic
source                 1..183
                       mol_type = protein
                       organism = synthetic construct
SEQUENCE: 12
MDIDPYKEFG ASVELLSFLP SDFFPSIRDL LDTASALYRE ALESPEHCSP HHTALRQAVL  60
CWGELMNLAT WVGSNLEDPA SRELVVSYVN INMGLKIRQL LWFHISCLTF GRETVLEYLV  120
SFGVWIRTPP AYRPPNAPIL STLPETTVVR RRGRSPRRRT PSPRRRRSQS PRRRRSQSPS  180
SQC                                                               183

SEQ ID NO: 13          moltype = AA  length = 34
FEATURE                Location/Qualifiers
REGION                 1..34
                       note = Synthetic
source                 1..34
                       mol_type = protein
                       organism = synthetic construct
SEQUENCE: 13
RRRGRSPRRR TPSPRRRRSQ SPRRRRSQSR ESQC                             34

SEQ ID NO: 14          moltype = AA  length = 34
FEATURE                Location/Qualifiers
REGION                 1..34
                       note = Synthetic
source                 1..34
                       mol_type = protein
                       organism = synthetic construct
SEQUENCE: 14
RRRGRSPRRR TPSPRRRRSQ SPRRRRSQSR ESQC                             34

SEQ ID NO: 15          moltype = AA  length = 34
FEATURE                Location/Qualifiers
REGION                 1..34
                       note = Synthetic
source                 1..34
                       mol_type = protein
                       organism = synthetic construct
SEQUENCE: 15
RRRGRSPRRR TPSPRRRRSQ SPRRRRSQSR ESQC                             34

SEQ ID NO: 16          moltype = AA  length = 34
FEATURE                Location/Qualifiers
REGION                 1..34
                       note = Synthetic
source                 1..34
                       mol_type = protein
                       organism = synthetic construct
SEQUENCE: 16
RRRGRSPRRR TPSPRRRRSQ SPRRRRSQSP ASQC                             34

SEQ ID NO: 17          moltype = AA  length = 34
FEATURE                Location/Qualifiers
REGION                 1..34
                       note = Synthetic
source                 1..34
                       mol_type = protein
                       organism = synthetic construct
SEQUENCE: 17
RRRGRSPRRR TPSPRRRRSQ SPRRRRSQSP ASQC                             34

SEQ ID NO: 18          moltype = AA  length = 34
FEATURE                Location/Qualifiers
REGION                 1..34
                       note = Synthetic
source                 1..34
                       mol_type = protein
                       organism = synthetic construct
SEQUENCE: 18
RRRGRSPRRR TPSPRRRRSQ SPRRRRSASP ASQC                             34
```

```
SEQ ID NO: 19          moltype = AA  length = 34
FEATURE                Location/Qualifiers
REGION                 1..34
                       note = Synthetic
source                 1..34
                       mol_type = protein
                       organism = synthetic construct
SEQUENCE: 19
RQRGRAPRRR TPSPRRRRSQ SPRRRRSQSP ASQC                            34

SEQ ID NO: 20          moltype = AA  length = 34
FEATURE                Location/Qualifiers
REGION                 1..34
                       note = Synthetic
source                 1..34
                       mol_type = protein
                       organism = synthetic construct
SEQUENCE: 20
RRRGRSPRRR TPSPRRRRSQ SPRRRRSQSR ESQC                            34

SEQ ID NO: 21          moltype = AA  length = 34
FEATURE                Location/Qualifiers
REGION                 1..34
                       note = Synthetic
source                 1..34
                       mol_type = protein
                       organism = synthetic construct
SEQUENCE: 21
RRRGRSPRRR TPSPRRRRSQ SPRRRRSQSP SSQC                            34

SEQ ID NO: 22          moltype = AA  length = 152
FEATURE                Location/Qualifiers
REGION                 1..152
                       note = Synthetic
source                 1..152
                       mol_type = protein
                       organism = synthetic construct
SEQUENCE: 22
MDIDPYKEFG ASVELLSFLP SDFFPSIRDL LDTASALYRE ALESPEHCSP HHTALRQAIL  60
CWGELMNLAT WVGSNLEDPA SRELVVSYVN VNMGLKIRQL LWFHISCLTF GRETVLEYLV  120
SFGVWIRTPP AYRPPNAPIL STLPETTVVR RR                              152

SEQ ID NO: 23          moltype = AA  length = 34
FEATURE                Location/Qualifiers
REGION                 1..34
                       note = Synthetic
source                 1..34
                       mol_type = protein
                       organism = synthetic construct
SEQUENCE: 23
RRRGRSPRRR TPSPRRRRSQ SPRRRRSQSR ESQC                            34

SEQ ID NO: 24          moltype = AA  length = 187
FEATURE                Location/Qualifiers
REGION                 1..187
                       note = Synthetic
source                 1..187
                       mol_type = protein
                       organism = synthetic construct
SEQUENCE: 24
MDIDPYKEFG ATVELLSFLP SDFFPSVRDL LDTASALYRE ALESPEHCSP HHTALRQAIL  60
CWGELMTLAT WVGNNLEDPA SRDLVVNYVN TNMGLKIRQL LWFHISCLTF GRETVLEYLV  120
SFGVWIRTPP AYRPPNAPIL STLPETTVVR RRDRGRSPRR RTPSPRRRRS QSPRRRRSQS  180
RESQCGP                                                          187

SEQ ID NO: 25          moltype = AA  length = 38
FEATURE                Location/Qualifiers
REGION                 1..38
                       note = Synthetic
source                 1..38
                       mol_type = protein
                       organism = synthetic construct
SEQUENCE: 25
RRRDRGRSPR RRTPSPRRRR SQSPRRRRSQ SRESQCGP                        38

SEQ ID NO: 26          moltype = AA  length = 183
FEATURE                Location/Qualifiers
REGION                 1..183
                       note = Synthetic
```

```
source                1..183
                      mol_type = protein
                      organism = synthetic construct
SEQUENCE: 26
MDIDPYKEFG ASVELLSFLP SDFFPSIRDL LDTASALYRE ALESPEHCSP HHTALRQAIL  60
CWGELMNLAT WVGSNLEDPA SRELVVSYVN VNMGLKIRQL LWFHISCLTF GRETVLEYLV  120
SFGVWIRTPP AYRPPNAPIL STLPETTVVR RRGRSPRRRT PSPRRRRSQS PRRRRSQSRE  180
SQC                                                               183

SEQ ID NO: 27         moltype = AA  length = 34
FEATURE               Location/Qualifiers
REGION                1..34
                      note = Synthetic
source                1..34
                      mol_type = protein
                      organism = synthetic construct
SEQUENCE: 27
RRRGRSPRRR TPSPRRRRSQ SPRRRRSQSR ESQC                            34

SEQ ID NO: 28         moltype = AA  length = 183
FEATURE               Location/Qualifiers
REGION                1..183
                      note = Synthetic
source                1..183
                      mol_type = protein
                      organism = synthetic construct
SEQUENCE: 28
MDIDPYKEFG ASVELLSFLP SDFFPSIRDL LDTASALYRE ALESPEHCSP HHTALRQAIL  60
CWGELMNLAT WVGSNLEDPA SRELVVSYVN VNMGLKIRQL LWFHISCLTF GRETVLEYLV  120
SFGVWIRTPP AYRPPNAPIL STLPETTVVR RRGRSPRRRT PSPRRRRSQS PRRRRSQSRE  180
SQC                                                               183

SEQ ID NO: 29         moltype = AA  length = 34
FEATURE               Location/Qualifiers
REGION                1..34
                      note = Synthetic
source                1..34
                      mol_type = protein
                      organism = synthetic construct
SEQUENCE: 29
RRRGRSPRRR TPSPRRRRSQ SPRRRRSQSR ESQC                            34

SEQ ID NO: 30         moltype = AA  length = 183
FEATURE               Location/Qualifiers
REGION                1..183
                      note = Synthetic
source                1..183
                      mol_type = protein
                      organism = synthetic construct
SEQUENCE: 30
MDIDPYKEFG ATVELLSFLP SDFFPSVRDL LDTASALYRE ALESPEHCSP HHTALRQAIL  60
CWGELMTLAT WVGGNLEDPA SRDLVVSYVN TNMGLKFRQL LWFHISCLTF GRETVIEYLV  120
SFGVWIRTPP AYRPPNAPIL STLPETTVVR RRGRSPRRRT PSPRRRRSQS PRRRRSQSRE  180
SQC                                                               183

SEQ ID NO: 31         moltype = AA  length = 34
FEATURE               Location/Qualifiers
REGION                1..34
                      note = Synthetic
source                1..34
                      mol_type = protein
                      organism = synthetic construct
SEQUENCE: 31
RRRGRSPRRR TPSPRRRRSQ SPRRRRSQSR ESQC                            34

SEQ ID NO: 32         moltype = AA  length = 183
FEATURE               Location/Qualifiers
REGION                1..183
                      note = Synthetic
source                1..183
                      mol_type = protein
                      organism = synthetic construct
SEQUENCE: 32
MDIDPYKEFG ATVELLSFLP SDFFPSVRDL LDTASALYRD ALESPEHCSP HHTALRQAIL  60
CWGELMTLAT WVGVNLEDPA SRDLVVSYVN TNMGLKFRQL LWFHISCLTF GRETVIEYLV  120
SFGVWIRTPP AYRPPNAPIL STLPENTVVR RRGRSPRRRT PSPRRRRSQS PRRRRSQSPA  180
SQC                                                               183

SEQ ID NO: 33         moltype = AA  length = 34
```

```
FEATURE                 Location/Qualifiers
REGION                  1..34
                        note = Synthetic
source                  1..34
                        mol_type = protein
                        organism = synthetic construct
SEQUENCE: 33
RRRGRSPRRR TPSPRRRRSQ SPRRRRSQSP ASQC                           34

SEQ ID NO: 34           moltype = AA  length = 183
FEATURE                 Location/Qualifiers
REGION                  1..183
                        note = Synthetic
source                  1..183
                        mol_type = protein
                        organism = synthetic construct
SEQUENCE: 34
MDIDPYKEFG ASVELLSFLP SDFFPSVRDL LDTASALYRD ALESPEHCTP NHTALRQAIL  60
CWGELMTLAS WVGNNLEDPA ARDLVVNYVN TNMGLKIRQL LWFHISCLTF GRETVLEYLV  120
SFGVWIRTPP AYRPPNAPIL STLPETTVVR RRGRSPRRRT PSPRRRRSQS PRRRRSQSPA  180
SQC                                                             183

SEQ ID NO: 35           moltype = AA  length = 34
FEATURE                 Location/Qualifiers
REGION                  1..34
                        note = Synthetic
source                  1..34
                        mol_type = protein
                        organism = synthetic construct
SEQUENCE: 35
RRRGRSPRRR TPSPRRRRSQ SPRRRRSQSP ASQC                           34

SEQ ID NO: 36           moltype = AA  length = 183
FEATURE                 Location/Qualifiers
REGION                  1..183
                        note = Synthetic
source                  1..183
                        mol_type = protein
                        organism = synthetic construct
SEQUENCE: 36
LDIDPYKEFG ATVELLSFLP SDFFPSVRDL LDTASALYRE SLESSDHCSP HHTALRQAIL  60
CWGELMTLAT WVGNNLEDPA SRDLVVNYVN TNMGLKIRQL LWFHISCLTF GRETVLEYLV  120
SFGVWIRTPP AYRPPNAPIL STLPETTVVR RRGRSPRRRT PSPRRRRSQS PRRRRSASPA  180
SQC                                                             183

SEQ ID NO: 37           moltype = AA  length = 34
FEATURE                 Location/Qualifiers
REGION                  1..34
                        note = Synthetic
source                  1..34
                        mol_type = protein
                        organism = synthetic construct
SEQUENCE: 37
RRRGRSPRRR TPSPRRRRSQ SPRRRRSASP ASQC                           34

SEQ ID NO: 38           moltype = AA  length = 183
FEATURE                 Location/Qualifiers
REGION                  1..183
                        note = Synthetic
source                  1..183
                        mol_type = protein
                        organism = synthetic construct
SEQUENCE: 38
MDIDPYKEFG ASVELLSFLP SDFFPSVRDL LDTASALYRD ALESPEHCTP NHTALRQAIL  60
CWGELMTLAS WVGNNLEDPA ARDLVVNYVN TNMGLKIRQL LWFHISCLTF GRETVLEYLV  120
SFGVWIRTPP AYRPPNAPIL STLPETTVVR QRGRAPRRRT PSPRRRRSQS PRRRRSQSPA  180
SQC                                                             183

SEQ ID NO: 39           moltype = AA  length = 34
FEATURE                 Location/Qualifiers
REGION                  1..34
                        note = Synthetic
source                  1..34
                        mol_type = protein
                        organism = synthetic construct
SEQUENCE: 39
RQRGRAPRRR TPSPRRRRSQ SPRRRRSQSP ASQC                           34

SEQ ID NO: 40           moltype = AA  length = 183
```

-continued

```
FEATURE               Location/Qualifiers
REGION                1..183
                      note = Synthetic
source                1..183
                      mol_type = protein
                      organism = synthetic construct
SEQUENCE: 40
MDIDPYKEFG ASVELLSFLP SDFFPSIRDL LDTASALYRE ALESPEHCSP HHTALRQAIV  60
CWGELMNLAT WVGSNLEDPA SRELVVSYVN VNMGLKIRQL LWFHISCLTF GRETVLEYLV  120
SFGVWIRTPP AYRPPNAPIL STLPETTVVR RRGRSPRRRT PSPRRRRSQS PRRRRSQSRE  180
SQC                                                               183
```

What is claimed is:

1. A method of treating chronic HBV in a subject, the method comprising the steps of:

a) administering a treatment for chronic HBV to a subject diagnosed with chronic HBV;

b) performing an assay to detect the presence or level of Hepatitis B core antigen (HBcAg) and phosphorylated Hepatitis B core antigen (P-HBcAg) in at least one sample obtained from the subject, wherein the assay comprises contacting the at least one sample with an antibody that specifically binds to HBcAg and an antibody that specifically binds to P-HBcAg; and c) assessing and monitoring the response to the treatment for chronic HBV based on the presence or level of HBcAg and P-HBcAg in the at least one sample.

2. The method of claim 1, wherein the method further comprises altering the treatment for HBV based on the presence or level of HBcAg and P-HBcAg in the at least one sample.

3. A method of treating chronic Hepatitis B (HBV) infection in a subject, the method comprising the steps of:

a) performing an assay to detect the presence or level of Hepatitis B core antigen (HBcAg) in at least one sample obtained from a subject diagnosed with chronic HBV, wherein the assay comprises contacting the at least one sample with an antibody that specifically binds to HBcAg;

b) determining the amount of infectious HBV particles in the at least one sample based upon the presence or level of HBcAg in the at least one sample, c) identifying the subject as having an amount of infectious HBV particles in the at least one sample equal to or above a threshold value; and d) providing a treatment for chronic HBV to the subject identified as having an amount of infectious HBV particles in the at least one sample equal to or above a threshold value.

4. A method of treating chronic Hepatitis B (HBV) infection in a subject, the method comprising the steps of:

a) administering a treatment for chronic HBV to a subject diagnosed with chronic HBV;

b) performing an assay to detect the presence or level of Hepatitis B core antigen (HBcAg) in at least one sample obtained from a subject receiving a treatment for chronic HBV, wherein the assay comprises contacting the at least one sample with an antibody that specifically binds to HBcAg;

c) determining the amount of infectious HBV particles in the at least one sample based upon the presence or level of HBcAg in the at least one sample; and d) determining that the treatment is efficacious when the amount of infectious HBV particles in the at least one sample is less than a reference level; or determining that the treatment is not efficacious when the amount of infectious HBV particles in the at least one sample is greater than or equal to a reference level.

5. A method of treating chronic Hepatitis B (HBV) infection in a subject, the method comprising the steps of:

a) administering a treatment for chronic HBV to a subject diagnosed with chronic HBV;

b) performing an assay to detect the presence or level of Hepatitis B core antigen (HBcAg) and phosphorylated Hepatitis B core antigen (P-HBcAg) in at least one sample obtained from a subject receiving a treatment for chronic HBV, wherein the assay comprises contacting the at least one sample with an antibody that specifically binds to HBcAg and an antibody that specifically binds to P-HBcAg;

c) determining the amount of infectious HBV particles in the at least one sample based upon the presence or level of HBcAg in the at least one sample;

d) determining the amount of non-infectious HBV particles in the at least one sample based upon the presence or level of P-HBcAg in the at least one sample; and e) determining response to the treatment for chronic HBV based upon the amount of infectious and/or non-infectious HBV particles in the at least one sample.

6. The method of claim 5, wherein:

a) the treatment is determined to be efficacious when the amount of infectious HBV particles in the at least one sample is less than a reference level;

b) the treatment is determined to be efficacious when the amount of infectious HBV particles in the at least one sample is less than a reference level and the amount of non-infectious HBV particles in the at least one sample is less than a reference level; or c) the treatment is determined to not be efficacious when the amount of infectious HBV particles in the at least one sample is greater than or equal to a reference level.

7. A method of treating chronic Hepatitis B (HBV) infection in a subject, the method comprising the steps of:

a) administering a treatment for chronic HBV to a subject diagnosed with chronic HBV;

b) performing an assay to detect the presence or level of Hepatitis B core antigen (HBcAg) and phosphorylated Hepatitis B core antigen (P-HBcAg) in at least two samples obtained from a subject receiving a treatment for chronic HBV, wherein the at least two samples comprise a first sample obtained from the subject at a first time point before or after receiving the treatment for chronic HBV and a second sample obtained from the subject at a second time point after the first time point, and wherein the assay comprises contacting the at least two samples with an antibody that specifically binds to HBcAg and an antibody that specifically binds to P-HBcAg;

c) determining the amount of infectious HBV particles in the at least two samples based upon the presence or level of HBcAg and/or determining the amount of non-infectious HBV particles in the at least two samples based upon the presence or level of P-HBcAg; and d) determining response to the treatment for chronic HBV based upon the amount of infectious and/or non-infectious HBV particles in the at least two samples.

8. The method of claim 7, wherein:

a) the treatment is determined to be efficacious when the amount of infectious HBV particles in the second sample reduced by at least an absolute amount compared to the amount of infectious HBV particles in the first sample;

b) the treatment is determined to be efficacious when the amount of infectious HBV particles in the second sample reduced by at least an absolute amount compared to the amount of infectious HBV particles in the first sample and wherein the amount of non-infectious HBV particles in the second sample is reduced by at least an absolute amount compared to the amount of non-infectious HBV particles in the first sample; or c) the treatment is determined to not be efficacious when the amount of infectious HBV particles in the second sample is not reduced by at least an absolute amount compared to the amount of infectious HBV particles in the first sample.

9. The method of claim 8, wherein the first sample is obtained from the subject within 24 hours of receiving the treatment for chronic HBV and the second sample is obtained from the subject 10-14 weeks after the first sample.

10. The method of claim 4, further comprising altering the treatment for chronic HBV when the treatment is determined to not be efficacious.

11. The method of claim 10, wherein altering the treatment for chronic HBV comprises providing to the subject an increased dose of the treatment, increasing the frequency of dosing with the treatment, providing to the subject a second treatment, or any combination thereof.

12. The method of claim 1, wherein the antibody that specifically binds to HBcAg binds to an epitope comprising at least 3 amino acids of SEQ ID NO: 2 or SEQ ID NO:25 and/or wherein the antibody that specifically binds to P-HBcAg binds to an epitope comprising at least 3 amino acids of SEQ ID NO: 2 or SEQ ID NO:25, provided that at least one amino acid of SEQ ID NO: 2 or SEQ ID NO:25 is phosphorylated.

13. The method of claim 1, wherein the treatment for chronic HBV is an interferon, nucleos(t)ide analogue, a nucleic acid, an immunomodulator, a core protein assembly inhibitor, a capsid assembly modulator (CAM), an HBsAg release inhibitor, an entry inhibitor, interfering RNA, a DNA or RNA modifying agent, or a combination thereof.

14. The method of claim 13, wherein:

a) the interferon is interferon alpha-2a or PEGylated interferon alpha-2a;

b) the nucleos(t)ide analogue is lamivudine, adefovir, tenofovir, telbivudine, or entecavir;

c) the nucleic acid is an siRNA, an antisense oligonucleotide, an shRNA, or a miRNA;

d) the core protein assembly inhibitor is NVR 3-1983, GLS4 or BAY 41-4109;

e) the CAM is JNJ-632, AT130, or BAY41-4109;

f) the HBsAg release inhibitor is REP 9 AC;

g) the entry inhibitor is Myrcludex-B; or h) any combination of a)-g).

15. The method of claim 1, wherein performing the assay to measure the level of HBcAg in the at least one sample comprises contacting the at least one sample, either simultaneously or sequentially, in any order with:

a) a Hepatitis B core antigen (HBcAg) capture antibody which binds to an epitope on the C-terminus of HBcAg to form a capture antibody-HBcAg complex; and b) a detection antibody binds to an epitope on HBcAg that is not bound by the HBcAg capture antibody, such that a capture antibody-HBcAg-detection antibody complex is formed; and c) measuring the level of HBcAg in the sample based on a signal generated by a detectable label in the capture antibody-HBcAg-detection antibody complex.

16. The method of claim 1, wherein performing the assay to measure the level of P-HBcAg in the sample comprises contacting the sample, either simultaneously or sequentially, in any order with:

a) a phosphorylated Hepatitis B core antigen (P-HBcAg) capture antibody which binds to an epitope on the C-terminus of P-HBcAg to form a capture antibody-P-HBcAg complex; and b) a detection antibody binds to an epitope on P-HBcAg that is not bound by the P-HBcAg capture antibody, such that a capture antibody-P-HBcAg-detection antibody complex is formed; and c) measuring the level of P-HBcAg in the sample based on a signal generated by a detectable label in the capture antibody-P-HBcAg-detection antibody complex.

* * * * *